(12) United States Patent
Bradley et al.

(10) Patent No.: US 9,103,775 B2
(45) Date of Patent: *Aug. 11, 2015

(54) NANO-ELECTRONIC SENSORS FOR CHEMICAL AND BIOLOGICAL ANALYTES, INCLUDING CAPACITANCE AND BIO-MEMBRANE DEVICES

(75) Inventors: Keith Bradley, New York, NY (US);
Ying-Lan Chang, Cupertino, CA (US);
Jean-Christophe P. Gabriel, Pinole, CA (US); John Loren Passmore, Berkeley, CA (US); Sergei Skarupo, Berkeley, CA (US); Eugene Tu, San Diego, CA (US);
Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/442,856

(22) Filed: Apr. 10, 2012

(65) Prior Publication Data
US 2013/0075794 A1 Mar. 28, 2013

Related U.S. Application Data

(60) Continuation of application No. 11/400,038, filed on Apr. 6, 2006, now Pat. No. 8,154,093, which is a continuation-in-part of application No. 11/090,550, filed on Mar. 25, 2005, now abandoned, which is a
(Continued)

(51) Int. Cl.
*H01L 29/06* (2006.01)
*G01N 27/414* (2006.01)
*B82Y 10/00* (2011.01)
*B82Y 15/00* (2011.01)

(52) U.S. Cl.
CPC ............ *G01N 27/4146* (2013.01); *B82Y 10/00*
(2013.01); *H01L 29/0665* (2013.01); *H01L 29/0673* (2013.01); *B82Y 15/00* (2013.01); *G01N 27/4145* (2013.01); *Y10S 977/742* (2013.01)

(58) Field of Classification Search
None
See application file for complete search history.

(56) References Cited

U.S. PATENT DOCUMENTS

| 3,860,430 A | 1/1975 | Walker et al. |
| 4,022,059 A | 5/1977 | Schontzler et al. |
| 4,795,968 A | 1/1989 | Madou et al. |
| 4,851,195 A | 7/1989 | Matthews et al. |

(Continued)

FOREIGN PATENT DOCUMENTS

| CN | 1546365 A | 11/2004 |
| CN | 101035620 A | 9/2007 |

(Continued)

OTHER PUBLICATIONS

U.S. Appl. No. 12/960,200, filed Dec. 3, 2010, Bradley et al.
(Continued)

*Primary Examiner* — Benjamin Sandvik
(74) *Attorney, Agent, or Firm* — Weaver Austin Villeneuve & Sampson LLP

(57) ABSTRACT

Embodiments of nanoelectronic sensors are described, including sensors for detecting analytes inorganic gases, organic vapors, biomolecules, viruses and the like. A number of embodiments of capacitive sensors having alternative architectures are described. Particular examples include integrated cell membranes and membrane-like structures in nanoelectronic sensors.

7 Claims, 21 Drawing Sheets

Related U.S. Application Data division of application No. 10/280,265, filed on Oct. 26, 2002, now Pat. No. 6,894,359, said application No. 11/400,038 is a continuation-in-part of application No. 10/345,783, filed on Jan. 16, 2003, now abandoned, said application No. 11/400,038 is a continuation-in-part of application No. 10/704,066, filed on Nov. 7, 2003, now abandoned, said application No. 11/400,038 is a continuation-in-part of application No. 11/318,354, filed on Dec. 23, 2005, now abandoned.

(60) Provisional application No. 60/408,412, filed on Sep. 4, 2002, provisional application No. 60/349,670, filed on Jan. 16, 2002, provisional application No. 60/424,892, filed on Nov. 8, 2002, provisional application No. 60/748,834, filed on Dec. 9, 2005, provisional application No. 60/738,694, filed on Nov. 21, 2005, provisional application No. 60/730,905, filed on Oct. 27, 2005, provisional application No. 60/668,879, filed on Apr. 5, 2005, provisional application No. 60/657,275, filed on Feb. 28, 2005, provisional application No. 60/639,954, filed on Dec. 28, 2004.

(56) References Cited

U.S. PATENT DOCUMENTS

| | | |
|---|---|---|
| 4,909,919 A | 3/1990 | Morris et al. |
| 4,935,345 A | 6/1990 | Guilbeau et al. |
| 4,945,045 A | 7/1990 | Forrest et al. |
| 5,246,859 A | 9/1993 | Nelson et al. |
| 5,258,415 A | 11/1993 | Hahn et al. |
| 5,382,417 A | 1/1995 | Haase |
| 5,448,905 A | 9/1995 | Stetter et al. |
| 5,618,496 A | 4/1997 | Hasumi et al. |
| 5,674,752 A | 10/1997 | Buckley et al. |
| 5,759,773 A | 6/1998 | Tyagi et al. |
| 5,827,997 A | 10/1998 | Chung et al. |
| 5,866,434 A | 2/1999 | Massey et al. |
| 5,958,340 A | 9/1999 | Meyer et al. |
| 5,993,694 A | 11/1999 | Ito et al. |
| 6,004,494 A | 12/1999 | Debe et al. |
| 6,010,459 A | 1/2000 | Silkoff et al. |
| 6,031,454 A | 2/2000 | Lovejoy et al. |
| 6,033,916 A | 3/2000 | Sieben et al. |
| 6,044,843 A | 4/2000 | O'Neil et al. |
| 6,090,545 A | 7/2000 | Wohlstadter et al. |
| 6,111,280 A | 8/2000 | Gardner et al. |
| 6,217,828 B1 | 4/2001 | Bretscher et al. |
| 6,286,226 B1 | 9/2001 | Jin |
| 6,287,874 B1 | 9/2001 | Hefti |
| 6,320,295 B1 | 11/2001 | McGill et al. |
| 6,346,189 B1 | 2/2002 | Dai et al. |
| 6,445,006 B1 * | 9/2002 | Brandes et al. ............... 257/76 |
| 6,465,132 B1 | 10/2002 | Jin |
| 6,482,639 B2 | 11/2002 | Snow et al. |
| 6,485,905 B2 | 11/2002 | Hefti |
| 6,489,394 B1 | 12/2002 | Andros |
| 6,528,020 B1 | 3/2003 | Dai et al. |
| 6,577,242 B2 | 6/2003 | Jen et al. |
| 6,628,053 B1 * | 9/2003 | Den et al. ............... 313/310 |
| 6,656,712 B1 | 12/2003 | Balavoine et al. |
| 6,676,904 B1 | 1/2004 | Lee et al. |
| 6,797,325 B2 | 9/2004 | Wang et al. |
| 6,890,780 B2 | 5/2005 | Lee |
| 6,894,359 B2 | 5/2005 | Bradley et al. |
| 7,013,708 B1 * | 3/2006 | Cho et al. ............... 73/31.05 |
| 7,015,046 B2 | 3/2006 | Wohlstadter et al. |
| 7,109,859 B2 | 9/2006 | Peeters |
| 7,262,991 B2 | 8/2007 | Zhang et al. |
| 7,271,720 B2 | 9/2007 | Tabe |
| 7,312,095 B1 | 12/2007 | Gabriel et al. |
| 7,449,757 B2 | 11/2008 | Bradley et al. |
| 7,473,651 B2 | 1/2009 | Moriya et al. |
| 7,522,040 B2 | 4/2009 | Passmore et al. |
| 7,547,931 B2 | 6/2009 | Star et al. |
| 7,948,041 B2 | 5/2011 | Bryant et al. |
| 8,154,093 B2 | 4/2012 | Bradley et al. |
| 8,754,454 B2 | 6/2014 | Bryant et al. |
| 2002/0012937 A1 | 1/2002 | Tender et al. |
| 2002/0014667 A1 | 2/2002 | Shin et al. |
| 2002/0017300 A1 | 2/2002 | Hickle et al. |
| 2002/0092779 A1 | 7/2002 | Essalik et al. |
| 2002/0117659 A1 * | 8/2002 | Lieber et al. ............... 257/14 |
| 2002/0118027 A1 | 8/2002 | Routkevitch et al. |
| 2002/0127733 A1 | 9/2002 | Kovacs |
| 2002/0130333 A1 | 9/2002 | Watanabe et al. |
| 2002/0172639 A1 * | 11/2002 | Horiuchi et al. ............. 423/447.2 |
| 2002/0172963 A1 | 11/2002 | Kelley et al. |
| 2003/0031620 A1 | 2/2003 | Harutyunyan et al. |
| 2003/0036065 A1 | 2/2003 | Gellibolian |
| 2003/0041438 A1 | 3/2003 | Wei et al. |
| 2003/0073919 A1 | 4/2003 | Hampton et al. |
| 2003/0113713 A1 | 6/2003 | Glezer et al. |
| 2003/0134267 A1 * | 7/2003 | Kang et al. ............... 435/4 |
| 2003/0134433 A1 | 7/2003 | Gabriel et al. |
| 2003/0139003 A1 | 7/2003 | Gole et al. |
| 2003/0171257 A1 | 9/2003 | Stirbl et al. |
| 2003/0175161 A1 | 9/2003 | Gabriel et al. |
| 2003/0180640 A1 | 9/2003 | Darty |
| 2003/0199172 A1 * | 10/2003 | Rueckes et al. ............. 438/754 |
| 2003/0211637 A1 | 11/2003 | Schoeniger et al. |
| 2004/0011291 A1 | 1/2004 | Delaunay et al. |
| 2004/0018587 A1 | 1/2004 | Makowski et al. |
| 2004/0023428 A1 | 2/2004 | Gole et al. |
| 2004/0029297 A1 | 2/2004 | Bonnell et al. |
| 2004/0033525 A1 | 2/2004 | Monforte et al. |
| 2004/0043527 A1 | 3/2004 | Bradley et al. |
| 2004/0065970 A1 | 4/2004 | Blanchet-Fincher |
| 2004/0067530 A1 | 4/2004 | Gruner |
| 2004/0091285 A1 | 5/2004 | Lewis |
| 2004/0104129 A1 | 6/2004 | Gu et al. |
| 2004/0119141 A1 | 6/2004 | Schreiter et al. |
| 2004/0120183 A1 | 6/2004 | Appenzeller et al. |
| 2004/0132070 A1 | 7/2004 | Star et al. |
| 2004/0136866 A1 | 7/2004 | Pontis et al. |
| 2004/0158410 A1 | 8/2004 | Ono et al. |
| 2004/0188780 A1 | 9/2004 | Kurtz |
| 2004/0192072 A1 | 9/2004 | Snow et al. |
| 2004/0200734 A1 | 10/2004 | Co et al. |
| 2004/0202603 A1 | 10/2004 | Fischer et al. |
| 2004/0204915 A1 | 10/2004 | Steinthal et al. |
| 2004/0211580 A1 | 10/2004 | Wang et al. |
| 2004/0214176 A1 | 10/2004 | Osborne et al. |
| 2004/0219090 A1 | 11/2004 | Dziedzic et al. |
| 2005/0003355 A1 | 1/2005 | Lu et al. |
| 2005/0065741 A1 | 3/2005 | Segal et al. |
| 2005/0072213 A1 | 4/2005 | Besnard et al. |
| 2005/0103097 A1 | 5/2005 | Faltum et al. |
| 2005/0112052 A1 | 5/2005 | Gu et al. |
| 2005/0129573 A1 | 6/2005 | Gabriel et al. |
| 2005/0157445 A1 | 7/2005 | Bradley et al. |
| 2005/0211572 A1 | 9/2005 | Buck et al. |
| 2005/0245836 A1 | 11/2005 | Star et al. |
| 2005/0255313 A1 | 11/2005 | Kyotani et al. |
| 2005/0279987 A1 | 12/2005 | Star et al. |
| 2006/0009707 A1 | 1/2006 | Daniels et al. |
| 2006/0009797 A1 | 1/2006 | Armstrong |
| 2006/0014172 A1 | 1/2006 | Muller et al. |
| 2006/0035215 A9 | 2/2006 | Sorge et al. |
| 2006/0040294 A1 | 2/2006 | Prudent et al. |
| 2006/0054936 A1 | 3/2006 | Lieber et al. |
| 2006/0055392 A1 | 3/2006 | Passmore et al. |
| 2006/0102494 A1 | 5/2006 | Chueh et al. |
| 2006/0228723 A1 | 10/2006 | Bradley et al. |
| 2006/0232278 A1 | 10/2006 | Diamond et al. |
| 2006/0249402 A1 | 11/2006 | Snow et al. |
| 2006/0263255 A1 | 11/2006 | Han et al. |
| 2007/0048181 A1 | 3/2007 | Chang et al. |
| 2007/0114138 A1 | 5/2007 | Krasteva et al. |
| 2007/0114573 A1 | 5/2007 | Han et al. |
| 2007/0132043 A1 | 6/2007 | Bradley et al. |
| 2007/0158642 A1 | 7/2007 | Gruner |

(56) References Cited

U.S. PATENT DOCUMENTS

| | | | |
|---|---|---|---|
| 2007/0178477 | A1 | 8/2007 | Joiner et al. |
| 2007/0208243 | A1 | 9/2007 | Gabriel et al. |
| 2007/0259359 | A1 | 11/2007 | Briman et al. |
| 2007/0281156 | A1 | 12/2007 | Lieber et al. |
| 2008/0021339 | A1 | 1/2008 | Gabriel et al. |
| 2008/0093226 | A1 | 4/2008 | Briman et al. |
| 2008/0159960 | A1 | 7/2008 | Klingeler et al. |
| 2008/0221806 | A1 | 9/2008 | Bryant et al. |
| 2009/0101996 | A1 | 4/2009 | Bradley et al. |
| 2009/0165533 | A1 | 7/2009 | Han |
| 2010/0047901 | A1 | 2/2010 | Bradley et al. |
| 2010/0085067 | A1 | 4/2010 | Gabriel et al. |
| 2010/0137731 | A1 | 6/2010 | Star et al. |
| 2012/0006102 | A1 | 1/2012 | Bryant et al. |
| 2012/0052004 | A1 | 3/2012 | Wilson et al. |
| 2012/0178187 | A1 | 7/2012 | Radtkey et al. |
| 2013/0075794 | A1 | 3/2013 | Bradley et al. |

FOREIGN PATENT DOCUMENTS

| | | |
|---|---|---|
| EP | 1 645 871 A1 | 4/2006 |
| EP | 1 664 724 | 6/2006 |
| EP | 1 680 353 | 7/2006 |
| EP | 1 941 270 | 7/2008 |
| EP | 07 754 869.1 | 12/2008 |
| JP | 2002-503204 | 1/2002 |
| JP | 2003-517604 | 5/2003 |
| JP | 2005-507121 | 3/2005 |
| KR | 10-2004-0080184 A | 9/2004 |
| KR | 10-2006-0100811 A | 9/2006 |
| KR | 10-2007-0089236 A | 8/2007 |
| WO | WO 97/32571 | 9/1997 |
| WO | WO 01/32951 | 5/2001 |
| WO | WO 01/44796 | 6/2001 |
| WO | WO 02/15240 | 2/2002 |
| WO | WO 02/48701 | 6/2002 |
| WO | WO 02/079514 | 10/2002 |
| WO | WO 02/095099 | 11/2002 |
| WO | WO 03/016901 | 2/2003 |
| WO | WO 03/046536 | 6/2003 |
| WO | WO 2004/044586 | 5/2004 |
| WO | WO 2004/104568 | 12/2004 |
| WO | WO 2005/026694 | 3/2005 |
| WO | WO 2005/047468 | 5/2005 |
| WO | WO 2005/062031 | 7/2005 |
| WO | WO 2005/094221 | 10/2005 |
| WO | WO 2005/097672 | 10/2005 |
| WO | WO 2006/024023 | 3/2006 |
| WO | WO 2006/068250 | 6/2006 |
| WO | WO 2006/071895 | 7/2006 |
| WO | WO 2007/114931 | 10/2007 |
| WO | WO 2008/039165 | 4/2008 |
| WO | WO 2008/052104 | 5/2008 |
| WO | WO 2011/017660 | 2/2011 |
| WO | WO 2011/017660 A3 | 2/2011 |

OTHER PUBLICATIONS

U.S. Appl. No. 14/306,156, filed Jun. 16, 2014, Bryant et al.
US Office Action dated Dec. 12, 2007 issued in U.S. Appl. No. 10/655,529.
US Office Action Final dated Jul. 3, 2008 issued in U.S. Appl. No. 10/655,529.
US Office Action dated Mar. 17, 2006 issued in U.S. Appl. No. 10/656,898.
US Office Action Final dated Oct. 20, 2006 issued in U.S. Appl. No. 10/656,898.
US Office Action dated May 7, 2007 issued in U.S. Appl. No. 10/656,898.
US Office Action Final dated Jan. 17, 2008 issued in U.S. Appl. No. 10/656,898.
US Office Action dated Jul. 24, 2008 issued in U.S. Appl. No. 10/656,898.
US Office Action dated Jul. 14, 2008 issued in U.S. Appl. No. 11/019,792.
US Notice of Allowance dated Feb. 11, 2009 issued in U.S. Appl. No. 11/019,792.
US Office Action dated Jul. 26, 2010 issued in U.S. Appl. No. 12/485,793.
US Office Action Final dated Feb. 10, 2011 issued in U.S. Appl. No. 12/485,793.
US Office Action dated Apr. 16, 2008 in U.S. Appl. No. 11/488,456.
US Office Action Final dated Jan. 14, 2009 in U.S. Appl. No. 11/488,456.
US Office Action dated Jun. 1, 2005 issued in U.S. Appl. No. 10/940,324.
US Office Action dated Mar. 3, 2006 issued in U.S. Appl. No. 10/940,324.
US Office Action dated Sep. 7, 2006 issued in U.S. Appl. No. 10/940,324.
US Office Action Final dated Feb. 21, 2007 issued in U.S. Appl. No. 10/940,324.
US Office Action dated Aug. 27, 2007 issued in U.S. Appl. No. 10/940,324.
US Office Action Final dated May 27, 2008 issued in U.S. Appl. No. 10/940,324.
US Office Action dated Aug. 12, 2008 issued in U.S. Appl. No. 10/940,324.
US Office Action dated Apr. 16, 2009 issued in U.S. Appl. No. 10/940,324.
US Office Action dated Apr. 1, 2008 issued in U.S. Appl. No. 11/111,121.
US Notice of Allowance dated Oct. 8, 2008 issued in U.S. Appl. No. 11/111,121.
US Office Action dated Dec. 2, 2005 issued in U.S. Appl. No. 10/945,803.
US Office Action Final dated Apr. 6, 2007 issued in U.S. Appl. No. 10/945,803.
US Office Action Final dated Sep. 12, 2007 issued in U.S. Appl. No. 10/945,803.
US Office Action dated Jun. 12, 2008 issued in U.S. Appl. No. 10/945,803.
US Notice of Allowance dated Jul. 7, 2008 issued in U.S. Appl. No. 10/945,803.
US Office Action Final dated Nov. 2, 2009 issued in U.S. Appl. No. 12/268,327.
US Office Action dated Jun. 1, 2006 issued in U.S. Appl. No. 10/704,066.
US Office Action Final dated Jan. 24, 2007 issued in U.S. Appl. No. 10/704,066.
US Office Action dated Aug. 24, 2007 issued in U.S. Appl. No. 10/704,066.
US Notice of Abandonment and Examiner Interview Summary dated Mar. 6, 2008 issued in U.S. Appl. No. 10/704,066.
US Office Action dated Feb. 25, 2008 issued in U.S. Appl. No. 11/274,747.
US Examiner Interview Summary dated May 28, 2008 issued in U.S. Appl. No. 11/274,747.
US Office Action Final dated Feb. 11, 2009 issued in U.S. Appl. No. 11/274,747.
US Office Action dated Oct. 3, 2008 issued in U.S. Appl. No. 11/400,038.
US Office Action Final dated Jul. 7, 2009 issued in U.S. Appl. No. 11/400,038.
US Office Action dated Feb. 4, 2011 issued in U.S. Appl. No. 11/400,038.
US Notice of Allowance dated Nov. 25, 2011 issued in U.S. Appl. No. 11/400,038.
US Office Action dated May 12, 2010 issued in U.S. Appl. No. 11/924,328.
US Notice of Allowance dated Dec. 16, 2010 issued in U.S. Appl. No. 11/924,328.
US Notice of Allowance dated Jan. 21, 2011 issued in U.S. Appl. No. 11/924,328.
US Office Action (Notice to file Corrected Application Papers) dated Jan. 27, 2011 issued in U.S. Appl. No. 11/924,328.

(56) References Cited

OTHER PUBLICATIONS

US Response to Rule 312 Communication dated Feb. 11, 2011 issued in U.S. Appl. No. 11/924,328.
US Notice of Allowance dated Jun. 19, 2013 issued in U.S. Appl. No. 13/084,465.
US Notice of Allowance dated Oct. 8, 2013 issued in U.S. Appl. No. 13/084,465.
US Notice of Allowance dated Jan. 27, 2014 issued in U.S. Appl. No. 13/084,465.
US Office Action dated Nov. 19, 2012 issued in U.S. Appl. No. 13/389,247.
US Final Office Action dated Jun. 7, 2013 issued in U.S. Appl. No. 13/389,247.
US Office Action dated Apr. 7, 2014 issued in U.S. Appl. No. 13/389,247.
PCT International Search Report dated Jun. 11, 2008 issued in PCT/US2006/028079.
PCT International Written Opinion dated Jun. 11, 2008 issued in PCT/US2006/028079.
PCT International Preliminary Report on Patentability and Written Opinion dated Jul. 1, 2008 issued in PCT/US2006/028079.
EP Extended Search Report, Supplementary European Search Report and the European Search Opinion dated Feb. 11, 2011 issued in EP 06 85 1621.
PCT International Search Report dated Oct. 27, 2008 issued in PCT/US2007/008422.
PCT International Written Opinion dated Oct. 27, 2008 issued in PCT/US2007/008422.
PCT International Preliminary Report on Patentability and Written Opinion dated Nov. 27, 2008 issued in PCT/US2007/008422.
EP Extended EP Search Report, Supplementary EP Search Report, and EP Search Opinion dated Nov. 10, 2009 issued in EP 07 75 4869.1.
EP Examination Report dated Mar. 5, 2010 issued in EP 07 75 4869.1.
PCT International Search Report dated Sep. 22, 2005 issued in PCT/US2004/030136.
PCT International Written Opinion dated Sep. 22, 2005 issued in PCT/US2004/030136.
PCT International Preliminary Report on Patentability and Written Opinion dated Jul. 31, 2006 issued in PCT/US2004/030136.
European Search Report dated Mar. 30, 2007 issued in EP 04 788 761.
European Examination Report dated Feb. 10, 2010 issued in EP 04 788 761.7.
European Examination Report dated Jul. 13, 2010 issued in EP03768779.5.
PCT International Search Report dated Nov. 6, 2007 issued in PCT/US2004/030562.
PCT International Written Opinion dated Nov. 6, 2007 issued in PCT/US2004/030562.
PCT International Preliminary Report on Patentability and Written Opinion dated Nov. 23, 2007 issued in PCT/US2004/030562.
European Supplementary Search Report dated Mar. 9, 2012 issued in EP 04 821 666.7.
European Examination Report dated Oct. 9, 2012 issued in EP 04 821 666.7.
PCT International Search Report dated Mar. 30, 2004 issued in WO 2004/044586.
PCT International Preliminary Examination Report dated Nov. 16, 2006 issued in WO 2004/044586.
European Examination Report dated May 19, 2006 issued in EP03768779.5.
European Examination Report dated Dec. 22, 2009 issued in EP03768779.5.
Japanese Office Action dated Jul. 13, 2010 issued in JP 2006-526418.
Japanese Office Action issued Oct. 8, 2009 issued in JP2005-507121 (as translated by foreign associate in letter dated Nov. 2, 2009), 3pgs.
PCT International Search Report dated Jun. 11, 2008 issued in WO 2008/052104.
PCT International Preliminary Report on Patentability and Written Opinion dated Jun. 11, 2008 issued in WO2008/052104.
PCT International Search Report dated Apr. 29, 2011 issued in PCT/US2010/044778.
PCT International Preliminary Report on Patentability and Written Opinion dated Feb. 16, 2012 issued in PCT/US2010/044778.
Chinese Office Action dated Sep. 3, 2013 issued in CN 201080035150.6.
European Extended Search Report dated May 24, 2013 issued in EP 10 807 259.6.
Ang, L.M. et al.(Jan. 1, 2000) "Decoration of activated carbon nanotubes with copper and nickel," *Carbon, Elsevier*, Oxford, GB, 38(3):363-372, XP004186284.
Baeumner A.J., et al., (Jan. 1, 2004) "A Universal Nucleic Acid Sequence Biosensor With Nanomolar Detection Limits," *Analytical Chemistry* 20040215, American Chemical Society, 76(4):888-894.
Cai, D. et al., (2005) "Highly efficient molecular delivery into mammalian cells using carbon nanotube spearing", *Nature Methods*, 2(6):449-454.
Choi, Hee Cheul et al., (Aug. 1, 2002) "Spontaneous Reduction of Metal Ions on the Sidewalls of Carbon Nanotubes," *Journal of the American Chemical Society*, 124(31):9058-9059, XP55019757.
Collins et al., (Apr. 2, 2001) "Current Saturation and Electrical breakdown in Multiwalled Carbon Nanotubes", *Phys. Rev. Lett.*, 86(14):3128-3131.
Collins et al., (Apr. 27, 2001) "Engineering Carbon Nanotubes and Nanotube Circuits Using Electrical Breakdown", *Science*, 292:706-709.
Cui, Yi et al., (2001) "Nanowire Nanosensors for Highly Sensitive and Selective Detection of Biological and Chemical Species", *Science*, 293:1289-1292.
Dai, H. (2002) "Carbon nanotubes: opportunities and challenges", *Surface Science*, 500:218-241.
Derycke et al., (Sep. 2001) "Carbon Nanotube Inter-and Intramolecular Logic Gates", *Nano Letters*, 1(9):453-456.
Duck et al., (Jan. 1, 1990) "Probe Amplifier System Based on Chimeric Cycling Obigonucleotides," Biotechniques, Natick, MA, 9(2), XP000406092, 9(2):Abtract; figure 1.
Gabriel et al. (2003) "Large Scale Production of Carbon Nanotube Transistors: A Generic Platform for Chemical Sensors", *Mat. Res. Soc. Symp. Proc.*vol. 776:Q12.7.1-Q12.7.7.
Goodrich, Terry, et al, (Apr. 7, 2004) Direct Detection of Genomic DNA by Enzymatically Amplified SPR Imaging Measurements of RNA Microarrays, Journal of the American Chemical Society, 126(13):4086-4087.
Harutyunyan A. R. et al. (May 1, 2002) "Carbon Nanotubes for Medical Applications," *European Cells and Materials, Swiss Society for Biomaterials*, 3(Supplement 2):84-87, XP002365698, ISSN: 1473-2262.
Hu, P. et al., (2008) "Magnetic particle-based sandwich sensor with DNS-modified carbon nanotubes as recognition elements for detection of DNA hybridization", *Analytical Chemistry*, 80(5):1819-1823.
Kong et al., (Sep. 14, 2001) "Functionalized Carbon Nanotubes for Molecular Hydrogen sensors", *Adv. Mater*, 13(18):1384-1386, XP002504653.
Lee, et al. (Aug. 15, 2005) "Enzymatically Amplified Surface Plasmon Resonance Imaging detection of DNA by Exonuclease III Digestion of DNA Microarrays," *Chemical Society* US, 77(16):5096-5100.
Lin, Y. et al., (2006) "Carbon nanotubes for immunomagnetic separation of *Escherichia coli* 0157:H7", *J. Nanosci. Nanotechnol.* 6(3):868-871.
Lin, Yi et al., (Jan. 18, 2002) "Functionalization Multiple-Walled Carbon Nanotubes with Aminopolymers," *Jnl of Phy Chem, B, Materials, Surfaces, Interfaces and Biophysical*, Washington DC U.S. 106(6)1294-1298; XP002971880.
Ng, H.T. et al., (Dec. 2001) "Flexible Carbon Nanotube Membrane Sensory System: A Generic Platform", *Journal of Nanoscience and Nanotechnology*, 1(4):375-379.
Ong et al., (Nov. 2, 2001) "A Carbon Nanotube-based Sensor for $CO_2$ Monitoring", *Sensors, MDPI*, BASEL, SU, 1(6):193-205.

(56) References Cited

OTHER PUBLICATIONS

Pearce, Megan E. et al.(Aug. 8, 2007) "Multifunctional Nanorods for Biomedical Applications," *Pharmaceutical Research, Kluwer Academic Publishers-Plenum Publishers*, 24(12):2335-2352, XP01955914, ISSN 1573-904X, DO1: 10.1 007/S11 095-007-9380-7.

Perkins et al. (Apr. 16, 2001) "Electrical and materials properties of $ZrO_2$ gate dielectrics grown by atomic layer chemical vapor deposition", *Applied Physics Letters*, 78(16):2357-2359.

Qi et al., (2003) "Toward Large Arrays of Multiplex Functionalized Carbon Nanoturbe Sensors for Highly Sensitive and Selective Molecular Detection", *Nano Letters*, 3(3):347-351.

Radosavljevic et al. (2001) "High-Field electrical transport and breakdown in bundles of single-wall carbon nanotubes", *Phy. Rev. B.* 64, pp. 241307-1 to 241307-4.

Shim et al., (2001) "Polymer Functionalization for Air-Stable n-Type Carbon Nanotube Field-Effect Transistors", *J Am. Chem Soc.*, 123(46):11512-11513.

Shim et al. (2002) "Functionalization of Carbon Nanotubes for Biocompatibility and Biomolecular Recognition", *Nano Letter*, 2(4):285-288, Published on Web Jan. 25, 2002.

Simon, (2001) "Micromachined metal Oxide gas sensors: opportunities to improve sensor performance", *Sensors and Actuators*, 73:1-26.

Skubal et al.(2002) "Detection and identification of gaseous organics using a $TiO_2$ sensor", *Journal of Photochemistry and Photobiology A: Chemistry*, 148:103-108.

Soldano, C. et al., (2008) "Detection of nanoscale magnetic activity using a single carbon nanotube", *Nano Letter*, 8(12):4498-4505.

Star et al., (Jan. 1, 2003) "Electronic Detection of Specific Protein Binding Using Nanotube", Nano Letters, ACS Washington DC, US, 3(4):459-463 XP002993429.

Star et al. (Jan. 24, 2006) "Label-free detection of DNA hybridzation using carbon nanotube network field-effect transistors," *Proc. Nat'l. Acad. Sci. USA.*, 103(4):921-926.

Stetter et al., (Feb. 23, 2003) "Nano-Electronic Sensors; Practical Device Designs for Sensors", *Nanotechnology Conference and Trade Show, Nanotech, Joint Meeting, International Conference on Modeling and Simulation of Microsystems, MSM, International Conference on Computational Nanoscience and Technology*, 3(23):313-316.

Suri et al., (2002) "Gas and Humidity Sensors Based on Iron Oxide-Polypyrrole Nanocomposites", *Sensors and Actuators*, B81:277-282.

Wilson L. J. (Dec. 1, 2005) "New carbon nanostructures for imaging and therapy of breast cancer," *Breast Cancer Research and Treatment, Kluwer Academic Publishers*, BO, 94(1):S1-S301,, MS1-1, XP019274939, ISSN:1573-7217.

US Office Action dated Mar. 17, 2009 issued in U.S. Appl. No. 11/588,845.

US Office Action dated Oct. 7, 2010 issued in U.S. Appl. No. 12/560,316.

US Final Office Action dated Jun. 28, 2011 issued in U.S. Appl. No. 12/560,316.

US Office Action dated May 21, 2014 issued in U.S. Appl. No. 12/560,316.

US Office Action dated Oct. 29, 2008 issued in U.S. Appl. No. 11/259,414.

US Final Office Action Apr. 28, 2009 in U.S. Appl. No. 11/259,414.

US Office Action dated Dec. 28, 2009 in U.S. Appl. No. 12/607,912.

Kietis et al. (2001), "Electrical-to-mechanical coupling in purple membranes: membrane as electrosrictive medium." *Biophysical Jrnl*, vol. 80, pp. 1631-1640.

\* cited by examiner

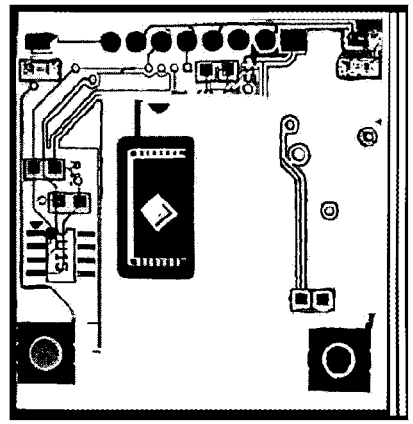
Fig. 1A
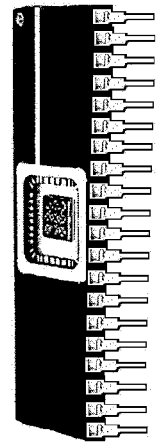
Fig. 1B (views a, b and c)
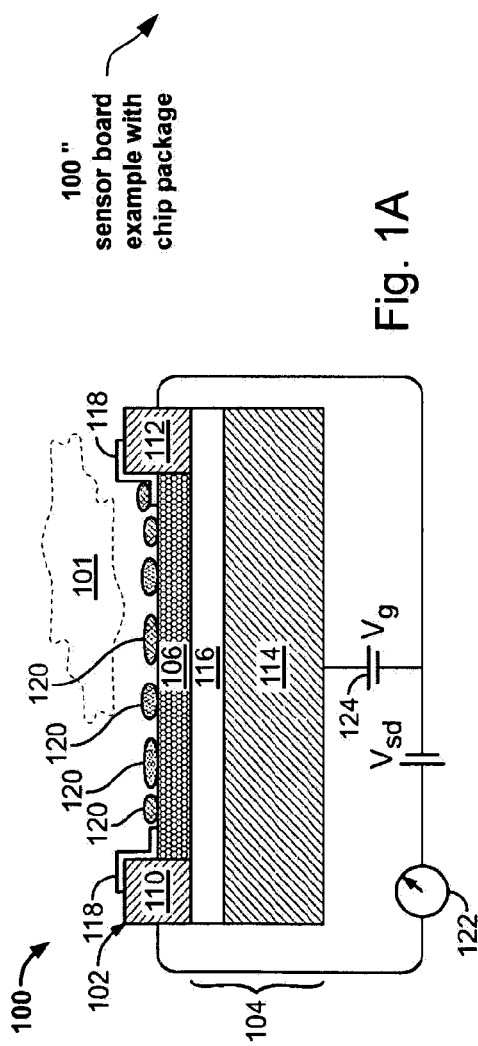
100" sensor board example with chip package
Fig. 1D
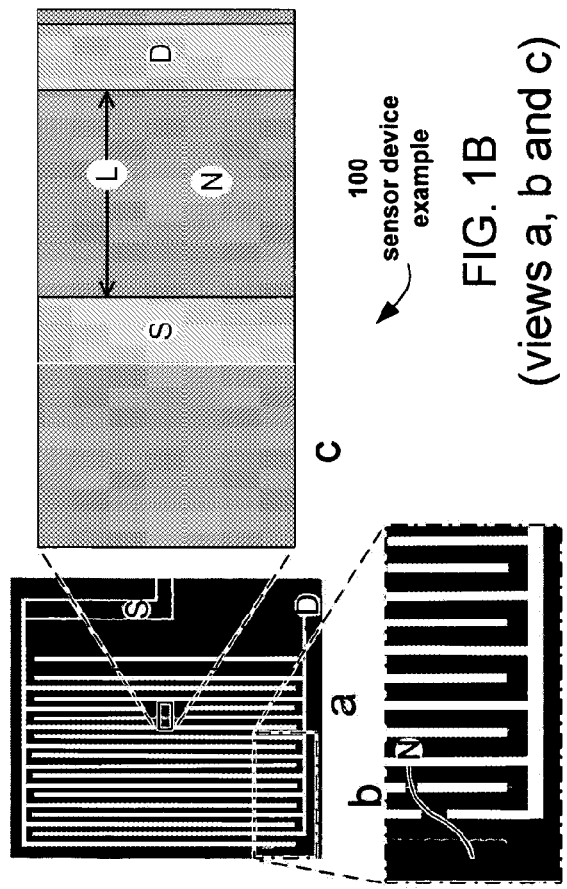
100' packaged sensor chip example
Fig. 1C Fig. 4A
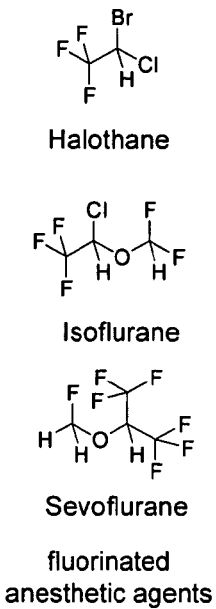
Halothane
Isoflurane
Sevoflurane
fluorinated
anesthetic agents
Fig. 4B
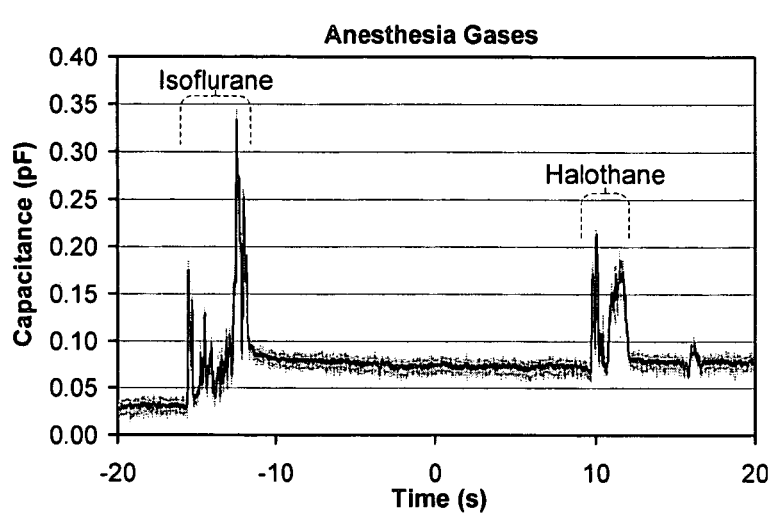
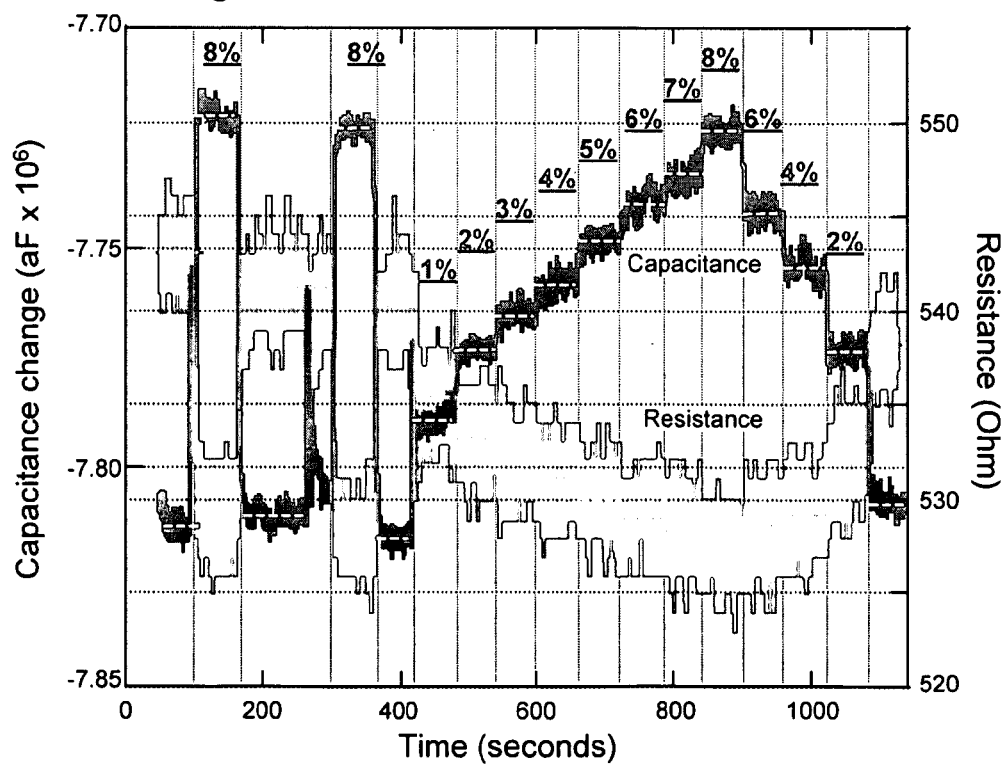

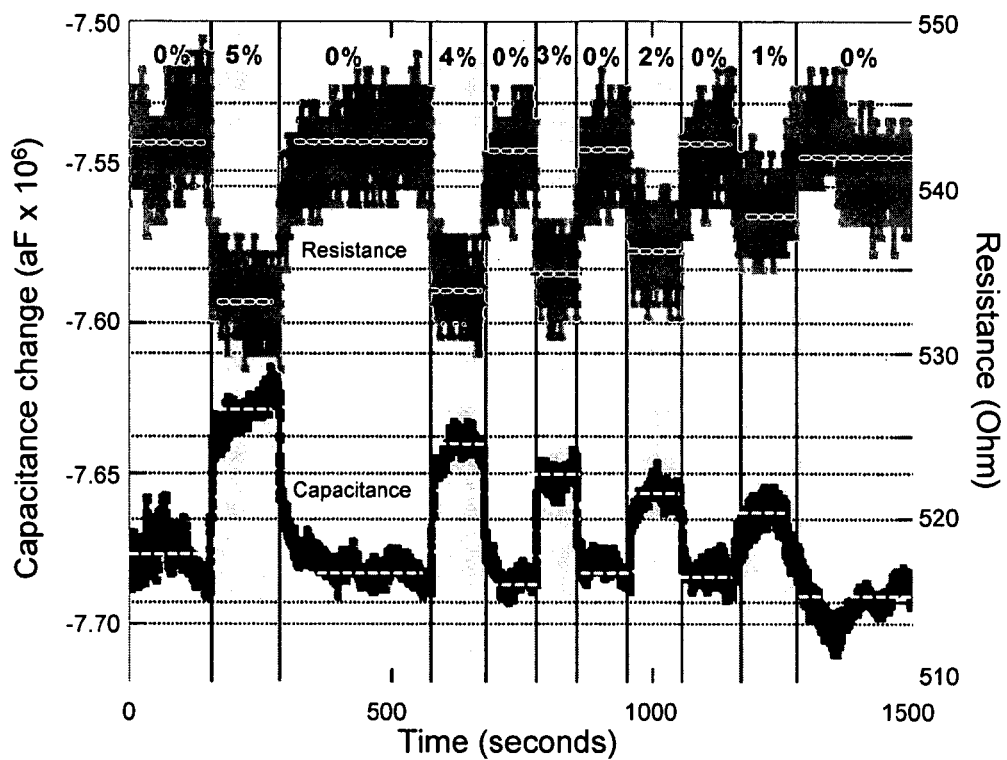
Fig. 5B - Isoflurane (capcitance & resistance)
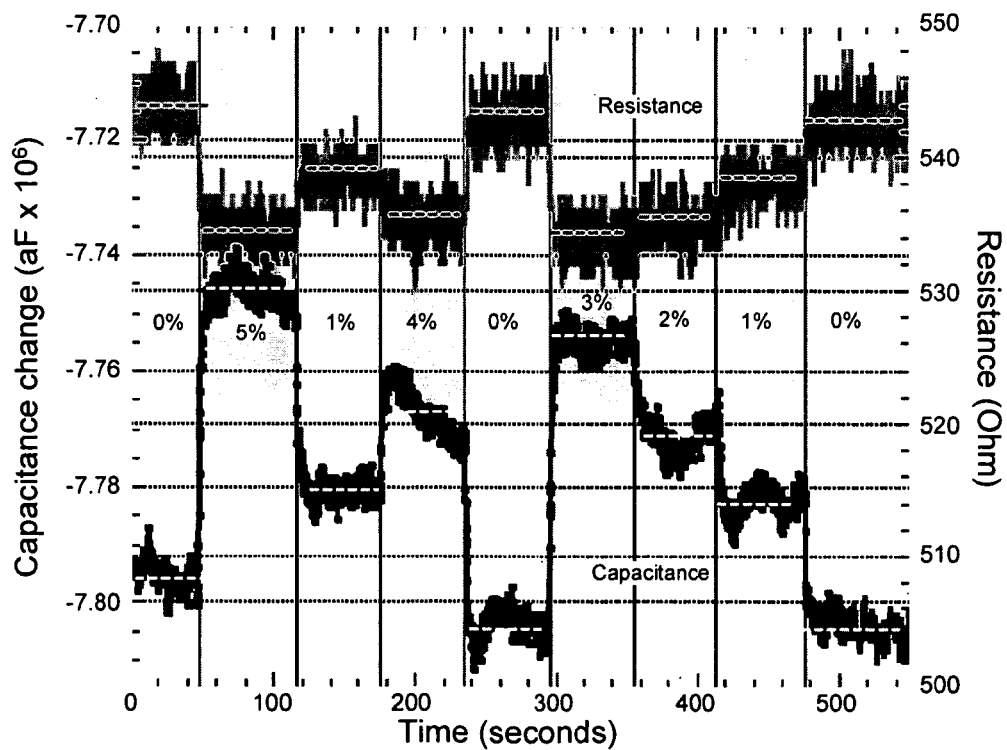
Fig. 5C - Halothane (capcitance & resistance)

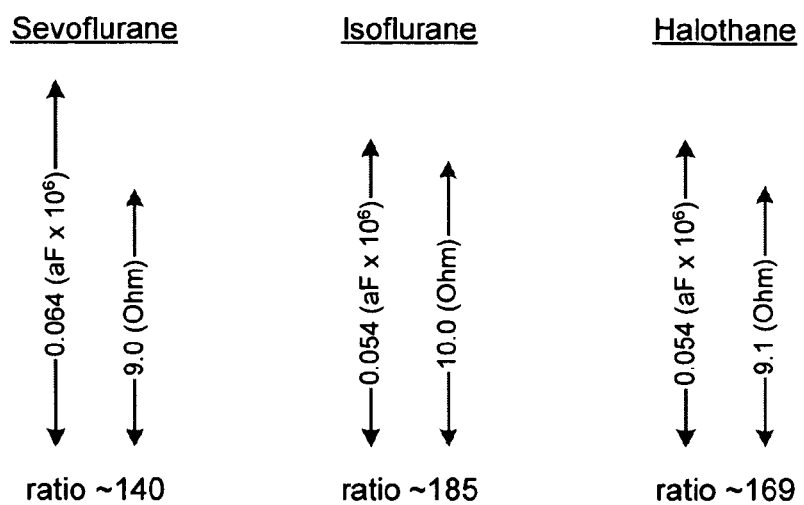
Fig. 5D
relative ratios of change of resistance and capacitance for 5% concentration of agent in air
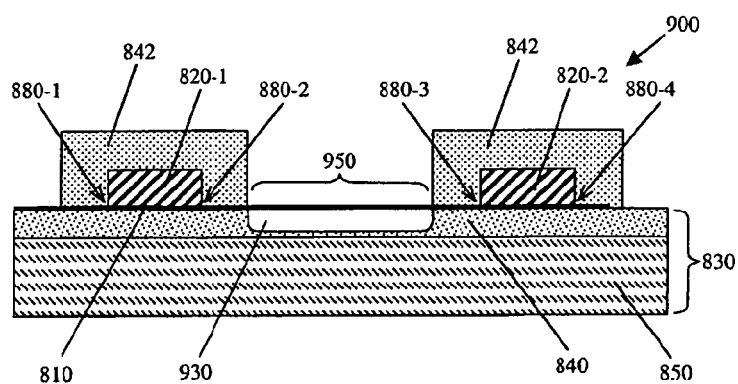
Fig. 6
Fig. 9 of
US 6,894,359

Whatman Anopore® 20 nm

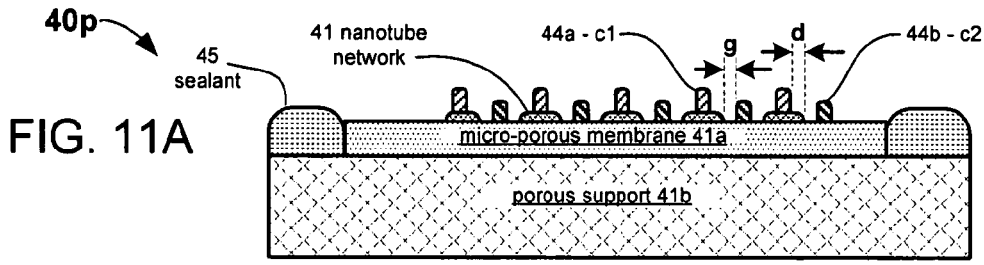

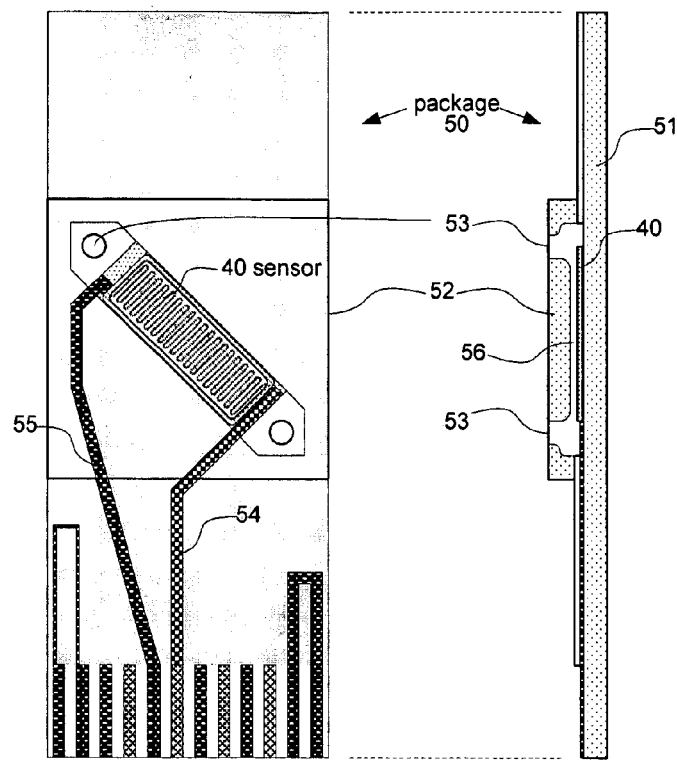
Fig. 16 - disposable capillary package
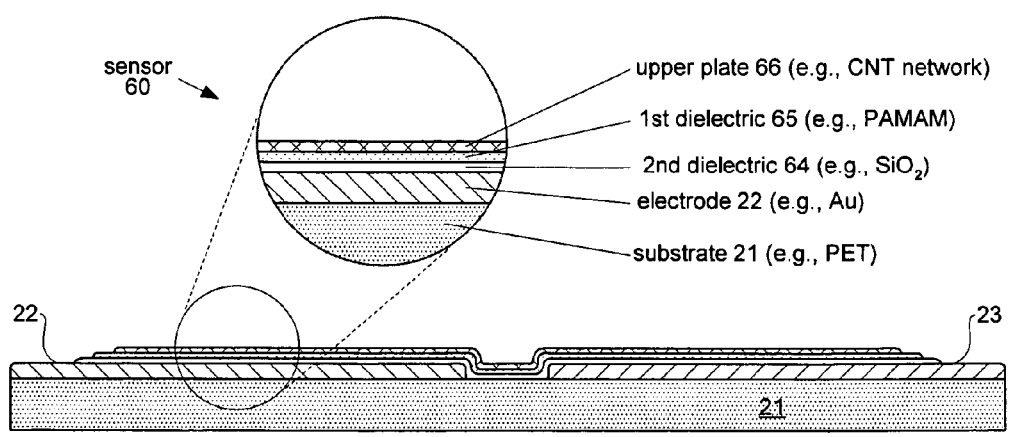
Fig. 17 - multilayer dielectric Fig. 20
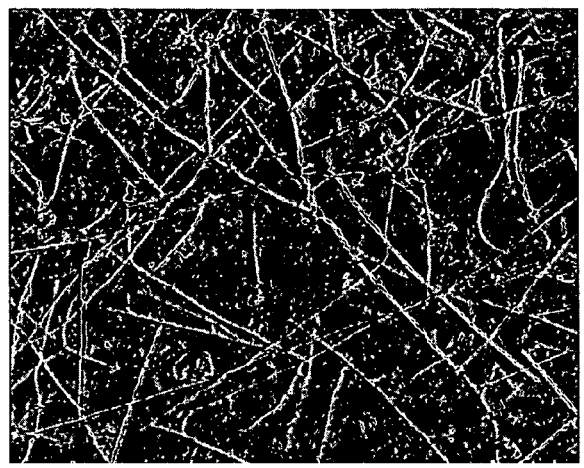
Fig. 21
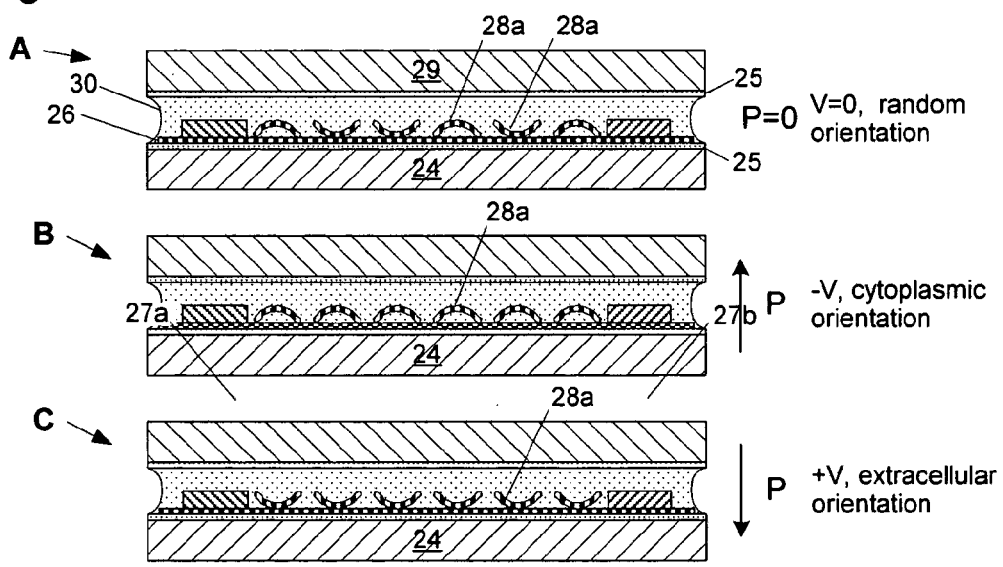
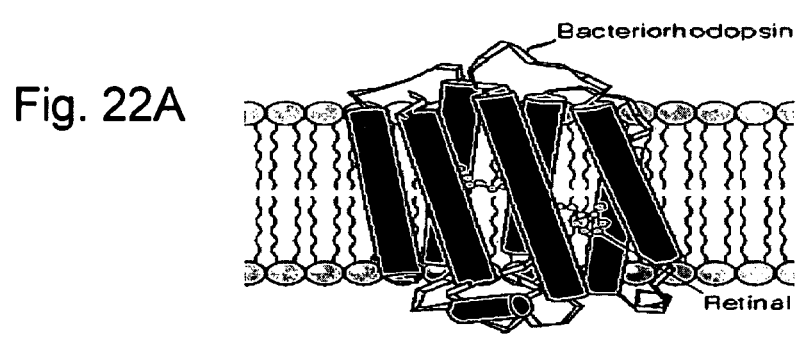
Fig. 22A 2r 6.2 nm 2r = 2 nm

NANO-ELECTRONIC SENSORS FOR CHEMICAL AND BIOLOGICAL ANALYTES, INCLUDING CAPACITANCE AND BIO-MEMBRANE DEVICES

CROSS-REFERENCE TO RELATED APPLICATIONS

This application is a continuation-in-part of co-pending U.S. patent application Ser. No. 11/090,550 filed Mar. 25, 2005 entitled "Sensitivity control for nanotube sensors", which is a divisional application of U.S. patent application Ser. No. 10/280,265 filed Oct. 26, 2002 (now U.S. Pat. No. 6,894,359), which in turn claims priority to U.S. Provisional Application No. 60/408,412 filed Sep. 4, 2002, which applications are incorporated by reference.

This application is a continuation-in-part of co-pending U.S. patent application Ser. No. 10/345,783 filed Jan. 16, 2003, entitled "Electronic sensing of biological and chemical agents using functionalized nanostructures" (now published as 2003-0134433), which claims priority to U.S. Provisional Application No. 60/349,670 filed Jan. 16, 2002, which applications are incorporated by reference.

This application is a continuation-in-part of co-pending U.S. patent application Ser. No. 10/704,066 filed Nov. 7, 2003 entitled "Nanotube-Based Electronic Detection Of Biomolecules" (published as US 2004-0132070 on Jul. 8, 2004), which claims priority to U.S. Provisional Application No. 60/424,892 filed Nov. 8, 2002, which applications are incorporated by reference.

This application is a continuation-in-part of co-pending U.S. patent application Ser. No. 11/318,354 filed Dec. 23, 2005, entitled "Nanoelectronic Sensor Devices For DNA Detection", which claims priority to (among other applications) U.S. Provisional Application Nos. 60/748,834 filed Dec. 9, 2005; 60/738,694 filed Nov. 21, 2005; 60/730,905, filed Oct. 27, 2005; 60/668,879 filed Apr. 5, 2005; 60/657,275 filed Feb. 28, 2005; and 60/639,954, filed Dec. 28, 2004, which applications are incorporated by reference.

This application claims priority to the following U.S. Provisional Application. Nos. 60/660,441, filed Mar. 10, 2005, entitled "Integrated Systems Including Cell Membranes and Nanoelectronic Devices"; 60/668,879, filed Apr. 5, 2005, entitled "Nanoelectronic System For Virus Detection and Identification"; 60/669,126, filed Apr. 6, 2005, entitled "Systems Having Integrated Cell Membranes And Nanoelectronics Devices, And Nano-Capacitive Biomolecule Sensors; 60/683,460, filed May 19, 2005, entitled "Multi-Valent Breath Analyzer having nanoelectronic sensors, and it use in Asthma monitoring"; 60/730,905 filed Oct. 27, 2005, entitled "Nanoelectronic Sensors And Analyzer System For Monitoring Anesthesia Agents And Carbon Dioxide In Breath"; and 60/773,138, filed Feb. 13, 2006 entitled "Nanoelectronic Capacitance Sensors For Monitoring Analytes," which applications are each incorporated by reference.

BACKGROUND

1. Field of the Invention

The present invention relates to nanoelectronic devices, and in particular to nanostructured sensor systems for measurement of analytes, for example by measurement of variations of capacitance, impedance or other electrical properties of nanostructure elements in response to an analyte.

2. Description of Related Art

Nanowires and nanotubes, by virtue of their small size, large surface area, and near one-dimensionality of electronic transport, are promising candidates for electronic detection of chemical and biological species. Field effect transistors ("FET") fabricated from component semiconducting single wall carbon nanotubes ("NT") have been studied extensively for their potential as sensors. A number of properties of these devices have been identified, and different mechanisms have been proposed to describe their sensing behavior. Devices that incorporate carbon nanotubes have been found to be sensitive to various gases, such as oxygen and ammonia, and these observations have confirmed the notion that such devices can operate as sensitive chemical sensors.

Nanotubes were first reported in 1993 by S. Iijima and have been the subject of intense research since. Single walled nanotubes ("SWNT") are characterized by strong covalent bonding, a unique one-dimensional structure, and exceptionally high tensile strength, high resilience, metallic to semiconducting electronic properties, high current carrying capacity, and extreme sensitivity to perturbations caused by charged species in proximity to the nanotube surface.

SWNT devices, including FETs and resistors, can be fabricated using nanotubes grown on silicon or other substrates by chemical vapor deposition from iron-containing catalyst nanoparticles with methane/hydrogen gas mixture at 900 degrees C. Other catalyst materials and gas mixtures can be used to grow nanotubes on substrates, and other electrode materials and nanostructure configurations and have been described previously by Gabriel et al. in U.S. patent application Ser. No. 10/099,664 and in U.S. patent application Ser. No. 10/177,929, both of which are incorporated by reference herein. Currently, technology for constructing practical nanostructure devices is in its infancy. While nanotube structures show promise for use as sensor devices and transistors, current technology is limited in many ways.

For example, it is desirable to take advantage of the small size and sensitivity of nanotube and other nanostructure sensors to sense biological molecules, such as proteins. But a useful sensor of this type should selectively and reliably respond to a molecular target of a specific type. For example, it may be desirable to selectively sense a specific protein, while not responding to the presence of other proteins in the sample. Examples of covalent chemical attachment of biological molecules to nanotubes, including proteins and DNA, are known in the art, although it has not been convincingly demonstrated that useful detection of specific proteins or other large biomolecules can be accomplished in this way. For one thing, covalent chemical attachment has the disadvantage of impairing physical properties of carbon nanotubes, making structures of this type less useful as practical sensors. In addition, carbon nanotubes are hydrophobic, and generally non-selective in reacting with biomolecules.

It is desirable, therefore, to provide a nanotube sensing device that is biocompatible and exhibits a high degree of selectivity to particular targets. As described in commonly assigned patents and applications incorporated by reference herein, nanoelectronic sensors having active elements comprising nanostructures offer salient advantages for analyte detection for a wide scope of applications, including industrial, medical and biomolecular sensing.

SUMMARY OF THE INVENTION

Nanoelectronic sensors having aspects of the invention, such as nanotube-based capacitance and transistor devices, provide a device to inexpensively identify and measure concentrations of analytes, such as analysis of species and analytes in patients' breath.

A preferred nanostructure for employment in nanoelectronic sensors is the carbon nanotube. The nanoelectronic sensors provide a large sensing surface in a tiny, low-power package which can directly sample and selectively monitor analyte concentrations. A single sensor chip may include a plurality of sensors, for example, capable of measuring multiple analytes. Much of the signal processing may be built into the sensor board, requiring only simple and inexpensive external instrumentation for display and data logging, so as to provide a fully calibrated, sterilized, packaged sensor. The small size of the nanoelectronic sensors permit them to fit directly in otherwise difficult sampling environments. Embodiments of nanoelectronic sensors having aspects of the invention may be employed for monitoring and detection of many species of analytes.

Alternative embodiments having aspects of the invention include systems configured to include multiplexed assays on a single sensor platform or chip, microprocessors and/or wireless transceivers. Because the output is digital, electronic filtering and post-processing methods may be used to eliminate extraneous noise, as desired. See, for example, U.S. patent application Ser. No. 11/111,121 filed Apr. 20, 2005 entitled "Remotely communicating, battery-powered nanostructure sensor devices," which is incorporated by reference.

Alternative embodiments having aspects of the invention are configured for detection of analytes employing nanostructured sensor elements configured as one or more alternative types of electronic devices, such as capacitive sensors, resistive sensors, impedance sensors, field effect transistor sensors, and the like, or combinations thereof. Two or more such measurement strategies may be included in a sensor device so as to provide orthogonal measurements that increase accuracy and/or sensitivity. Alternative embodiments have functionalization groups or material associated with the nanostructured element so as to provide sensitive, selective analyte response.

Although in the description herein a number of exemplary sensor embodiments are based on one or more carbon nanotubes, it is understood that other nanostructures known in the art may also be employed, e.g., semiconductor nanowires, various form of fullerenes, multiwall nanotubes, and the like, or combinations thereof. Elements based on nanostructures such carbon nanotubes (CNT) have been described for their unique electrical characteristics. Moreover, their sensitivity to environmental changes (charged molecules) can modulate the surface energies of the CNT and be used as a detector. The modulation of the CNT characteristics can be investigated electrically by building devices that incorporate the CNT (or CNT network) as an element of the device. This can be done as a conductive transistor element or as a capacitive gate effect.

Certain exemplary embodiments having aspects of the invention include single-walled carbon nanotubes (SWNTs) as semiconducting or conducting elements. Such elements may comprise single or pluralities of discrete parallel NTs, e.g., in contact or electrically communicating with a device electrode. For many applications, however, it is advantageous to employ semiconducting or conducting elements comprising a generally planar network region of nanotubes (or other nanostructures) substantially randomly distributed adjacent a substrate, conductivity being maintained by interconnections between nanotubes.

Particular embodiments of capacitive sensor having aspects of the invention provide an architecture in which there is no direct contact of a nanostructured capacitive plate with external electrodes, providing the advantages of extremely low parasitic capacitance and the avoidance of Schotky barriers at metal-nanostructure contacts.

Exemplary embodiments of sensor devices having aspects of the invention provide for detection of chemical species employing nanostructures as elements of capacitive components, both for use in gaseous and in liquid media, such as biological fluids, electrolytes, and the like. Real time electronic detection and monitoring and offers high sensitivity, is rapid and reversible, and has a large dynamic range. Because the output is digital, electronic filtering and post-processing may be used to eliminate extraneous noise, as desired. Certain embodiments include multiplexed assays on a single sensor platform or chip.

Alternative embodiments having aspects of the invention are configured for detection of such biomolecules and biological complexes, such as polynucleotides, (such as DNA, RNA and the like), proteins, (such as enzymes), other biopolymers, cytokines, co-factors, hormones, cell or viral fragments, surface receptor groups, antibodies, and the like. Certain embodiments use nanotube capacitance measurements to detect electrical effects due to biological interactions between biomolecules, such as DNA hybridization, enzyme-substrate interaction, antibody-antigen binding, receptor-ligand binding, and the like.

In capacitive sensing embodiments, the system measures analyte polarizability and its effect on the surface dielectric. Nanotubes have advantages for capacitive sensing because their small size generates high field strengths ($10^8$V/cm) that are not possible with conventional planar devices.

Sensor detection method embodiments having aspects of the invention include other types of nanoelectronic sensors used in conjunction or in integration with capacitive nanosensors, such as functionalized nanotube resistors, nanotube field effect transistors (NTFET), electrochemical impedance measurements, and the like. The inclusion of two or more such measurement strategies may be included to provide orthogonal measurements that increase accuracy.

Sensor detection method embodiments having aspects of the invention also may include detection or signal enhancers (and separation or concentration mechanisms), include electronic, physical and chemical stringency parameters, magnetic bead mediated nanotube strain modulation or other external forces to amplify signal transduction. Implemented with a lock-in amplifier, phased detection may be included significantly enhance sensitivity and accuracy.

Additional embodiments having aspects of the invention include the integration of biological processes and molecules with nanoscale fabricated structures (nanobioelectronics), and provide a technology suitable for electronic control and sensing of biological systems.

NT Network Capacitive Embodiments

The exemplary nanoelectronic devices having aspects of the invention include a nanotube-based capacitance device, e.g., a sensor, in addition to including a biological component generally similar to that described. Although in the description that follows, the exemplary embodiments are based on one or more carbon nanotubes, it is understood that other nanostructures known in the art may also be employed. Elements based on nanostructures such carbon nanotubes (CNT) have been described for their unique electrical characteristics. Moreover, their sensitivity to environmental changes (charged molecules) can modulate the surface energies of the CNT and be used as a detector. The modulation of the CNT characteristics can be investigated electrically by building devices that incorporate the CNT (or CNT network) as an element of the device. This can be done as a conductive transistor element or as a capacitive gate effect.

Certain exemplary embodiments having aspects of the invention include SWNTs as semiconducting or conducting elements. Such elements may comprise single or pluralities of discrete parallel NTs, e.g., in contact or electrically communicating with a device electrode. For many applications, however, it is advantageous to employ semiconducting or conducting elements comprising a generally planar network region of nanotubes (or other nanostructures) substantially randomly distributed adjacent a substrate, conductivity being maintained by interconnections between nanotubes.

Devices fabricated from random networks of SWNTs eliminates the problems of nanotube alignment and assembly, and conductivity variations, while maintaining the sensitivity of individual nanotubes For example, such devices are suitable for large-quantity fabrication on currently on 4-inch silicon wafers, each containing more than 20,000 active devices. These devices can be decorated with specific recognition layers to act as a transducer for the presence of the target analyte. Such networks may be made using chemical vapor deposition ("CVD") and traditional lithography, by solvent suspension deposition, vacuum deposition, and the like. See for example, U.S. patent application Ser. No. 10/177,929 entitled "Dispersed Growth of Nanotubes on a Substrate" and U.S. patent application Ser. No. 10/280,265 entitled "Sensitivity Control for Nanotube Sensors" U.S. patent application Ser. No. 10/846,072 entitled "Flexible Nanotube Transistors"; and L. Hu et al., *Percolation in Transparent and Conducting Carbon Nanotube Networks*, Nano Letters (2004), 4, 12, 2513-17, each of which is incorporated herein by reference.

The nanoscale elements can be fabricated into arrays of devices on a single chip for multiplex and multiparametric applications See for example, U.S. patent application Ser. No. 10/388,701 entitled "Modification of Selectivity for Sensing for Nanostructure Device Arrays"; U.S. patent application Ser. No. 10/656,898 entitled "Polymer Recognition Layers for Nanostructure Sensor Devices", U.S. patent application Ser. No. 10/940,324 entitled "Carbon Dioxide Nanoelectronic Sensor"; and U.S. Provisional Patent Application No. 60/564,248 entitled "Remotely Communicating, Battery-Powered Nanostructure Sensor Devices"; each of which is incorporated herein by reference.

In contrast to resistive or transconductance measurements that monitor charge transfer and charge mobility, capacitance measures the polarizability of the analyte molecules on the nanotubes. The surface capacitance effect is caused by the large electric field gradient radiating from the nanotubes. SWNTs are about 1-2 nm in diameter; field gradients of $10^8$V/cm can be generated, which is impossible in conventional electrode geometries (See Snow et al., "*Chemical Detection with a Single-Walled Carbon Nanotube Capacitor*", Science (2005) 307: 1942-1945, which is incorporated herein by reference).

Capacitive sensing may exploit the principle that binding events tend to change the thickness or dielectric properties of the recognition layer, and is therefore dependent on the functionalization of nanotubes. Preferably this layer is very thin and electrically insulating to improve the ratio between capacitance and Faradaic currents. Analyte polarizability can be modulated by peak-peak voltage and the AC frequency providing a two-dimensional image of the analyte for better sensitivity and accuracy. Bode plots may provide the frequency dependence of impedance magnitude and phase angle. Data may be plotted as differential capacitance as a function of time. Capacitance measurements do not require a conduction path and are therefore are flexible in terms of functionalization chemistries.

A CNT network may be included in a capacitive electrode. In an active device, such as a sensor for the detection for bio-analytes, a capacitive electrode may be interrogated with an AC signal. Preferably, a CNT network is integrated with metal electrodes. A CNT network may be included as first "plate" of a capacitor. A metal electrode may be included as a second plate of a capacitor, and (or both "plates" may include nanostructure elements). Functionalization on this structure (either on the metal plate, on the CNT network, or on other adjacent elements) allows the biochemical attachment of bio-analytes. See for example, U.S. patent application Ser. No. 10/345,783 entitled "Electronic Sensing of Biological and Chemical Agents Using Functionalized Nanostructures"; and U.S. patent application Ser. No. 10/704,066 entitled "Nanotube-Based Electronic Detection of Biomolecules", each of which is incorporated herein by reference.

The second plate of the capacitor may include metallic surface that is separated from the first plate through some dielectric (could be material, liquid or gas, such as air). Presence or absence of bioanalytes on the capacitor plate will change the impedance of the structure and can be detected by external measurement equipment. Measurement of capacitance is a well known technique in medical and diagnostic devices. Low cost electronic acquisition chips exist to quantify the change in capacitance (e.g., chips made by Analog Devices, among others).

The change in capacitance can be affected by the dipole moment of the molecules in contact with the capacitor. In addition, large dipole molecules can be included in the system that specifically bind to the analyte of interest (sandwich assay) to further enhance the signal of the detection.

BRIEF DESCRIPTION OF THE DRAWINGS

The following is a list which summarizes the drawings and figures herein:

FIG. 1A is a cross-sectional diagram which illustrates an exemplary electronic sensing device for detecting an analyte, configured in this example as a NTFET.

FIG. 1B are three views of a photomicrograph (SEM) of a sensor generally similar to that of FIG. 1A, view (a) showing the layout of interdigitated source and drain contacts S, D, view (b) showing an enlarged detail of a nanotube network N and the contacts S, D, and view (c) showing an enlarged detail of the margin of network N.

FIG. 1C is a photograph of a sensor generally similar to that of FIGS. 1A and 1B, fabricated on a die of a wafer, and mounted as a chip in a conventional CERDIP package.

FIG. 1D is a photograph of a sensor generally similar to that of FIGS. 1A and 1B, packaged in the manner shown in FIG. 1C, and installed on an exemplary circuit board of an electronic sensor system.

FIG. 4A is a series of the molecular diagrams of medically important fluorinated organic anesthetic agents.

FIG. 4B is plot showing the response of a device generally similar to that of FIG. 3 to brief sequential impingement of gas analyte samples (in air) containing first isoflurane and second halothane.

FIGS. 5A-5C are plots showing the responses of both capacitance and resistance signals of a device generally similar to those of FIGS. 1A and 3 to sequential samples of a selected anesthetic agent gas in air, through a graded series of concentrations, in which:

FIG. 5A shows the response to samples sevoflurane in air;

FIG. 5B shows the response to samples isoflurane in air;

FIG. 5C shows the response to samples halothane in air;

FIG. 5D graphically illustrates the relative ratios of change of resistance and capacitance for 5% concentration of each agent in air, as depicted in FIGS. 5A-C.

FIG. 6 is a cross-sectional diagram of a nanotube-based sensor as described in commonly assigned U.S. Pat. No. 6,894,359, which is incorporated by reference (FIG. 9 thereof), and having a conduit or trench providing for the flow of an analyte medium in a space between the nanotube-based element and the gate or counter electrode.

FIGS. 11A-11D are diagrams showing alternative exemplary embodiments of nanosensors having aspects of the invention and providing for flow of analyte medium through a porous substrate, in which:

FIG. 11A is a is a cross-sectional diagram of a nanosensor embodiment similar in a number of respects to the capacitive sensor shown in FIG. 9, and having a porous substrate;

FIG. 11B is a is a cross-sectional diagram of a nanosensor embodiment similar in a number of respects to the NTFET sensor shown in FIG. 1A, and having a porous substrate; and FIGS. 11C and 11D are two orthogonal cross-sectional diagrams of an exemplary flow-though micro-fluidic sensor module providing for the conduct of a gaseous or liquid analyte medium, and including one or more sensor devices disposed on porous substrates, such as the sensors depicted in FIGS. 11A and 11B.

FIG. 16 is a plan view and cross-sectional view of an exemplary disposable capillary fluidic package having aspects of the invention supporting a nanosensor embodiment.

FIG. 17 is a cross-sectional view and a magnified portion of an exemplary capacitive nanosensor embodiment having aspects of the invention, generally similar to that shown in FIG. 18 and having a multi-layer dielectric structure.

FIG. 20 is an atomic force microscopy (AFM) amplitude signal image of a random nanotube network grown by CVD on a $SiO_2$-coated silicon substrate.

FIG. 21, views A, B and C schematically illustrates an exemplary device in three orientation cases of the cell membranes: mixed orientation, cytoplasmic side attached, extracellular side attached.

FIG. 22A shows a model of the cell membrane.

DESCRIPTION OF PREFERRED EMBODIMENTS

Exemplary Nanosensor Architecture

Figure 2:
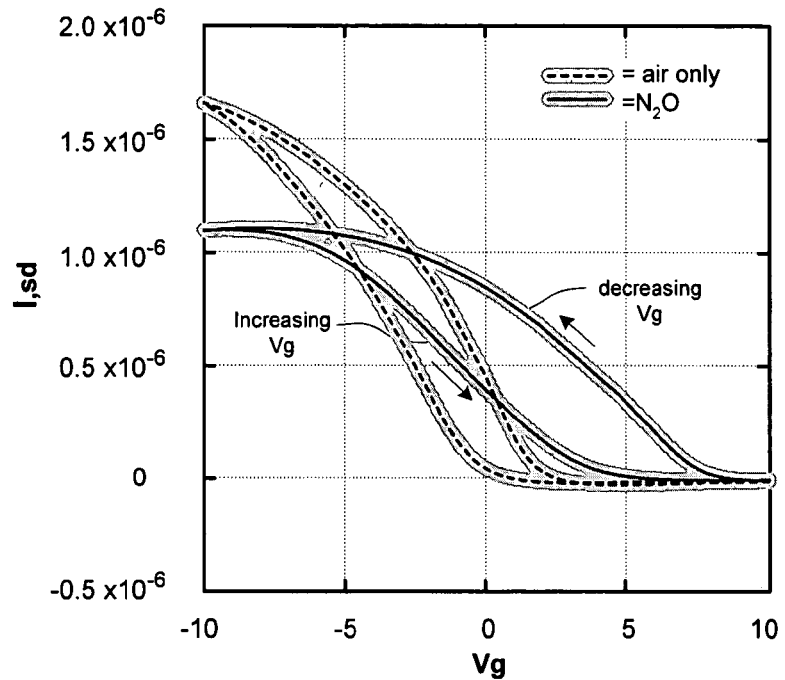
FIG. 2 is plot showing the response in the channel current signal of a device generally similar to that of FIG. 1A to air only, and to a mixture of nitrous oxide ($N_2O$) in air.

FIG. 1A shows an exemplary electronic sensing device 100 having aspects of the invention, for detecting an analyte 101, comprising a nanostructure sensor 102. Sensor 102 comprises a substrate 104, and a conducting channel or layer 106 comprising a nanostructure material, such as a nanotube or network of nanotubes, disposed on the substrate. The nanostructure material 106 may contact the substrate as shown, or in the alternative, may be spaced a distance away from the substrate, with or without a layer of intervening material.

In an embodiment of the invention, conducting channel 106 may comprise one or more carbon nanotubes. For example, conducting channel 106 may comprise a plurality of nanotubes forming a mesh, film or network. Certain exemplary embodiments having aspects of the invention include nanostructure elements which may be made using chemical vapor deposition (CVD) and traditional lithography, or may be deposited by other methods, such as solvent suspension deposition, AFM manipulation, and the like. Certain embodiments include one or more discrete nanotubes in electrical contact with one or more metal electrodes. A number of different arrangements of active nanostructures may be included without departing from the spirit of the invention.

One or more conductive elements or contacts (two are shown, 110, 112) may be disposed over the substrate and electrically connected to conducting channel 106 comprising a nanostructure material. The conductive elements permit electrical charge and/or current to be applied to the nanostructured material of channel 106, and may be used in the measurement of an electrical property of the channel 106. For example, contacts 110, 112 may comprise source and drain electrodes, respectively, permitting application of a source-drain voltage Vsd, and inducing a current in channel 106. Elements 110, 112 may comprise metal electrodes in contact with conducting channel 106. In the alternative, a conductive or semi-conducting material (not shown) may be interposed between contacts 110, 112 and conducting channel 106.

In the example of FIG. 1A, the device 100 may be operated as a gate-controlled field effect transistor, with sensor 102 further comprising a gate electrode 114. Such a device is referred to herein as a nanotube field effect transistor or NTFET. Gate 114 may comprise a base portion of substrate 104, such as a doped-silicon wafer material isolated from contacts 110, 112 and channel 106 by a dielectric layer 116, so as to permit a capacitance to be created by an applied gate voltage $V_g$. For example, the substrate 104 may comprise a silicon back gate 114, isolated by a dielectric layer 116 comprising $SiO_2$. Alternatively, the device 100 may be employed in other measurement modes. For example, device 100 may be employed as a capacitive or impedance sensor using known circuitry to create an electric field gradient between conducting channel 106 (e.g., via either of contacts 110, 112) and gate 114 and to measure the capacitance and/or impedance of this structure in relation to the influence of an analyte.

FIG. 1B includes three views of a photomicrograph (SEM) of a sensor generally similar to that of FIG. 1A, view (a) showing the layout of interdigitated source and drain contacts S,D, view (b) showing an enlarged detail of a nanotube network N and the contacts S, D, and view (c) showing an enlarged detail of the margin of network N. Note that the extent of a carbon nanotube network may be conveniently controlled by selective or masked oxidation of nanotubes from peripheral regions of the substrate ("ashing").

Returning to FIG. 1A, Sensor 102 may further comprise a layer of inhibiting or passivation material 118 covering regions adjacent to the connections between the conductive elements 110, 112 and conducting channel 106. The inhibiting material may be impermeable to at least one chemical species, such as to the analyte 101 or to environmental materials such as water or other solvents, oxygen, nitrogen, and the like. The inhibiting material 118 may comprise a passivation material as known in the art, such as silicon dioxide, aluminum oxide, silicon nitride, or other suitable material. Further details concerning the use of inhibiting materials in a NTFET are described in prior application Ser. No. 10/280,265, filed Oct. 26, 2002, entitled "Sensitivity Control For Nanotube Sensors" (now U.S. Pat. No. 6,894,359) which is incorporated by reference herein.

The conducting channel 106 (e.g., a carbon nanotube layer) may be functionalized to produce a sensitivity to one or more target analytes 101. Although nanostructures such as carbon nanotubes may respond to a target analyte through charge transfer or other interaction between the device and the analyte, more generally a specific sensitivity can be achieved by employing a recognition material 120, also called a functionalization material, that induces a measurable change in the device characteristics upon interaction with a target analyte.

Device 100 may be packaged in a conventional manner to conveniently permit connection to operating circuitry. FIG. 1C is a photograph of a sensor generally similar to that of FIGS. 1A and 1B, fabricated on a die of a wafer, and mounted as a chip in a conventional 40 pin CERDIP package using wirebonding techniques.

Device 100 may further comprise suitable circuitry in communication with sensor elements to perform electrical measurements. FIG. 1D is a photograph of a sensor generally similar to that of FIGS. 1A and 1B, packaged in the manner shown in FIG. 1C, and installed on an exemplary circuit board of an electronic sensor system. For example, a conventional power source may supply a source-drain voltage (Vsd) between contacts 110, 112. Measurements via the sensor device 100 may be carried out by circuitry represented schematically by meter 122 connected between contacts 110, 112. In embodiments including a gate electrode 114, a conventional power source 124 may be connected to provide a selected or controllable gate voltage (Vg). Device 100 may include one or more electrical supplies and/or a signal control and processing unit (not shown) as known in the art, in communication with the sensor 102.

FIG. 2 is plot showing response in the channel current signal relative to variable gate voltage, of a device generally similar to that of FIG. 1A, upon exposure to air only, and to concentrated nitrous oxide ($N_2O$). The nanotube network was functionalized with spin-coated polyimide. The exposure to $N_2O$ produces a marked decrease in maximum current ("on" current), and also shifts the threshold Vg to a higher voltage (curve shift to the right). Thus it may be seen that the NTFET provides a sensitive and specific measurement for $N_2O$.

Particular Nanosensor Elements

Substrate.

The substrate 104 may be insulating, or on the alternative, may comprise a layered structure, having a base 114 and a separate dielectric layer 116 disposed to isolate the contacts 110, 112 and channel 106 from the substrate base 114. The substrate 104 may comprise a rigid or flexible material, which may be conducting, semiconducting or dielectric. Substrate 104 may comprise a monolithic structure, or a multilayer or other composite structure having constituents of different properties and compositions.

Wafer Substrate.

Suitable substrate materials may include quartz, alumina, polycrystalline silicon, III-V semiconductor compounds, and other suitable materials. Substrate materials may be selected to have particular useful properties, such as transparency, microporosity, magnetic properties, monocrystalline properties, polycrystalline or amorphous properties, or various combinations of these and other desired properties. For example, in an embodiment of the invention, the substrate 104 may comprise a silicon wafer doped so as to function as a back gate electrode 114.

A diffusion barrier (e.g., a deposited layer of $Si_3N_4$) may be included at or adjacent the substrate surface. The barrier can prevent contamination of a substrate (such as a doped silicon wafer) such as by metallic catalysts or other substances introduced during fabrication steps. Similarly, a surface conditioning top layer (such as a nano-smooth layer of $SiO_2$) may be included, so as to promote nanotube CVD growth, and/or to provide a smooth surface for nanotube network deposition. For further description, see commonly invented and assigned U.S. Provisional Application No. 60/652,883, filed Feb. 15, 2005, entitled "Nanoelectric Sensor System and Hydrogen-Sensitive Functionalization", which is incorporated by reference.

Alternative Flexible Substrate.

In certain alternative embodiments, the substrate may comprise a flexible insulating polymer, optionally having an underlying gate conductor (such as a flexible conductive polymer composition), as described in application Ser. No. 10/846,072 filed May 14, 2004 entitled "Flexible Nanotube Transistors", the entirety of which application is incorporated herein by this reference. In certain embodiments of nanosensors having aspects of the invention, a commercially available flexible substrate with pre-patterned conductors (e.g., graphite film) may be employed. Further elements, such as a nanotube network and associated functionalization, may be deposited upon the substrate in electrical communication with the pre-patterned conductors. Such embodiments may be readily adapted to disposable sensor products, such as for home medical testing.

Alternative Porous Substrate.

In other alternative embodiments, the substrate may comprise a porous material. For example, sensor elements such as a nanotube network and contacts may be deposited on a porous material so as to permit analyte medium and/or a carrier solvent or gas to pass through the substrate. In certain embodiments, the substrate may comprise a micro-porous membrane having a pore size and density suitable for deposition of nanostructures such as SWNTs, and the microporous membrane may in turn be disposed upon a porous support material having a different pore size, density and thickness. The substrate may comprise more than one layer of microporous membrane material, for example, where it is desired to embed structures (e.g., a gate or counter electrode, thermistors, heating elements, circuit leads and the like) within the substrate. Particular materials may be selected for properties such as electrical insulation, hydrophilicity or hydrophobicity, solvent stability, protein non-binding, cell culture compatibility, and the like.

Figure 10A:
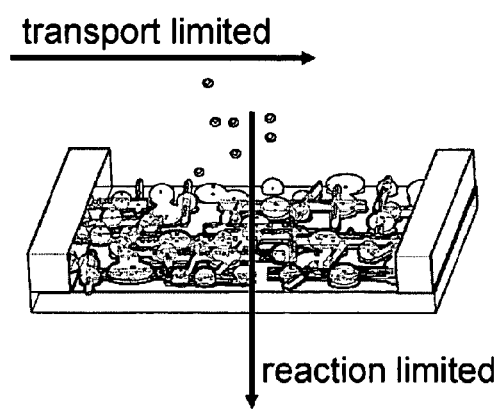
FIG. 10A is a diagram contrasting alternative configurations of a nanosensors having aspects of the invention, one providing for a transport-limited parallel or tangential flow of analyte medium with a sensor having a porous substrate and providing for a reaction-limited perpendicular or through-flow of analyte medium.
Figure 10B:
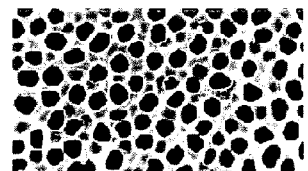
FIGS. 10B-10C are photomicrographs of two alternative micro-porous alumina membranes, such as may be employed in through-flow sensor embodiments having aspects of the invention.

The micro-porous membrane may comprise, for example, an alumina matrix with an electrochemically etched honeycomb pore structure (e.g., the Anopore® membrane, by Whatman plc of Brentford, West London, UK, see FIG. 10B). Such membranes are available commercially with substantially uniform pore diameter specification ranging from several microns to 20 nanometers or smaller, and have been made smaller as about 5 nm pore size (FIG. 18C). Membranes may be composed of high purity alumina, and exhibit hydrophilic properties, low protein binding and minimal autofluorescence. Alternatively, high-porosity track-etched polycarbonate membranes are commercially available (e.g., Nuclepore® membrane, by Whatman) with comparably small pore size (e.g. pore diameter specification ranging from several microns to smaller than about 15 nm, provided in a membrane of about 6-15 microns thickness) and suitable properties. Microporous membranes may comprise other materials, such as polyamide, PTFE, PES, and the like.

Contacts or Electrodes.

The conductor or contacts 110, 112 used for the source and drain electrodes can be any of the conventional metals used in semiconductor industry, or may be selected from Au, Pd, Pt, Cr, Ni, ITO, W or other metallic material or alloy or mixture thereof. In the alternative, the contact may comprise a multi-layer or composite of metallic materials, such as Ti+Au, Cr+Au, Ti+Pd, Cr+Pd, or the like. A multi-layer construction may help in improving the adhesion of the metal to the substrate. For example, electrical leads may be patterned on top of a nanotube network channel from titanium films 30 nm thick capped with a gold layer 120 nm thick. In the alternative, other conductive materials may be employed, such as conductive polymers, graphitic materials, and the like. The dimension of the distance between source 110 and drain 112 may be selected to achieve desired characteristics for a particular application. It should be understood that one or more of each of a source and drain electrode may be arranged in an interdigitated or spaced-apart electrode array, permitting a comparative large area of nanostructure channel 106 having a comparatively small source-drain gap to be arranged compactly.

Gate or counter electrode 114 may comprise materials generally similar to contacts 110, 112. In the alternative, the gate electrode 114 may comprise a sublayer within substrate 104. Gate electrode 114 may comprise doped silicon, patterned metal, ITO, other conductive metal or non-metal material, or combinations thereof. Alternative forms of gate electrodes may be employed, such as a top gate, a gate effected via a conducting analyte carrier medium (e.g. an aqueous solution). Optionally, a device 102 may comprise such other electrodes as a counter electrode, a reference electrode, a pseudo-reference electrode, without departing from the spirit of the invention.

Nanostructure Channel or Layer.

Exemplary embodiments having aspects of the invention include sensor devices having at least one conducting channel 106 comprising one or more nanostructures. For example, conducting channel or layer 106 may comprise one or more single-wall carbon nanotubes, multiple-wall carbon nanotubes, nanowires, nanofibers, nanorods, nanospheres, or other suitable nanostructures. In addition, or in the alternative, conducting channel or layer 106 may comprise one or more nanostructures comprised of boron, boron nitride, and carbon boron nitride, silicon, germanium, gallium nitride, zinc oxide, indium phosphide, molybdenum disulphide, silver, or other suitable materials. Various suitable methods for manufacturing nanotubes and other nanostructures are known in the art, and any suitable method may be used.

Alternative Conducting Network Layer.

In preferred embodiments having aspects of the invention, a conducting channel or nanostructure layer 106 comprises an interconnected network of smaller nanostructures disposed to form a percolation layer, mesh, or film which provides at least one electrical conduction path between a source electrode 110 and a drain electrode 112. In such a network of nanoparticles, it is not necessary that any single nanoparticle extends entirely between the source and drain contacts. In operation the conductivity of channel 106 between source electrode 110 and drain electrode 112 may be maintained by interconnections, contacts or communications between adjacent nanostructures. Such networks of nanoparticles, such as nanotubes and the like, may be configured to be defect-tolerant, in that disruption of any particular conductive path may be compensated by remaining paths within the network. In an embodiment of the invention, nanostructure conducting channel 106 comprises one or more single-walled or multi-walled carbon nanotubes. The nanotubes may be arranged as clumps or bundles, or as distinct separated fibers. A useful network of nanotubes may be provided, for example, by distributing a dispersion of nanotubes over a substrate so as to be approximately planar and randomly oriented. For example, conducting channel 106 may comprise a network including a plurality of dispersed single wall carbon nanotubes (SWCNT), in which the nanotubes are oriented substantially randomly, non-parallel and separated with respect to one another (i.e., not clumped) as an interconnecting mesh disposed generally parallel to the substrate.

Electrical characteristics of the channel 106 may be optimized to suit a particular functionalization chemistry or other constituent of the sensor which effects conductivity, or to suit a desired range of analyte concentration. In preferred embodiments, the density or thickness of a nanotube network may be varied to provide a desired degree of conductivity between the source and drain electrodes. In the alternative, or in addition, the proportion of metallic or semiconducting nanotubes in the network may be selected to achieve a desired conductivity in the network. One advantage of using a nanostructure network architecture for the conducting channel 106 is that these factors may be varied to produce a conducting network having a selected margin above (or below) the percolation limit, permitting convenient optimization of device characteristics. For example, a NT network channel may be formed to be slightly below the percolation limit for the uncoated network, and modified by deposition of a conducting recognition material, such as Pd, to result in a functionalized channel of desired conductivity. In another example, the conductivity of an initially dry network may be selected to allow for operation in association with anticipated additional conductivity of a fluid analyte medium, such as a physiologic buffer or solvent.

CVD Nanoparticle Network.

Nanostructure networks may be formed by various suitable methods. One suitable approach may comprise forming an interconnecting network of single-wall carbon nanotubes directly upon the substrate, such as by reacting vapors in the presence of a catalyst or growth promoter disposed upon the substrate. For example, single-walled nanotube networks can be grown on silicon or other substrates by chemical vapor deposition from iron-containing catalyst nanoparticles with methane/hydrogen gas mixture at about 900 deg C. The network contains many randomly oriented carbon nanotubes, which occur individually, rather than in bundles. The density of nanotubes and nanotube interconnections may adjusted so that there is a selected network conductivity or percolation level. The CVD process may advantageously use a highly dispersed catalyst or growth-promoter for nanostructures permits a network of nanotubes of controlled diameter and wall structure to be formed in a substantially random and unclumped orientation with respect to one another, distributed substantially evenly at a selected mean density over a selected portion of the substrate. The particle size distribution may be selected to promote the growth of particular nanotube characteristics, such as tube diameter, number of walls (single or multi-walled), conductivity, or other characteristics.

Other catalyst materials and gas mixtures can be used to grow nanotubes on substrates, and other electrode materials and nanostructure configurations and are disclosed in U.S. patent application Ser. No. 10/099,664, filed Mar. 15, 2002 entitled "Modification Of Selectivity For Sensing For Nanostructure Sensing Device Arrays"; and International Application No PCT/US03/19,808, filed Jun. 20, 2003, entitled "Dispersed Growth Of Nanotubes On A Substrate" and published as WO2004-040,671, both of which applications are incorporated by reference.

Solution Deposition Nanoparticle Network.

In an alternative, conducting layer 106 comprising an interconnecting network of nanostructures may be formed by deposition from a solution or suspension of nanostructures, such as a solution of dispersed carbon nanotubes. See for example, the methods described in U.S. patent application Ser. No. 10/846,072, filed May 14, 2004 entitled "Flexible Nanotube Transistors", which is incorporated by reference. Such methods as spin coating, spray deposition, dip coating and ink-jet printing may be employed to deposit the solution or suspension of nanostructures.

In certain embodiments, a micro-porous filter, membrane or substrate may be employed in deposition of a nanotube (or other nanoparticle) network channel 106 from suspension or solution. A porous substrate can accelerate deposition by removing solvent so as to minimize "clumping," and can assist in controlling deposition density. The deposition may be carried out by capillary absorption, or using suction or vacuum deposition across the porous substrate or membrane, as described in U.S. Provisional Application No. 60/639,954 filed Dec. 28, 2004 entitled "Nanotube Network-On-Top Architecture For Biosensor," and in L. Hu et al., Percolation in Transparent and Conducting Carbon Nanotube Networks, Nano Letters (2004), 4, 12, 2513-17, each of which application and publication is incorporated herein by reference. The network thus formed may be separated from the deposition membrane using a method such as membrane dissolution or transfer bonding, and included in a sensor device structure as a conducting channel (e.g., disposed on a device substrate, contact grid, or the like).

Alternatively, a nanotube (or other nanoparticle) network deposited on a micro-porous substrate may be included in a sensor device as disposed upon the deposition substrate or membrane. This arrangement simplifies processing, and has the advantage of permitting analyte media flow perpendicularly through the pores of the device substrate, as further described in commonly invented and assigned U.S. Provisional Application No. 60/669,126, filed Apr. 6, 2005, entitled "Systems Having Integrated Cell Membranes And Nanoelectronics Devices, And Nano-Capacitive Biomolecule Sensors, which is incorporated by reference.

Functionalization or Recognition Layer.

The sensor functionalization material 120 may be selected for a specific application, such as to interact with a targeted analyte 101 to cause a measurable change in electrical properties of nanosensor device 102. For example, the functionalization material 120 may cause an electron transfer to occur in the presence of analyte 101, or may influence local environment properties, such as pH and the like, so as to indirectly change device characteristics. Alternatively or additionally, the recognition material may induce electrically-measurable mechanical stresses or shape changes in the nanostructure channel 106 upon interaction with a target analyte. Sensitivity to an analyte or to multiple analytes may be provided or regulated by the association of a nanotube conducting channel 106 with an adjacent functionalization material 120. Specific examples of suitable functionalization materials are provided later in the specification. The functionalization material 120 may be disposed as a continuous or discontinuous layer on or adjacent to channel 106. Functionalization material 120 may comprise as little as a single compound, element, or molecule bonded to or adjacent to the nanostructure channel 106. In addition, or in the alternative, functionalization materials may comprise a mixture or multilayer assembly, or a complex species (e.g., including both synthetic components and naturally occurring biomaterials).

Functionalization material 120 may be selected for a wide range of alternative chemical or biomolecular analytes. Examples include functionalization specific to gas analytes of industrial or medical importance, such as carbon dioxide as disclosed in U.S. patent application Ser. No. 10/940,324 filed Sep. 13, 2004 entitled "Carbon Dioxide Nanoelectronic Sensor", which is incorporated herein by reference. See also U.S. patent application Ser. No. 10/656,898 referenced hereinabove. Examples of functionalization materials specific to biomolecules, organisms, cell surface groups, biochemical species, and the like are disclosed in application Ser. No. 10/345,783, filed Jan. 16, 2003, entitled "Electronic Sensing Of Biological And Chemical Agents Using Functionalized Nanostructures" (now published as US 2003-0134433), and in U.S. patent application Ser. No. 10/704,066 referenced hereinabove, both of which applications are incorporated herein by reference. Further examples and more detailed disclosures regarding functionalization materials are disclosed in U.S. patent application Ser. No. 10/388,701, filed Mar. 14, 2003 entitled "Modification Of Selectivity For Sensing For Nanostructure Device Arrays" (published as US 2003-0175161), and in U.S. Patent Application Ser. No. 60/604,293, filed Nov. 19, 2004, entitled "Nanotube Sensor Devices For DNA Detection", which applications are incorporated herein by reference. Functionalization material 120 and other sensor elements may be selected to suit various physical forms of sample media, such as gaseous or liquid analyte media. See, for example, U.S. patent application Ser. No. 10/773,631, filed Feb. 6, 2004 entitled "Analyte Detection In Liquids With Carbon Nanotube Field Effect Transmission Devices", and application Ser. No. 60/604,293, filed Nov. 13, 2004, entitled "Nanotube Based Glucose Sensing," both of which applications are incorporated herein by reference.

Other Device Elements.

Optionally, a nanosensor device having aspects of the invention may include integrated temperature control elements. Temperature control may be used to control sensor sensitivity, selectivity, and/or recovery time. Thermal control may also be used to carry out analyte-related processes, such as polynucleotide hybridization and denaturization, stringency conditions, PCR, biomolecule conformation changes and the like.

For example, a nanosensor may include ohmic thermal regulation of the nanotubes of the channel, as described in U.S. patent application Ser. No. 10/655,529 filed Sep. 4, 2003 entitled "Improved Sensor Device With Heated Nanostructure", which is incorporated by reference.

In another alternative embodiment, the sensor device may include a microfabricated heater element and a thermal isolation structure, such as a substrate bridge or a suspended membrane. Such components may include temperature feedback sensors, such as thermistors, to assist in automated thermal control, e.g., using a microprocessor, as further described in commonly invented and assigned U.S. Provisional Application Ser. No. 60/700,953, filed Jul. 19, 2005, entitled "Improved Sensor Device With Heated Nanostructure, Including Sensor Having Thermally Isolated Nanostructure Element And Integrated Micro-Heater", which is incorporated by reference. See also C. Tsamis et al, "Fabrication of suspended porous silicon micro-hotplates for thermal sensor applications", Physica Status Solidi (a), Vol 197 (2), pp 539-543 (2003); A. Tserepi et al, "Fabrication of suspended thermally insulating membranes using front-side micromachining of the Si substrate: characterization of the etching process", Journal of Micromech. and Microeng, Vol 13, pp 323-329 (2003); A. Tserepi et al, "Dry etching of Porous Silicon in High Density Plasmas", Physica Status Solidi (a), Vol 197 (1), pp 163-167 (2003), each of which is incorporated by reference.

For certain applications thermal control may be assisted by cooling elements, such as where operating temperature need to be cycled through a substantial range of temperatures, or where high or variable ambient temperature complicates thermo-regulation. Alternative embodiments having aspects of the invention, may be include forced convection, heat sinks, thermoelectric or Peltier coolers, thermionic coolers, and the like. See for example, D-J Yao et al, "MEMS Thermoelectric Microcooler", Proc. 20th International Conference on Thermoelectrics, Beijing, China, June 2001, pp. 401-404; and US Published Applications 2003-0020,072 and 2003-0020,132, each of which is incorporated by reference.

Optionally, a sensor device may be integrated (for example on a chip or die) with additional electronic elements such as integrated circuit elements, processor elements, memory, electro-optical elements, radiation sources, wireless communication elements and the like, without departing from the spirit of the invention. See, for example, U.S. patent application Ser. No. 11/111,121 filed Apr. 20, 2005 entitled "Remotely communicating, battery-powered nanostructure sensor devices," which is incorporated by reference.

Network Properties and Multiple Device Substrate Processing

Devices fabricated from random networks of SWNTs eliminates the problems of nanotube alignment and assembly, while maintaining the sensitivity of individual nanotubes. In addition, a conducting channel 106 comprising a generally random dispersion of individual nanoparticles advantageously permits a "statistical," rather than a "localized" approach to nanostructure device fabrication, which may be more amenable to demanding mass production techniques. In the "statistical" approach, electrical contacts can be placed anywhere on the dispersion of individual nanostructures to form devices, without a specific correspondence between electrode position and any particular nanoparticle position. The random dispersion of nanoparticles ensures that any two or more electrodes placed thereon can form a complete electrical circuit with functioning nanostructures providing the connection. By distributing a large plurality of randomly oriented nanotubes in a dispersion over (or under) an electrode array, uniform electrical properties in the individual devices can be assured with higher yields and faster processing than is possible using the prior art approach of controlled placement or growth of individual nanotubes or other nanostructures.

However, carbon nanotubes are known to exhibit either metallic or semiconductor properties, depending on the particular graphitic lattice orientation. Various methods may be employed to select a desired composition of nanotubes for a nanostructure layer 106 of a nanosensor device 102. In certain method embodiments, a network of nanostructures for conducting channel 106 may be constructed from preprocessed source nanotube material which includes a selected composition of metallic versus semiconductor properties (e.g., solely semiconductor nanotubes).

In alternative method embodiments, a plurality of generally similar nanotube devices may be fabricated in a parallel mass production process (e.g., a wafer-scale process), such as an array of device dies disposed on a silicon wafer. Each of the plurality of devices will exhibit an electrical characteristic with a statistically predictable range of characteristics, due to differing metallic or semiconductor composition of each devices conducting layer 106.

Such a process may produce high yield, and permits testing (and marking or culling if necessary) of devices while still on the un-diced wafer. The fabricated dies (either as deposited or following post-deposition treatment) may be individually tested, such as by automated or semi-automated pin probe test rigs. Dies exhibiting a selected electrical behavior or range of behavior may be marked and selected for further processing and use, and any non-conforming dies may be culled, or otherwise processed for other uses.

Where the nanotube layer is formed of a mixture of nanotube compositions exhibiting a range of properties, the nanotube layer may optionally be subsequently treated to selectively remove, oxidize, disconnect or deactivate all or a portion of the metallic nanotubes, e.g., by ohmic heating, so as to leave a conducting channel of selected properties (e.g., solely semiconductor nanotubes). The latter approach may be employed advantageously where a random nanotube network layer is formed directly upon the substrate, for example by catalyst initiated CVD.

Such nanosensor devices may be produced in large scale production, such as on 100 and 150 mm silicon wafers, containing up to 40,000 active devices per wafer, with features in size regimes below optical resolution. Metal lines can be deposited by optical lithography onto the nanotubes to make electrical contact. Similar multiple device processing and testing techniques may be employed with devices having non-silicon substrates, such as flexible polymer or porous substrates, and with alternative nanostructures, such as nanotube networks deposited from liquid suspension, on porous substrates, and the like.

Alternative Sensor Architectures

While FIG. 1A serves as a generic schematic of nanostructure sensor architecture for purposes of certain of the examples having aspects of the invention described in greater detail below, alternative architectures and measurement processes are possible without departing from the spirit of the invention. It should be understood that sensors configured for particular applications and analytes are typically different in detail due to the particular functionalization and optimization of the sensor elements. An electronic sensing device for detecting an analyte having aspects of the invention may include circuitry and elements configured and optimized for measurement of capacitance and/or impedance relative to a nanostructured sensor element, for example, the response of the capacitance of a functionalized nanotube network to interaction with an analyte of interest.

Figure 3:
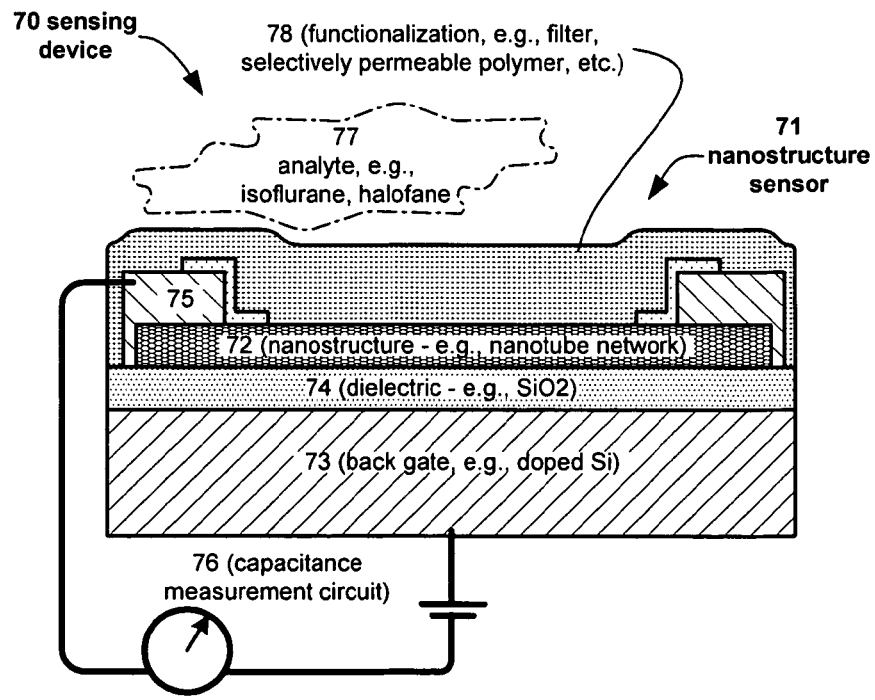
FIG. 3 is a cross-sectional diagram which illustrates an exemplary electronic sensing device, similar in a number of respects to the device of FIG. 1A, configured in this example as a capacitance sensor for detecting an analyte, such as a fluorinated anesthetic.

FIG. 3 is a cross-sectional diagram which illustrates an exemplary electronic sensing device 70 having aspects of the invention, similar in a number of respects to the device of FIG. 1A, configured in this example as a capacitance sensor for detecting an analyte, as further described in commonly invented and assigned U.S. Provisional Applications No. 60/660,441, filed Mar. 10, 2005, entitled "Integrated Systems Including Cell Membranes and Nanoelectronic Devices"; and No. 60/669,126, filed Apr. 6, 2005, entitled "Systems Having Integrated Cell Membranes And Nanoelectronics Devices, And Nano-Capacitive Biomolecule Sensors", each of which is incorporated by reference. Nanostructured capacitance sensors are particularly effective for detecting species such as fluorinated organic anesthetic agents.

As shown in FIG. 3, sensing device 70 includes a nanostructure sensor 71 which includes a nanostructure conductive element 72, in this example a carbon nanotube network, disposed upon a substrate comprising a dielectric isolation layer 74 disposed upon a base 73, in this example a doped silicon wafer back gate. The nanotube network 72 is contacted by at least one conductive electrode 75 (a pair are shown, in this case having optional passivation on the electrode-nanotube contact region). The sensor device 70 further includes at least a capacitance measurement circuit 76 in electrical communication with contact 75 and back gate 73, so as to permit the capacitance and/or impedance of the spaced apart nanotube network/back gate assembly to be readily measured (i.e., the total charge required to be placed on either conductor to create a given voltage potential between conductors, $C=Q/V$). It should be understood that other capacitor conductors may be substituted for back gate 73 without departing from the spirit of the invention, such as a top gate, liquid gate, a second spaced-apart nanotube network conductor, and the like. Additionally, many alternative functional arrangements of the respective conductors are possible. The capacitance C of the sensor 71 may be calibrated, and compared analytically with the capacitance during exposure to analyte of interest 11 (e.g., isoflurane, halofane, and the like). In particular, species having significant dipole moments may act to change the capacitance upon interaction with the nanotube network 72. See for example, U.S. Provisional Application Ser. No. 60/669,126, filed Apr. 6, 2005, entitled "Systems Having Integrated Cell Membranes And Nanoelectronics Devices, And Nano-Capacitive Biomolecule Sensors", which is incorporated by reference.

Sensor Arrays

Optionally, device 100 may comprise a plurality of sensors like sensor 102 disposed in a pattern or array, such as described in prior application Ser. No. 10/388,701, entitled "Modification Of Selectivity For Sensing For Nanostructure Device Arrays" (now U.S. Pat. No. 6,905,655), which is incorporated by reference herein. Each device in the array may be functionalized with identical or different functionalization. Identical device in an array can be useful in order to multiplex the measurement to improve the signal/noise ratio or increase the robustness of the device by making redundancy. Different functionalization may be useful for providing sensitivity to a greater variety of analytes with a single device.

The nanoscale elements can be fabricated into arrays of devices on a single chip for multiplex and multiparametric applications. See for example, U.S. patent application Ser. No. 10/656,898 entitled "Polymer Recognition Layers for Nanostructure Sensor Devices", U.S. patent application Ser. No. 10/940,324 entitled "Carbon Dioxide Nanoelectronic Sensor"; and U.S. Provisional Patent Application Ser. No. 60/564,248 entitled "Remotely Communicating, Battery-Powered Nanostructure Sensor Devices," each of which is incorporated herein by reference.

A sensor array embodiment may provide for a number of advantageous measurement alternatives, methods and benefits according to the invention, for example:
   a) multiple analytes detected by a plurality of specifically functionalized sensors,
   b) increased precision and dynamic range by a plurality of sensors each of which is optimized for a different range,
   c) increased analyte specificity and flexibility by detecting a characteristic "profile" of responses of a target analyte to a plurality of differently-functionalized sensors,
   d) self calibration systems and isolated reference sensors,
   e) multiple-use array having a plurality of deployable one-time-use sensor sub-units, or
   f). ultra-low-cost, direct-digital-output sensor arrays, including a plurality of sensors, each producing a binary signal, and collectively having a range of response thresholds covering a selected analyte concentration range.

Alternative Measurement Circuitry

The electronic circuitry described is by way of illustration, and a wide range of alternative measurement circuits may be employed without departing from the spirit of the invention. Embodiments of an electronic sensor device having aspects of the invention may include an electrical circuit configured to measure one or more properties of the nanosensor 120, such as measuring an electrical property via the conducting elements 110-114. Any suitable electrical property may provide the basis for sensor sensitivity, for example, electrical resistance, electrical conductance, current, voltage, capacitance, transistor on current, transistor off current, and/or transistor threshold voltage. In the alternative, or in addition, sensitivity may be based on a measurements including a combination of properties, relationships between different properties, or the variation of one or more properties over time.

Note that a sensor system may include suitable circuitry to perform measurement of more than one properties of a single electronic sensor device. In the example shown in FIG. 1A, the voltage or polarity of source 110 relative to drain 112 may be variable, e.g., the applied voltage may be DC, AC, pulsed, or variable. In an embodiment of the invention, the applied voltage is a DC voltage. In alternative embodiments, a sensor device configured as a NTFET may have (a) resistance or conductance measurements performed across the conductive channel element, (b) channel resistance or conductance may be measured under the influence of constant or variable gate voltage, (c) a capacitance or impedance of the device measured relative to the gate electrode and the conductive channel, (d) time integrated characteristics such as hysterisis, phase shifts, recovery behavior, or like properties or combinations thereof. For example, a transistor sensor may be controllably scanned through a selected range of gate voltages, the voltages compared to corresponding measured sensor current flow (generally referred to herein as an I-Vg curve or scan). Such an I-Vg scan may be through any selected gate voltage range and at one or more selected source-drain potentials. The Vg range is typically selected from at least device "on" voltage through at least the device "off" voltage. The scan can be either with increasing Vg, decreasing Vg, or both, and may be cycled positive or negative at any selected frequency.

From such measurements, and from derived properties such as hysteresis, time constants, phase shifts, or scan rate/frequency dependence, correlations may be determined with target detection or concentration. The electronic sensor device may include or be coupled with a suitable microprocessor or other computer device as known in the art, which may be suitably programmed to carry out the measurement methods and analyze the resultant signals. Those skilled in the art will appreciate that other electrical or magnetic properties may also be measured as a basis for sensitivity. Accordingly, the embodiments disclosed herein are not meant to restrict the types of device properties that can be measured. Optionally, the measurement circuitry may be configured so as to provide compensation for such factors as temperature and pressure and humidity. See U.S. patent application Ser. No. 11/111,121 filed Apr. 20, 2005 entitled "Remotely communicating, battery powered nanostructure sensor devices," which is incorporated by reference.

Anesthesia Agent Sensor Examples

FIG. 4A shows a series of three molecular diagrams of medically important fluorinated organic anesthetic agents, halofane, isoflurane, and sevoflurane.

FIG. 4B shows a plot of the response of an exemplary nanostructure sensor to exposure to the anesthesia agents isoflurane and halofane, as further described in commonly invented and assigned U.S. Provisional Application No. 60/683,460, filed May 19, 2005, entitled "Multi-Valent Breath Analyzer Having Nanoelectronic Sensors, And Its Use In Asthma Monitoring", which is incorporated by reference. The nanosensor employed is generally similar to that diagramed in FIG. 3, and the plot shows the effect on a capacitance signal during a sequential exposure of the agents in the presence of ambient air, first a brief exposure to isoflurane, followed by a recovery period, and then subsequent exposure to halofane. The vertical axis is measured capacitance, and the horizontal axis is time in seconds. Note the reaction is very rapid, as is the recovery time. After the initial exposure, the recovered sensor capacitance is quite constant. In the example of FIG. 4B, the nanotube network 72 of sensor 71 was directly exposed to the analyte media (air, with sample analyte admixed).

As shown in FIG. 3, additional functionalization 78 may be included in sensor 71 (e.g., an absorbent filter, a selectively permeable polymer layer, a selectively reactive or binding species, etc., to enhance selectivity, sensitivity and/or signal strength). See, for example, U.S. Provisional Application No. 60/669,126, filed Apr. 6, 2005, entitled "Systems Having Integrated Cell Membranes And Nanoelectronics Devices, And Nano-Capacitive Biomolecule Sensors", which is incorporated by reference.

FIGS. 5A-5C are plots of the capacitance responses of the devices, generally similar to those of FIGS. 1A and 5 including circuitry for measurement of both source-drain resistance and source-gate capacitance, to sequential samples of a selected anesthetic agent gas in air, through a graded series of concentrations. The samples are administered in timed pulses of approximately 60 second duration each. The capacitance values are superimposed upon a signal measuring the simultaneous source-drain resistance (V gate bias=0), the capacitance units being shown on the left-hand axis, and the resistance units on the right-hand axis. The overlay dashed line at each concentration is not a measured value, but an approximated mean level, shown for clarity and convenience.

FIG. 5A shows the response to samples sevoflurane in air. The sample pulses are administered in a graded series of concentrations ranging from 1% to 8% sevoflurane. The pulsed samples include of two initial cycles to the maximum concentration of 8%, separated by a comparable recovery period of air contact only. The response of the device to the agent in both the capacitance and resistance signals can be seen to be very rapid, with a rapid recovery. There is a consistent recovery in capacitance level. Following the initial samples, the pulses proceed by graded steps, ramping increasing to maximum and then ramping decreasing to air-only. The response of capacitance is generally consistent between increasing and decreasing concentration, confirming the recovery performance. The relation of capacitance to sevoflurane concentration can be seen to be in the opposite direction, each generally proportional in magnitude to the other.

FIG. 5B shows the response of both capacitance and resistance signals to samples of isoflurane in air. The sample pulses are administered in a graded series of concentrations ranging from 1% to 5%, in most cases separated by a comparable recovery period of air contact only. Plotted in the same manner as the data in FIG. 5A, the plot shows response and recovery to be consistently very rapid. The response of capacitance is generally consistent between increasing and decreasing concentration, and the recovery level is reasonably consistent.

Similarly, FIG. 5C shows the response of both capacitance and resistance signals to samples of halothane in air. The sample pulses are administered in a graded series of concentrations ranging from 1% to 5%, in most cases separated by a comparable recovery period of air contact only. The pattern of response is generally qualitatively similar the data in FIG. 8B, response and recovery consistently very rapid, the response of capacitance is generally consistent between increasing and decreasing concentration, and the recovery level is reasonably consistent.

Simultaneous conductance and capacitance measurements on a SWNT network may be used to extract an intrinsic property of molecular adsorbates. Adsorbates from dilute chemical vapors produce a rapid response in both the capacitance and the conductance of the SWNT network. These responses are caused by a combination of two distinct physiochemical properties of the adsorbates: charge transfer and polarizability. It has been shown that the ratio of the conductance (or resistance) response to the capacitance response is a concentration-independent intrinsic property of a chemical vapor that can assist in its identification (E. S. Snow and F. K. Perkins, Naval Research Laboratory, Washington, D.C. 20375, personal communication). See also: Snow E S, Perkins F K, Houser E J, Badescu S C, Reinecke T L, "*Chemical detection with a single-walled carbon nanotube capacitor*", Science 2005 Mar. 25; 307 (5717):1942-5, which article is incorporated by reference herein.

FIG. 5D graphically illustrates the relative ratios of change of resistance and capacitance for 5% concentration of each agent in air, as depicted in FIGS. 5A, 5B and 5C. For each agent, the left arrow represents the magnitude of change of capacitance signal from air-only to an agent-air 5% mixture, and the right arrow represents the magnitude of the corresponding change in the resistance signal. It can be seen that the ratio to the capacitance and resistance signals is a distinct value for each of the agents, sevoflurane, isoflurane and halothane. The this ratio may be used to confirm or distinguish the identity of an anesthetic agent, and advantageously this may be done in conjunction with the simultaneous measurement of the agent's concentration. It has been shown by Snow and Perkins (cited above), where Vg is the voltage of a substrate gate such as is shown in FIGS. 1A and 5, then the signals of capacitance and conductance (or resistance) may be converted for comparison (e.g., ratio calculation) to normalized values in units of $\Delta Vg$ that represent the change in the substrate gate electrode (counter electrode) voltage required to produce an equivalent change in capacitance $\Delta C$ (or change in resistance $\Delta R$), i.e. $\Delta C^* = \Delta C/(dC/dVg)$ and $\Delta G^* = \Delta R/(dR/dVg)$ where the derivatives are evaluated at $Vg=0$.

Additional Alternative Nanosensor Examples.

In addition to the examples of nanostructured sensor devices described above, the following embodiments having aspects of the invention may be employed.

Capacitive sensing may exploit the principle that analyte molecules which are present adjacent to (or binding with) the nanostructured element (e.g., carbon nanotube or CNT network) or functionalization material (e.g., recognition layer) can cause a change the physical or dielectric properties, so as to change the capacitance and/or impedance of the device structure. Preferably any functionalization material that may be disposed to coat the nanotubes is thin and electrically insulating to improve the ratio between capacitance and Faradaic currents. In an active device, such as a sensor for the detection for anesthetic agents, a capacitive electrode may be interrogated with AC signal. Analyte polarizability can be modulated by peak-peak voltage and the AC frequency providing a 2D image of the analyte for better sensitivity and accuracy. Bode plots may provide the frequency dependence of impedance magnitude and phase angle. Data may be plotted as differential capacitance as a function of time. Capacitance measurements do not require a conduction path and are therefore are flexible in terms of functionalization chemistries.

Figure 9:
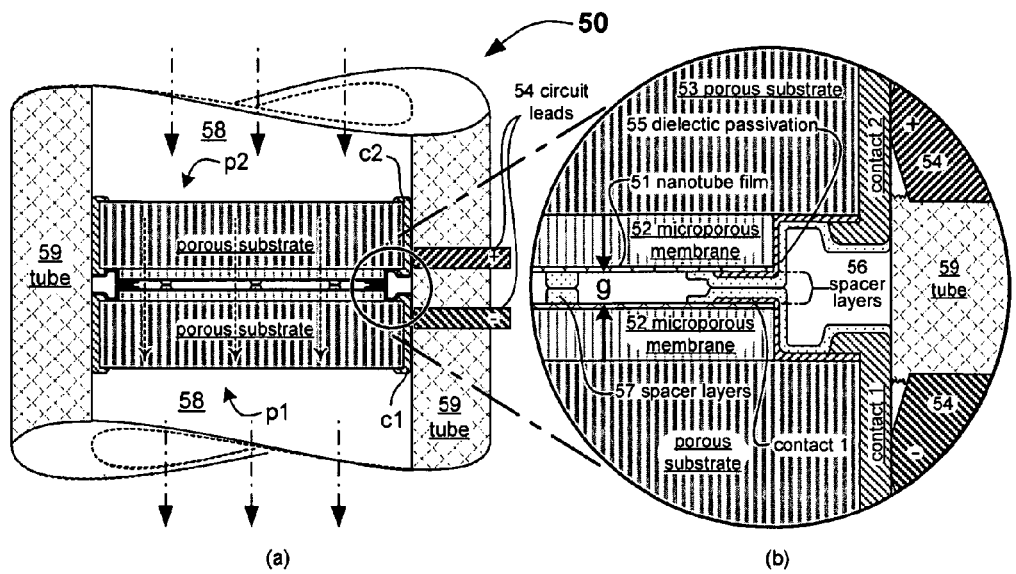
FIG. 9 is a cross-sectional diagram including view (a) which illustrates an exemplary flow-though sensor device disposed on a porous substrate, in this example mounted in a capillary or tube conducting a gaseous or liquid analyte medium, and view (b) which is an enlarged detail of the sensor structure.

FIG. 6 shows a nanostructured sensor device 900, (this is FIG. 9 of commonly assigned U.S. patent application Ser. No. 11/090,550 filed Mar. 25, 2005 entitled "Sensitivity control for nanotube sensors", which is a divisional application of U.S. patent application Ser. No. 10/280,265 filed Oct. 26, 2002 (now U.S. Pat. No. 6,894,359), which in turn claims priority to U.S. Provisional Application No. 60/408,412 filed Sep. 4, 2002; which is incorporated by reference).

FIG. 6 shows a trench 930 in the top layer 840 of the substrate 830 below a section 950 of the nanostructure 810 in an embodiment of the invention. The trench 930 isolates the nanostructure section 950 of the nanostructure 810 from the top layer 840 of the substrate 830. This architecture that may be operated as one or more of a resistive sensor, a capacitive sensor, an impedance sensor, or a transistor sensor, depending on the circuitry (not shown) used to activate and measure between contacts 820-1, 820-2 and substrate gate 850. For example, a voltage supply can apply a voltage to the substrate 850 that can act as a counter or gate electrode for the device, and the capacitance or impedance of the counter electrode 850 relative to nanostructure 950 may be measured. The gate voltage can be DC, AC, or both. Trench 930 permits analyte and analyte media to diffuse or flow between nanostructure 950 and the counter electrode 850. The trench 930 can be formed by wet etching, by dry etching, or by any method that will remove substrate material 840, 830 without harming the nanostructure 810. Buffered oxide etch (BOE), which is well known in the semiconductor arts, can be used as a wet etch agent for silicon oxides. Dry etch gases such as xenon difluoride ($XeF_2$) can be used to etch silicon. In one embodiment, the depth of the trench is between about 1 nm and 1 mm. In another embodiment, the depth of the trench is between about 10 nm and 100 nm.

Figure 7:
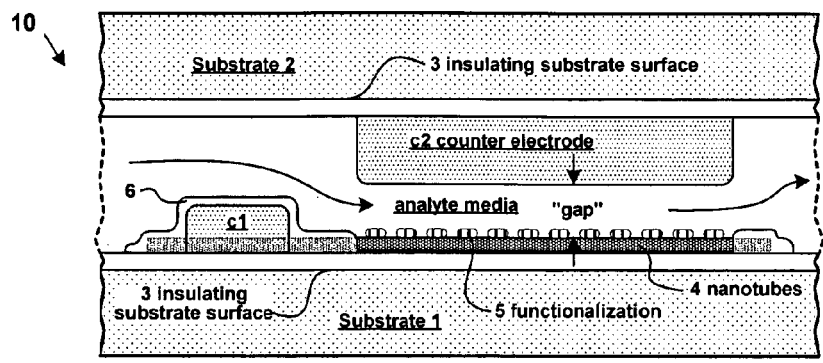
FIG. 7 is a cross-sectional diagram illustrating a capacitive sensor having a nanostructure portion spaced apart from a opposing plate having a counter electrode, so as to define a conduit for a gaseous or liquid analyte medium.

FIG. 7 schematically illustrates a CNT capacitive sensor 10 having spaced-apart "plates" in a sandwich configuration. The spaced apart configuration permits flow or diffusion of an analyte medium between the plates. A CNT network may be included as first "plate" of a capacitor, and a counter electrode comprising a metallic or non-metallic conductor may be included as a second plate of a capacitor. In the example shown, the geometry is defined by opposed and spaced-apart substrates 1 and 2, which may comprise of an insulating material and/or have an insulating surface 3 to provide electrical isolation. A CNT network 4 may be included as a capacitive electrode or plate, preferably in communication with one or more electrical contacts c1 (e.g., metal electrodes). Optionally, the all or portions of the contacts c1 (and/or c2) and adjacent nanotubes may be coated with passivation material 6, see the above mentioned U.S. Pat. No. 6,894,359 which is incorporated by reference. A second plate or counter electrode c2 has a surface separated from the first plate by a separation space or "gap." Alternatively, both "plates" or counter electrodes may include nanostructure elements, such as CNT network. Optional functionalization 5 may be included on this structure (either on the metal plate, on the CNT network, or on other adjacent elements) to enhance sensitivity or selectivity.

The material or space (e.g., dielectric material, analyte media, air, vacuum, combinations of these, and the like) within the gap or plate separation has a dielectric constant or constants which contributes to the magnitude of capacitance.

Presence or absence of analytes on a capacitor plate, in the separation space, or adjacent to and electrically influencing these structures may in the change the capacitance and/or impedance of the structure and can be detected by external measurement equipment. The change in capacitance can be affected by the dipole moment of the molecules in contact with the capacitor. In addition, large dipole molecules can be included in the system (for example, as a recognition material or signal enhancer) that specifically bind to the analyte of interest (sandwich assay) to further enhance the signal of the detection. Measurement of capacitance is a well known technique in medical and diagnostic devices. Low cost electronic acquisition chips exist to quantify the change in capacitance and impedance (e.g., chips made by Analog Devices, among others).

Figure 8:
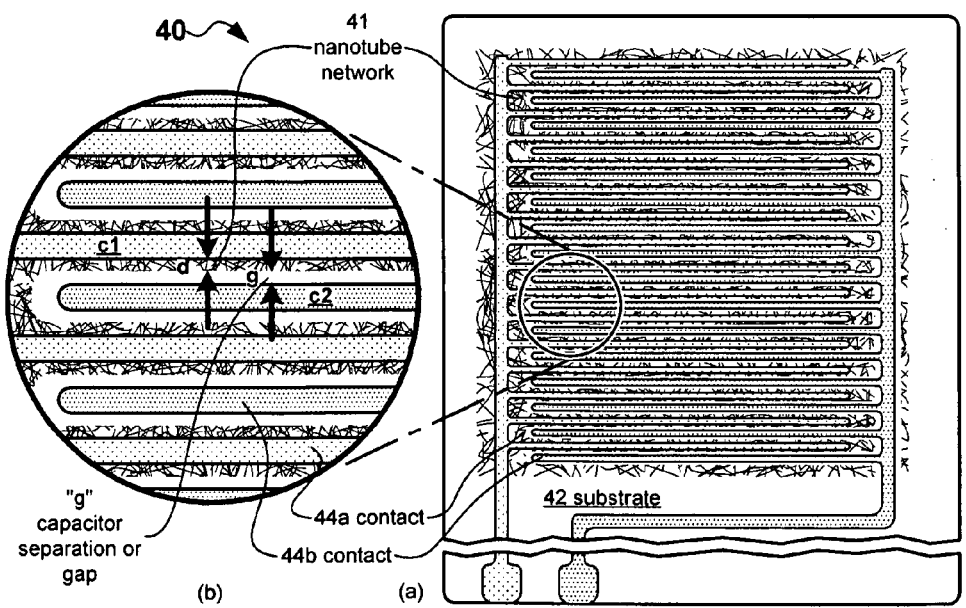
FIG. 8 is a plan-view diagram including view (a) which illustrates an exemplary planar nanotube capacitor sensor device, and view (b) which is an enlarged detail of the sensor structure.

FIG. 8, views (a) and (b), show an exemplary sensor device, configured as a planar (2D) embodiment of a CNT network capacitance sensor 40; view (b) is a detail portion shown in a magnified sub-drawing at the left. The sensor device 40 comprises a nanostructured film or network 41, preferably including an interlinking network of carbon nanotubes disposed on a substrate 42. The substrate may be generally similar the that described for other embodiments herein, e.g., a silicon base with a dielectric top layer, e.g., $SiO_2$. The nanotube network may be formed as described herein. The network 41 may be functionalized to suit a particular application and target analyte or analytes. In the example shown, at least two conducting contacts 44a and 44b are included, e.g., formed by metal vapor deposition and masking so as to be arranged in an interdigitated fashion upon the nanotube network 41.

Note that a defined portion of the nanotube network is selectively burned, etched or otherwise removed from a patterned offset (e.g., using appropriate masking or the like), so that one of the contact sets 44a (when deposited) lies free of contact with the remaining network 41, and the other contact 44b set lies in electrical contact or communication with the network. In the example shown in FIG. 16, the space between interdigitated fingers of contacts 44a and 44b generally includes a width "d" of network adjoining a gap "g" of bare substrate, so as to form the elements of a capacitor. Upon application of a voltage potential between contacts 44a and 44b, charge accumulates on the spaced-apart contact 44a and the nanotube network 41, separated by gap "g," thereby producing an electric field potential between the two. Preferably, the offset gap "g" is small. Interaction of an analyte of interest (not shown) with the nanotubes of the network 41 will tend to change the effective dielectric of the gap, and thus measurably change the capacitance (particularly in the case of species with a substantial dipole). The nanotube network (or other nanostructure) provides a large number of small features which act to intensify the electric field gradient locally, increasing signal-to-noise ration of a signal in response to an analyte of interest.

FIG. 9 shows an exemplary capacitive sensor device 50 having a capacitive plate including a nanostructured film 51, such as a CNT network disposed upon a microporous membrane 52, as further described in commonly assigned U.S. Provisional Application Nos. 60/669,126, filed Apr. 6, 2005, and No. 60/683,460, filed May 19, 2005, each of which is incorporated by reference. In this example, the membrane is further supported by a porous structure or substrate 53. See the section of this application above entitled "Alternative Porous Substrate" for further description of these materials. The plate structure p1 electrically communicates with an electrical lead or contact c1, which in this example leads to a perimeter contact portion for connection to circuit leads 54.

In the example shown in FIG. 9, the plate p1 is disposed in a spaced-apart mirror image arrangement with a substantially similar opposing plate p2, together plates p1 and p2 comprising a capacitive structure. Alternatively, plate p2 may comprise a counter electrodes, such as a porous, perforated or digitated conductor. All or a portion of contacts c1 and c2 may be passivated, such as with coating 55. In this example, the thickness of passivation material 56 and underlying metal contact c1 or c2 is selected so as to form a "spacer" structure 56, which serves to control the gap "g" between the nanotube film 51 of each plate. Optionally additional intermediate spacer portions 57 may be included to control or maintain a selected gap "g" between plates p1 and p2. The gap may be adjusted by a variable coating of these layers, and rigidity and flatness of the support selected to allows control of gap "g" to a small tolerance.

In the example shown in FIG. 9, the sensor device 50 comprising opposed plates p1 and p2 is mounted in a bore or lumen 58, for example in capillary structure or tube 59, and is disposed perpendicularly to the lumen 58, so as to form a plug structure. Analyte medium (gaseous or liquid) may flow along lumen 58 so as to penetrate the porous structure of plates p1 and p2, so as to fill gap "g," interacting with the CNT film. Target analytes in the medium influence the capacitance of the spaced apart films 51, so as to produce a signal measurable via leads 54. In certain embodiments, lumen 58 is the lumen of a polymer capillary, and electrical leads 54 may be "spiked" or otherwise inserted into the lumen to connect to contacts C1 and c2. It is apparent to one of ordinary skill in the art that a number of practical alternative arrangements and mountings of the sensor 50 are possible, without undue experimentation and without departing from the spirit of the invention.

One advantage of disposing a nanosensor device upon a micro-porous membrane or substrate, is that detection chemistry may be accelerated, analyte molecules concentrated, and sensitivity improved. As shown schematically in FIG. 10A, where analyte medium flows parallel to a nanosensor surface, the detection chemistry tends to be transport limited, depending on the diffusion of target molecules across a surface boundary layer to interact with sensitive elements, e.g., a CNT film and/or associated functionalization material. Where a micro-porous membrane permits flow of analyte medium perpendicularly through the nanosensor surface, the detection chemistry tends to be reaction limited, i.e., the rate at which the target molecules bind or otherwise interact with the sensitive elements. This effect can permit the porous substrate to respond more quickly.

Similarly, in certain embodiments, the micro-porous membrane can act as a filter, to concentrate or detain target molecules adjacent the sensitive elements, as solvent or suspension phase fluid (e.g., gas or liquid solvent) pass through the membrane relatively unimpeded. This can be particularly advantageous for target analytes in low concentration or traces, such as in forensics, explosive detection, and the like. Note that additional controls can be used to regulate membrane transport, such as electrophoretic effects, and the like, without departing from the spirit of the invention.

Figure 10C:
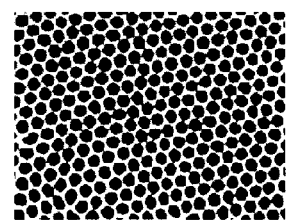

FIG. 10B shows a SEM micrograph of a commercially available microporous anodic alumina membrane with a regular pore diameter of about 20 nm (Anopore® membrane, by Whatman plc), and FIG. 10C shows a SEM micrograph of an experimental anodic alumina membrane with a hexagonal pore arrangement of about 5 nm diameter (University of Twente, Nederlands). See also, R. Schmuhl, et al, Blank, "*Si-supported mesoporous and microporous oxide interconnects as electrophoretic gates for application in microfluidic*

*devices,*" Anal. Chem. (2005) 77, pp 178-84; and S. Roy Chowdhury et al, "*Pore size and surface chemistry effects on the transport of hydrophobic and hydrophilic solvents through mesoporous g-alumina and silica MCM-48,*" J. Membrane Sci., (2003) 225 pp 177-86, each of which is incorporated by reference.

FIGS. 11A-11D illustrate alternative exemplary embodiments of nanosensors having aspects of the invention and providing for flow of analyte medium through a porous substrate, and show an exemplary module for fluidic sample analysis.

FIG. 11A is a is a cross-sectional diagram of a nanosensor embodiment 40p similar in a number of respects to the capacitive sensor shown in FIG. 8. The reference numerals refer generally to comparable elements as in FIG. 8. In this example, a nanotube network 41 (and optionally any selected functionalization material) is deposited on a microporous membrane 41a, and is shown overlain by an interdigitated pair of contacts c1 and c2 (44a, 44b). The network is restricted in coverage, so as to leave a nonconducting gap "g" between the network portion "d" and the contact 44a. The microporous membrane 41a is optionally supported by a porous support 41b, the porous substrate thus comprising 41a and 41b. Optionally a sealant 45 may be deposited on portions of the membrane 41a and support 41b not covered by sensing elements, so as to guide analyte medium to percolate through the sensor device.

FIG. 11B is a is a cross-sectional diagram of a nanosensor embodiment 100p similar in a number of respects to the NTFET sensor shown in FIG. 1A. In this example, one or more optional gate electrodes 114' (e.g., a porous or perforated conductor) are embedded within microporous membrane 41a (or alternatively, the gate '114 is disposed above the membrane 41a and covered by a thin porous insulator 46). Nanotube network 106 (and optionally any selected functionalization material) is deposited upon membrane 41a, and is contacted by a pair of contacts 110, 112. The microporous membrane 41a is optionally supported by a porous support 41b, the porous substrate thus comprising 41a and 41b.

FIGS. 11C and 11D are two orthogonal cross-sectional diagrams of an exemplary flow-though micro-fluidic sensor module 190 providing for the conduct of a gaseous or liquid analyte medium, and including one or more sensor devices disposed on porous substrates, such as the sensors 40p and 100p depicted in FIGS. 11A and 11B. In the example shown, there are four such sensors, arranged to share a common porous substrate 41 comprising a microporous membrane 41a and a porous support 41b, so that the combined devices 40p, 100p and substrate 41 form a "porous chip" 194. The chip 194 is mounted within a module housing comprising an upper portion 191a defining an analyte media inlet 192, and a lower portion 191b defining an analyte media outlet 193. Circuit leads 195 connect the devices 40p and 100p of chip 194 through a via in body 191 to an external signal connector 196. It is apparent to one of ordinary skill in the art that there are alternative fluidic arrangements and structures that may be employed without departing from the spirit of the invention. For example, body 191 may comprise an assemblage of planar portions such as glass slides, separated by spacers, shaped and formed to provide mountings and conduits (e.g., etched polymer or glass, bonded to planar portions, such as by adhesives, US welding, and the like). Sensor module 190 is preferably integrated in a detector system (not shown) providing for controlled sampling and flow of gaseous or liquid analyte media, and for the analysis and output of measurement date.

Particular Capacitive Nanosensor Architectures.

Figure 12:
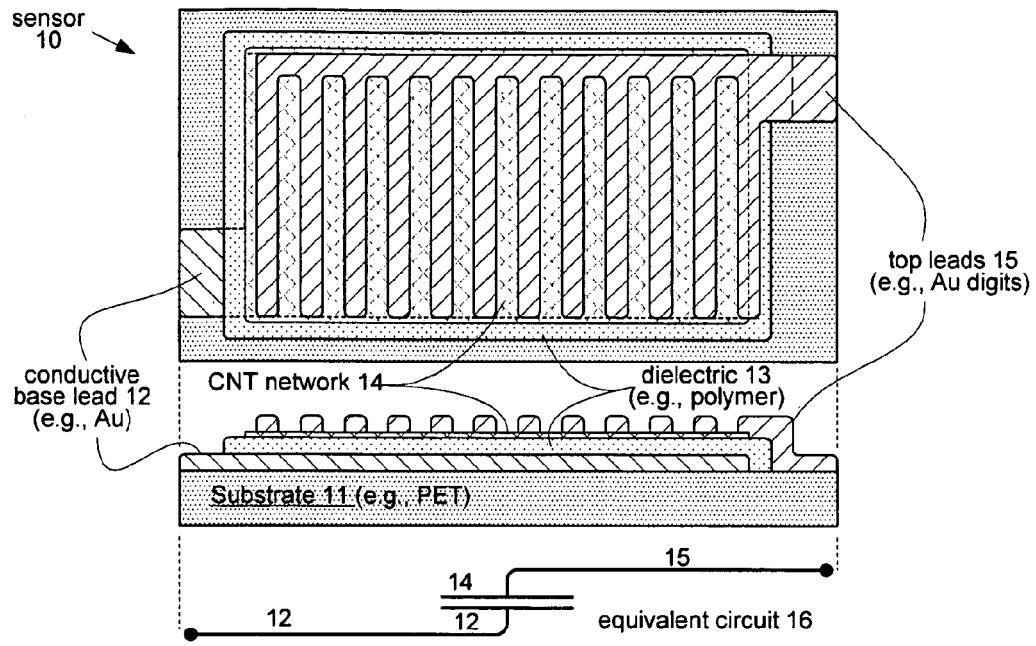
FIG. 12 is a plan view, cross-sectional view, and equivalent circuit diagram of an exemplary capacitive nanosensor embodiment having aspects of the invention, comprising a bi-layer architecture.

FIG. 12 is a plan view, cross-sectional view, and equivalent circuit diagram of an exemplary capacitive nanosensor embodiment 10 having aspects of the invention, comprising a bi-layer architecture including a substrate 11 (e.g., PET) and a conductive base or plate 12 (e.g., metal such as Au, graphite, and the like). A dielectric layer 13 (e.g., a polymer, $SiO_2$, and the like, or combinations thereof) is interposed between base plate 12 and a nanostructured element 14 (such as one or more CNT or a CNT network). Nanostructured element 14 is capacitively coupled to conductive base 12 in that base 12 is space apart from element 14 to form a pair of capacitive plates. Digitated top lead 15 is shown contacting CNT element 14 to permit electrical communication with measurement circuitry (not shown). Preferably, top leads 15 are applied in such a manner as to prevent contact with base plate 12, so as to avoid a current path between a capacitive plate pair 12, 14, as shown in equivalent circuit 16.

Figure 13:
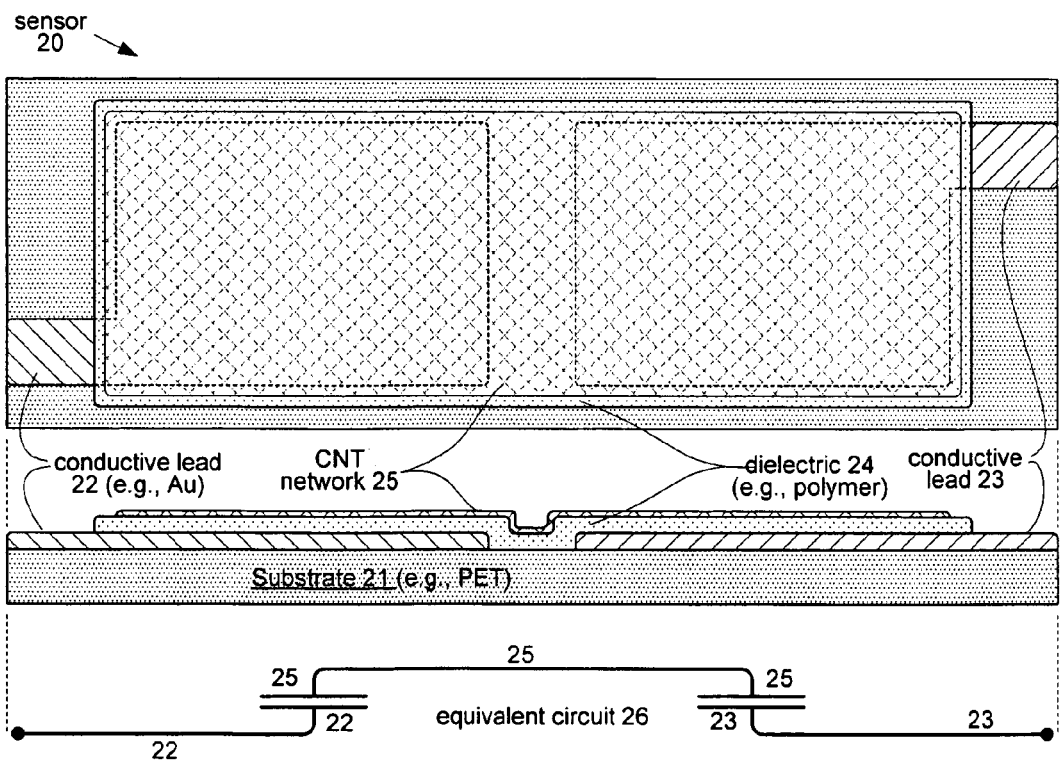
FIG. 13 is a plan view, cross-sectional view, and equivalent circuit diagram of an exemplary capacitive nanosensor embodiment having aspects of the invention, comprising off-set capacitor elements in series.

FIG. 13 is a plan view, cross-sectional view, and equivalent circuit diagram of an alternative exemplary capacitive nanosensor embodiment 20 having aspects of the invention, comprising off-set capacitor elements in series, including a substrate 21 (e.g., PET) and an offset pair of conductive leads 22, 23 (e.g., metal such as Au, graphite, and the like), preferably disposed side-by-side adjacent substrate 21, separated by a selected gap. Dielectric layer 24 (e.g., a polymer, SiO2, and the like, or combinations thereof) covers active regions of leads 22, 23 and in turn supports CNT element 25, such as a carbon nanotube network. Advantageously, CNT element 25 forms a common capacitive plate electrode opposing both leads 22 and 23 (capacitively coupled), as shown in equivalent circuit 26.

Figure 14:
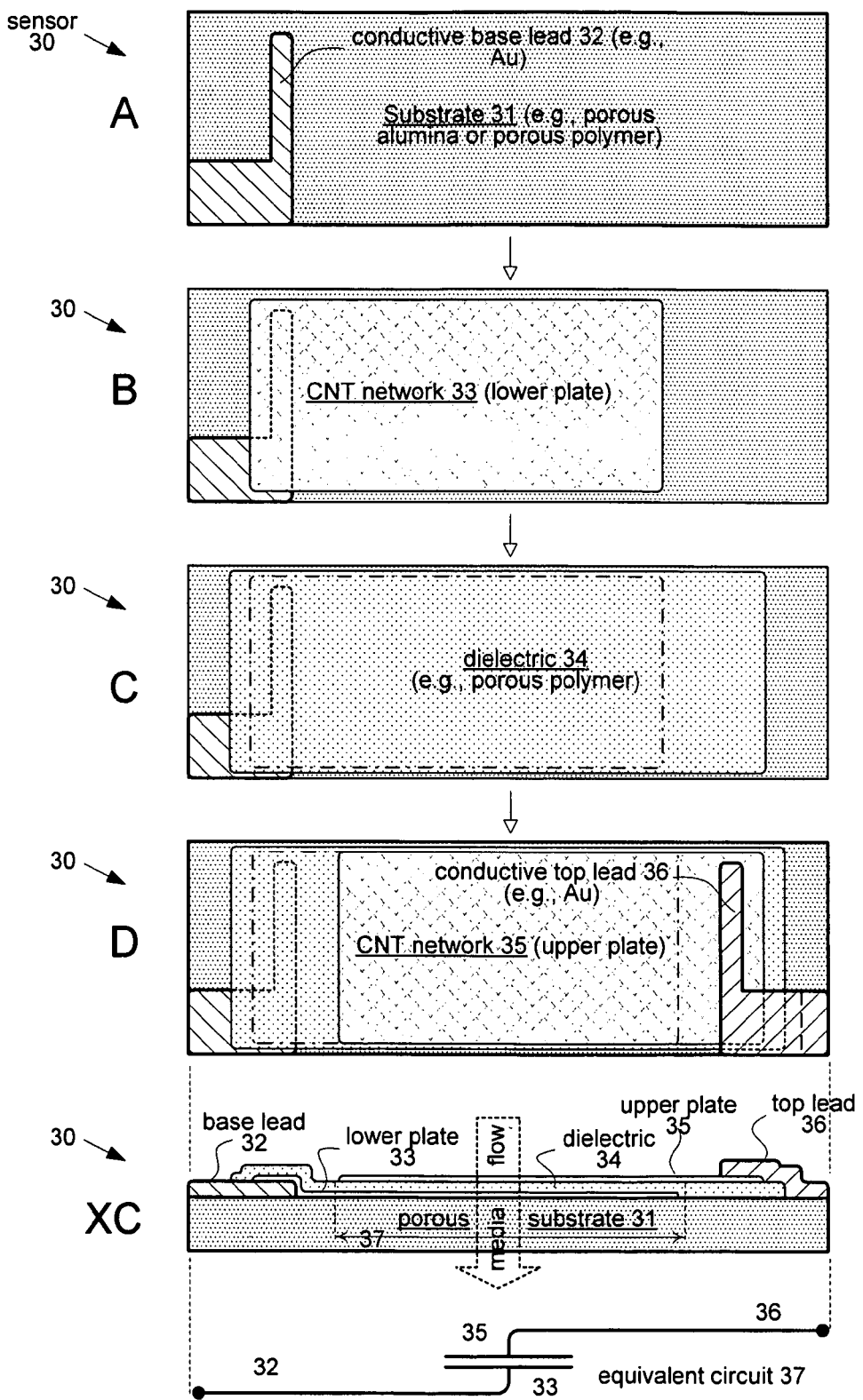
FIG. 14 is a schematic and equivalent circuit diagram which illustrates an exemplary capacitive nanosensor embodiment having aspects of the invention, and having a bi-layered architecture comprising a porous substrate supporting CNT network "plates" with off-set contact regions, wherein view A-D show sequential plan views in suggested order of assembly, and view XC shows a cross section.

FIG. 14 is a schematic and equivalent circuit diagram which illustrates an exemplary capacitive nanosensor embodiment 30 having aspects of the invention, and having a bi-layered architecture comprising a first base lead or contact pad 32 disposed adjacent a substrate 31 (porous in this example, such as porous alumina). Lead 32 contacts a lower CNT plate or element 33, which is preferably shaped so as to have an active region 37 off-set from contact 32. At least the active region of plate 33 is covered by dielectric layer 34 (e.g., porous polymer or inorganic material such as $SiO_2$). Upper CNT plate 35 covers at least the active region of lower plate 33, electrically isolated by dielectric 34, and is in turn contacted by a top lead or contact 36, which is likewise preferably offset from the active region 37. Thus, in FIG. 19, upper plate 35 is adjacent lower plate 33 and in electrical contact with lead 36, which is in turn offset and removed from proximity to plate 33. Analyte media may advantageously flow perpendicularly to substrate 31, and the upper and lower plates 33, 35 form a capacitive plate pair removed from leads 32, 36, as shown in equivalent circuit 37.

Figure 15:
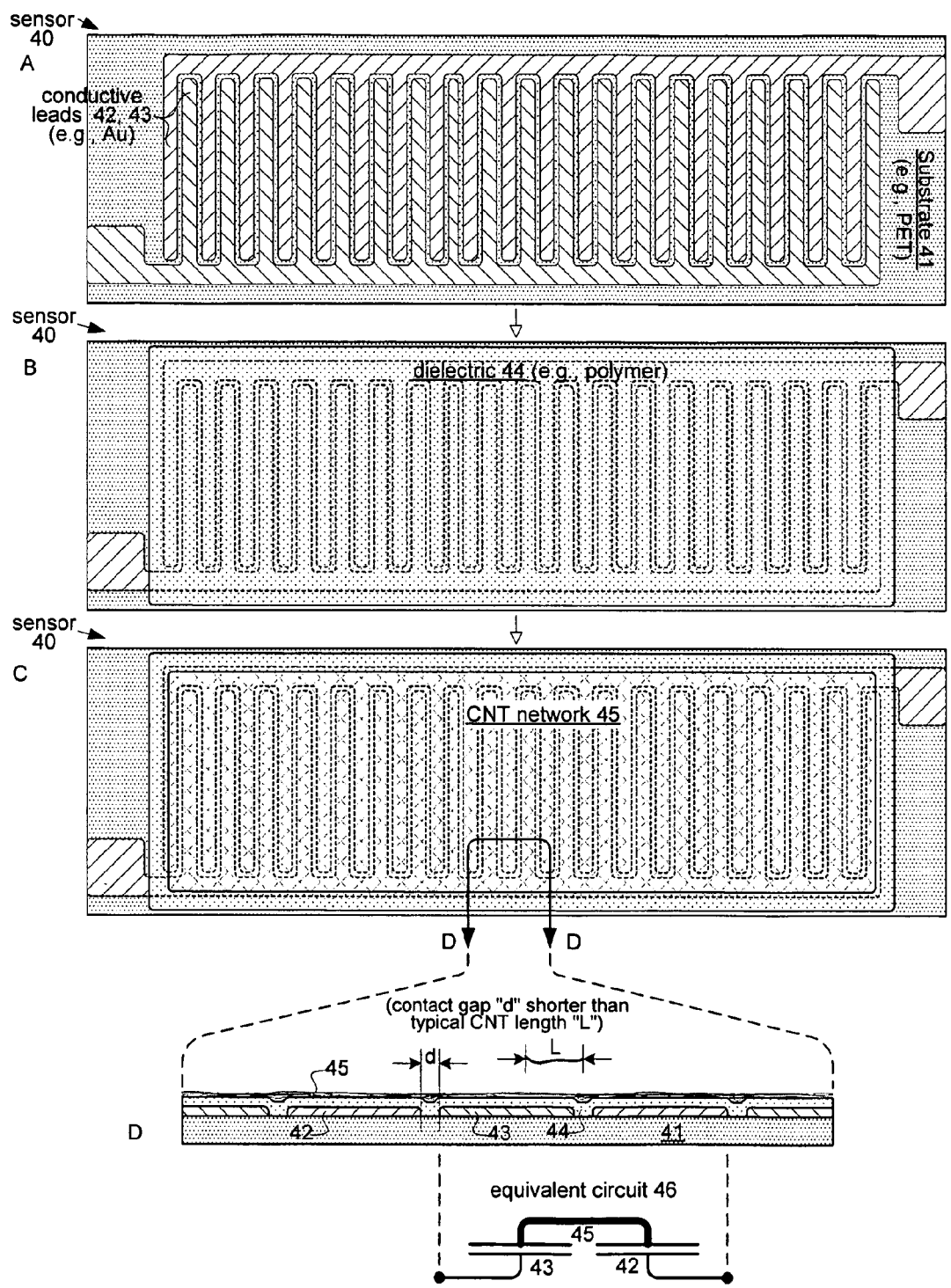
FIG. 15 is a schematic and equivalent circuit diagram which illustrates an exemplary capacitive nanosensor embodiment having aspects of the invention, comprising off-set capacitor elements in series, disposed in a "small gap" interdigitated arrangement, wherein view A-C show sequential plan views in suggested order of assembly, and view D shows a cross section.

FIG. 15 is a schematic diagram and equivalent circuit which illustrates an exemplary capacitive nanosensor embodiment 40 having aspects of the invention. In schematic architecture, the sensor 40 is similar in a number of respects to that for FIG. 13, in that conductive leads 42, 43 (e.g., metal such as Au, graphite, and the like), form an offset pattern adjacent substrate 41, covered by dielectric 44 and CNT element 45. In this example, leads 42, 43 are arranged so as to have a characteristic gap "d" that is small in comparison to the typical or characteristic length "L" of the nanotubes comprising CNT element 45 (which may include one or more aligned CNTs, or may comprise a random network). Note that while neither the gap nor the CNT length need be uniform, the statistical effect of the relation of the characteristic dimensions is that substantial numbers of nanotubes span the gap so as to have a portion capacitively coupled to each conductive lead. Advantageously, conductive leads 42, 43 may be arranged in an interdigitated pattern, and gap "g" may be created by conventional lithographic deposition methods, or may selectively etched in a continuous material. The continuity of conduction within CNT network 45 provides a low resistance path connecting the "series capacitor" regions adjacent leads 42, 43, as shown in equivalent circuit 46.

FIG. 16 is a plan view and cross-sectional view of an exemplary capillary fluidic package 50 having aspects of the invention supporting a nanosensor embodiment 40. Package 50 comprises a base material 51 supporting both sensor 40 and one or more leads, example leads 54,55 are shown contacting sensor 40 and advantageously continue to an exposed "plug" edge of base 51. A fluidic cap plate 52 is shown, including one or more ports 53 and a capillary conduit 56 connecting port(s) 53 to sensor 40. Package 50 may comprise molded components and printed circuitry, conveniently made disposable, such as for blood testing and the like.

Figure 18:
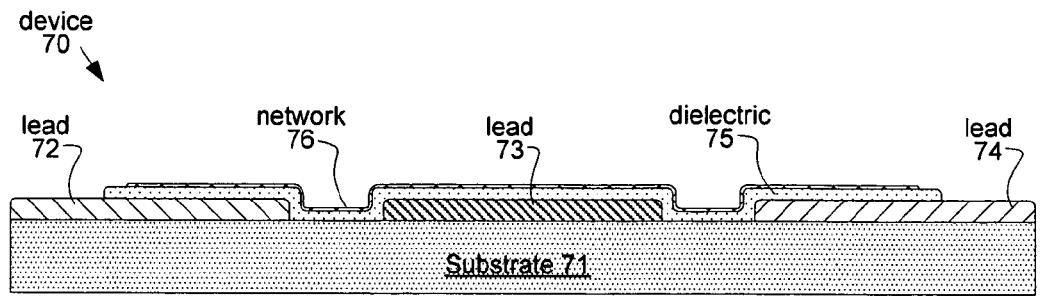
FIGS. 18 and 19 are cross-sectional views showing exemplary nanostructured devices having a network element such as a CNT network which is electrically coupled to multiple leads without direct lead-to-network contact.

FIG. 17 is a cross-sectional view and a magnified portion of an exemplary capacitive nanosensor embodiment 60 having aspects of the invention, generally similar to that shown in FIG. 18 (see elements 21, 22, and 23) and having a multi-layer dielectric structure comprising first dielectric layer 64 and a second dielectric layer 65. One of more of layers 64 and 65 are interposed between leads 22, 23 and CNT element 66. For example, layer 64 may comprise a porous or non-porous material such as $SiO_2$, and layer 65 may comprise a polymer, such as porous PAMAM. Both the porosity and hydrophilicity/hydrophobicity as well a other properties of layers 64 and 65 may be selected to suit a particular application, analyte medium and the like. One of layers 64 or 65, or an additional layer, may lie above or embedding CNT layer 66.

Figure 19:
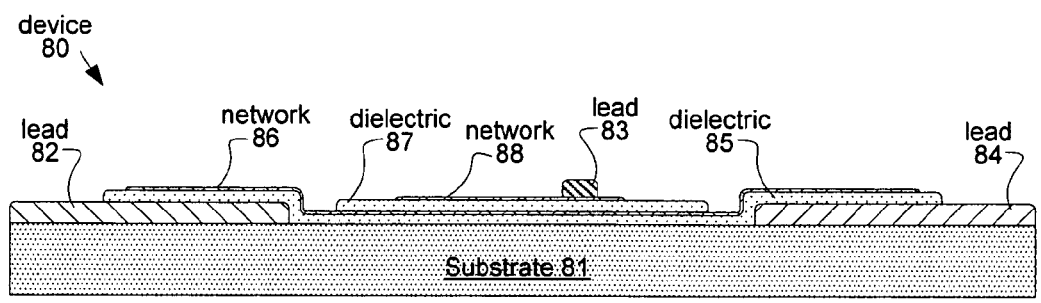

As may be seen in the foregoing examples, devices having aspects of the invention may be configured to exploit the electrical properties of one or more nanostructures, such as a film or network of nanotubes, without direct contact of conductive circuit elements with the nanostructures (e.g., without metal-to-nanotube contact regions). FIGS. 18 and 19 are cross-sectional views showing exemplary nanostructured devices having a network element such as a CNT network which is electrically coupled to multiple leads without direct lead-to-network contact. For example, in FIG. 18, device 70 (such as a nanosensor) comprises electrically continuous network 76 (such as a CNT film of greater density than the percolation limit) which is separated from spaced apart leads 72, 73 and 74 by dielectric layer 75, permitting each such lead or electrode to be capacitively coupled to network 76 without direct contact (e.g., avoiding metal-to-CNT contact). In an alternative example, in FIG. 19, device 80 (such as a nanosensor) comprises electrically continuous network 86 which is separated from spaced apart leads 82 and 84 by dielectric layer 85, permitting these leads to be capacitively coupled to network 86 without direct contact. An additional electrical influence on network 86 comprises a second plate-like network element 88, which disposed over network 86 and separated from network 86 by an additional dielectric region 87. The "plate" network is shown contacting a third lead 83, although it should be understood that lead 83 may be physically remote or offset from the network 86, such as by the arrangement shown in FIG. 19 (in FIG. 19, upper plate 35 is adjacent lower plate 33 and in electrical contact with lead 36, which is offset and removed from proximity to plate 33). The application of DC and/or AC voltages of selected frequency ranges to the leads (e.g., AC with DC bias) can result in selected electrical influences, responsive to the electrical properties of the nanotubes (e.g., resistance, impedance, inductance, capacitance, or combinations of these, and the like). The dimensions and properties of the various elements can be selected by one of ordinary skill in the art to provide desired device properties, such as high-pass, low-pass filter effects, of the various subassemblies and components.

Integration of Cell Membranes and NT-Based Sensor Embodiments

Exemplary embodiment of nanoelectronic devices having aspects of the invention include the integration of a complex biological system and a nanoelectronic device, demonstrating that both components retain their functionality while interacting with each other. In this example, the biological system includes the cell membrane of *Halobacterium salinarum*. In this example, the exemplary nanoelectronic devices includes a nanotube network transistor, which incorporates many individual nanotubes in such a way that entire patches of cell membrane are contacted by nanotubes.

The examples show that the biophysical properties of the membrane are preserved, that the nanoelectronic devices function according to their electronic design when integrated with the membrane (e.g., as transistors, capacitors and the like), and that the two systems interact to produce measurable effects, useful for a range of industrial, scientific and medical purposes, such as biological or medical sensing and detection, electro-biological control or data acquisition systems, artificial neuro-sensory organs, and the like. Further, the interaction may be used to determine the charge distribution in a biological system, e.g., so as to permit a bioelectronic device to be optimally configured without undue experimentation. For example, by means of an exemplary embodiment, it was determined that the electric dipole of the example membrane protein bacteriorhodopsin is located ⅔ of the way from the extracellular to the cytoplasmic side.

Carbon nanotubes have been suggested for use as prosthetic nervous implants in organs such as eyes and ears. To achieve this goal requires the parallel preparation of fully functional biological systems and nanoelectronic systems that are integrated together. One major obstacle is the preservation of functionality in both systems. A second major obstacle is the difference in scale between nanostructures and biological systems. While nanotubes are comparable in size to individual proteins, they are much smaller than cells. Preferred device embodiments include nanotube networks, a recently developed class of nanotube devices, to bridge the gap in size between nanotechnology and biotechnology. In this example, embodiments of nanoelectronic devices having aspects of the invention achieve integration between a functioning nanotube transistor and a cell membrane.

Figure 22B:
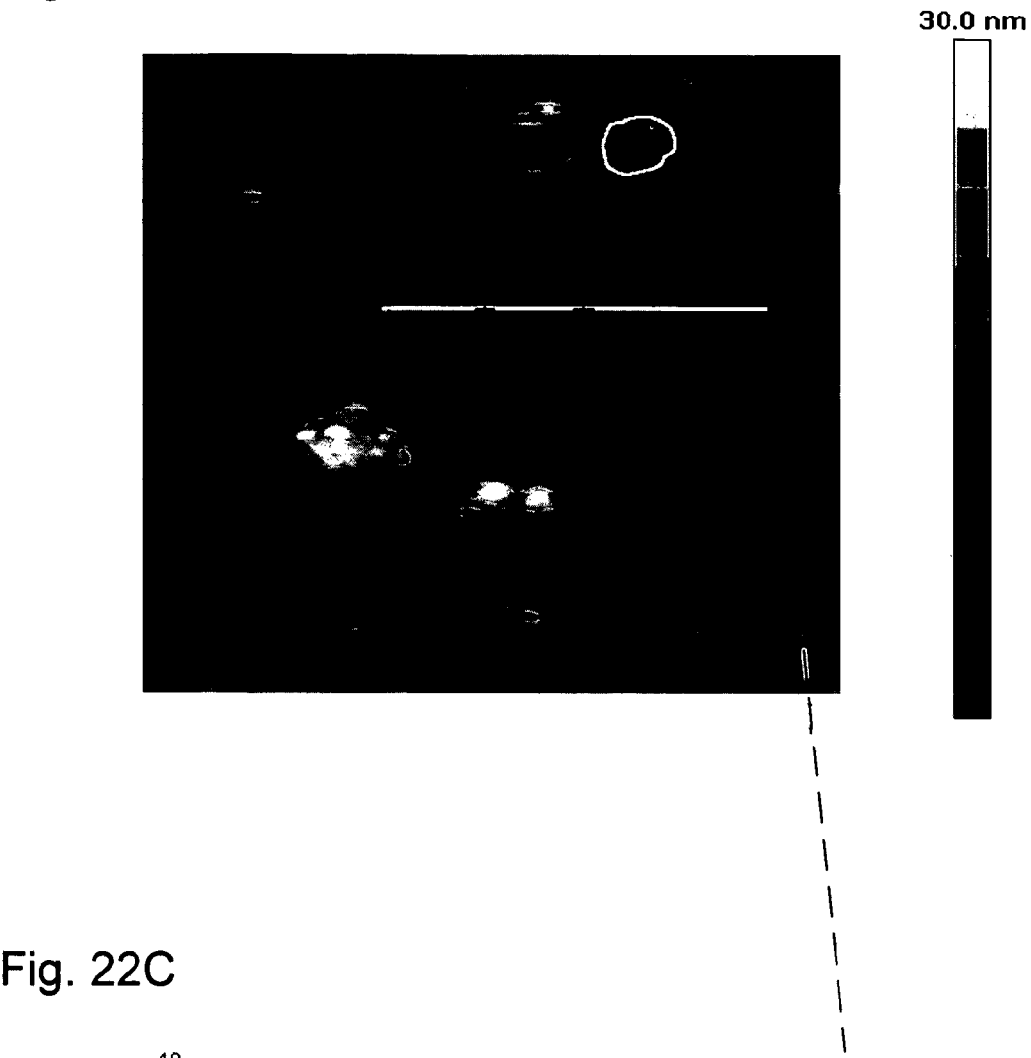
FIG. 22B shows a micrograph of a CNT network of the device as coated with cell membrane.
Figure 22C:
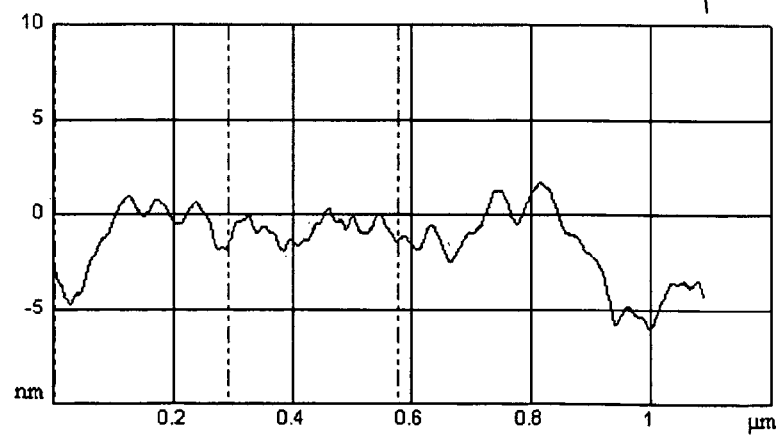
FIG. 22C shows a plot of measured membrane thickness as shown in FIG. 22B.

Portions of the structure of the certain exemplary devices having aspects of the invention are illustrated in FIGS. 20 to 22. Among other things, these devices can be employed to extract information about the charge distribution in the particular membrane used. FIG. 20 shows an atomic force microscopy image (amplitude signal) of a nanotube network. The network contains many randomly oriented carbon nanotubes, grown on a substrate (silicon oxide on metallic silicon) by CVD. The nanotubes occur individually, rather than in bundles. The density is adjusted so that the network functions as a transistor, with the gate voltage provided by the buried substrate.

As shown in the exemplary devices of FIG. 21 in views A, B and C, embodiments of devices having aspects of the invention include patches of cell membrane covered a dense network of individual carbon nanotubes contacted by metal electrodes (see Bradley et al., *Flexible Nanotube Electronics*, Nano Letters (2003) 3, 1353-55, which is incorporated by reference), referred to as a nanotube network field-effect transistor (NTN-FET). Each device comprises a substrate 24 (e.g. a doped silicon wafer having a dielectric coating 25 (e.g., $SiO_2$, $Si3N4$, and the like or combinations of these). A nanostructure layer, in this example an interlocking network of nanotubes 26, is disposed adjacent substrate 24. One or more electrical contacts 27 (a source-drain pair 27a, 27b are shown) are configured to contact the nanotube network 26. Substrate 24 may include a gate electrode (e.g., doped wafer material 24). Cell membrane material 28 disposed in communication with nanotube network 26, in which 28a indicates that the cytoplasmic side of the membrane faces the nanotubes 26, and 28a indicates that the extracellular side of the membrane faces the nanotubes 26. An liquid or aqueous phase 30 is placed on the assembled membranes, e.g., covered by an enclosing top slide or second substrate 29, which may also be of the same material as substrate 24. Both substrates 24,29 may be conveniently connected to circuitry to create a bias potential between them.

This configuration has several significant features and advantages. First, the cell membrane is in direct contact with the semiconducting channel of the transistor. Thus the devices detect local electrostatic charges on the biomolecules. This is possible because the nanotube network includes robust, air-stable semiconductors that can be exposed to cell membranes. Second, the use of a large number of nanotubes ensures that entire patches of membrane are in contact with nanotubes. Thus, the size scale of nanotechnology, which enables the semiconductor integration, is interfaced with the larger size scale of biology.

The cellular material in this example includes a portion of purple cell membrane (PM) of *Halobacterium salinarum*, an organism which has been widely studied. PM contains the light-sensitive membrane protein bacteriorhodopsin, which serves as a photochemical proton pump and has been used to fabricate phototransistors. In addition, rhodopsin has a permanent electric dipole moment, a charge distribution which produces an electric field pointing from the extracellular side of the membrane towards the cytoplasmic side. In one aspect, the dipole is employed as an indicator that the integration preserves the biomaterial while bringing it into contact with the nanoelectronic devices. In another aspect, the dipole moment of the PM (or an alternative cellular or quasi-cellular component having a dipole) is employed to electrically influence the properties of adjacent nanostructures included in an exemplary nanoelectronic sensor embodiment having aspects of the invention, so as to produce measurable changes when the membrane interacts with a target species, such as an analyte of interest. For example, in a carbon nanotube capacitance sensor embodiment, the dipole moment of the PM may serve to increase the effective capacitance of the sensor, so that interactions of the PM with species which cause the dipole moment of the PM to change are in turn detected by the sensor as a measurable change in sensor capacitance. An analyte of interest may absorb onto or intercalate into the membrane so as to cause the dipole to change.

In the example of FIG. 21, PM isolated from *Halobacterium salinarum* was deposited on previously fabricated NTN-FETs. To determine the effect of the electric dipoles fixed in the PM, devices were prepared in three conditions: with the cytoplasmic side of the PM facing the nanotubes, with the extracellular side facing the nanotubes, and with a mixture of both orientations. View A illustrates mixed-orientation, the top substrate 29 is held to zero electrical potential, so that the rhodopsin dipoles point up and down with equal frequency. As a result, the PM contacts the nanotubes with both sides, and the net dipole moment, P, is zero.

View B illustrates cytoplasmic orientation, with −3 V on the top substrate 29, so that the net dipole moment is upwards and the PM contacts the nanotubes with the cytoplasmic side.

View C illustrates extracellular orientation, with +3 V on the top substrate 29, so that the net dipole moment is downwards and the PM contacts the nanotubes on the extracellular side. FIG. 22A shows a cross-section model of the cell membrane of *Halobacterium salinarum*. FIG. 22B shows an atomic force microscopy topograph of a completed nanobioelectronic device with mixed-orientation PM coating a nanotube network. PM is visible as irregular patches, one of which is outlined. The white line indicates the contour selected for a line section of the image, shown in the inset. As shown in FIG. 22B, the PM patch is uniformly 5 nm high. The films were measured by AFM to be 5 nm thick, which corresponds to monolayers of PM. Before and after deposition of PM, the NTN-FET transfer characteristics (conductance versus gate voltage) were measured.

Figure 23A:
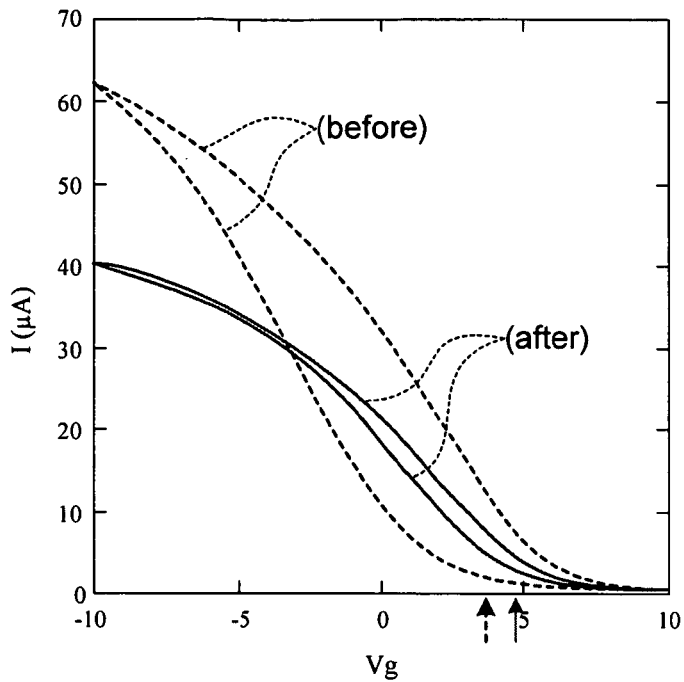
FIG. 23A shows a plot of the device characteristics before and after application of cell membrane, in the mixed orientation.
Figure 23B:
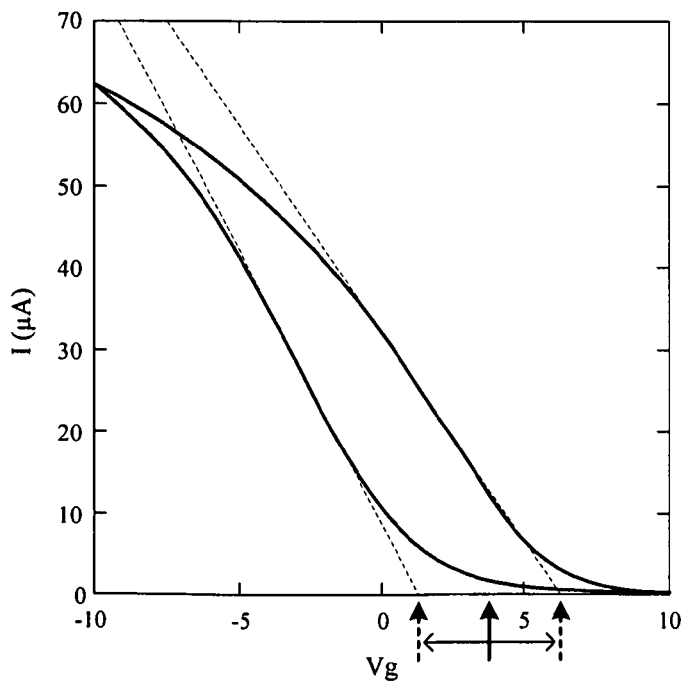
FIG. 23B shows a plot illustrating the calculation of the device parameters.

FIG. 23B. shows the transfer characteristics of the exemplary devices as influenced by the deposition of PM, i.e., after deposition in comparison to before deposition. In this example, the deposition mixed-orientation PM (see View A of FIG. 21), The curves show transfer characteristics (current versus gate voltage) (bias voltage=100 mV) for a device before (solid curve) and after (dashed curve) the deposition of cell membrane. Each transfer characteristic has two curves, from the right-moving sweep of gate voltage and the left-moving. The intrinsic threshold voltage, indicated by black and purple arrows respectively, is the average between the two sweeps.

FIG. 23B shows schematic transfer characteristic, illustrating the calculation of the device parameters. The width of the hysteresis is indicated by the pairs of horizontal arrows, drawn at a conductance of 50% of the maximum. The transconductances for the right- and left-moving sweeps are shown by dashed lines. Each transconductance is extrapolated back to zero current, where its intersection with the x-axis is the right-moving or left-moving threshold voltage. These two threshold voltages are indicated by arrows on the axis. The midpoint between them is the intrinsic threshold voltage, indicated by a third arrow.

The device embodiments shown in FIG. 23A operate as p-type transistors, conducting well at negative gate voltages and not conducting at positive gate voltages. In the region of zero gate voltage, the devices turned on sharply as the gate voltage was changed; this sharp turn-on, or high transconductance, has been attributed to the high mobility of charge carriers in carbon nanotubes. The sharp turn-on begins at a specific gate voltage, referred to as a threshold voltage. However, the devices showed significant hysteresis, in that different threshold voltages were measured using left-moving and right-moving sweeps of the gate voltage. The intrinsic threshold voltage is taken to be the average between the left-moving and right-moving threshold voltages. FIG. 23A highlights three main device parameters before and after deposition for a typical device. The changes described here were observed repeatedly in several devices prepared in the same way. First, the hysteresis loops narrowed significantly, as indicated by the arrows. In this case, the width decreased from 3.5 V to 0.8 V. Second, the threshold voltage changed by +1.0±0.2 V, as indicated by the arrows on the x-axis. Finally, the transconductance decreased by about 20%. As discussed below, these changes show that the PM has been successfully integrated with the NTN-FETs.

Figure 23C:
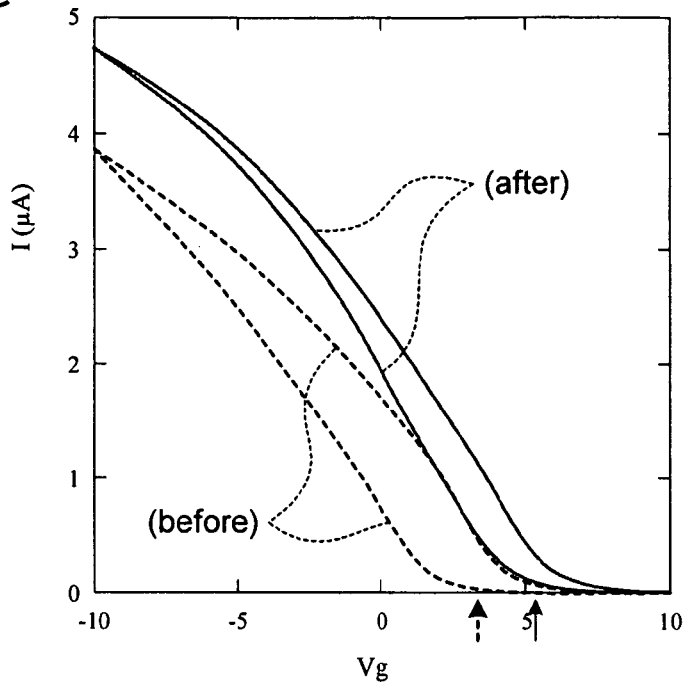
FIG. 23C shows a plot of the device characteristics before and after application of cell membrane, with the cytoplasmic side attached.
Figure 23D:
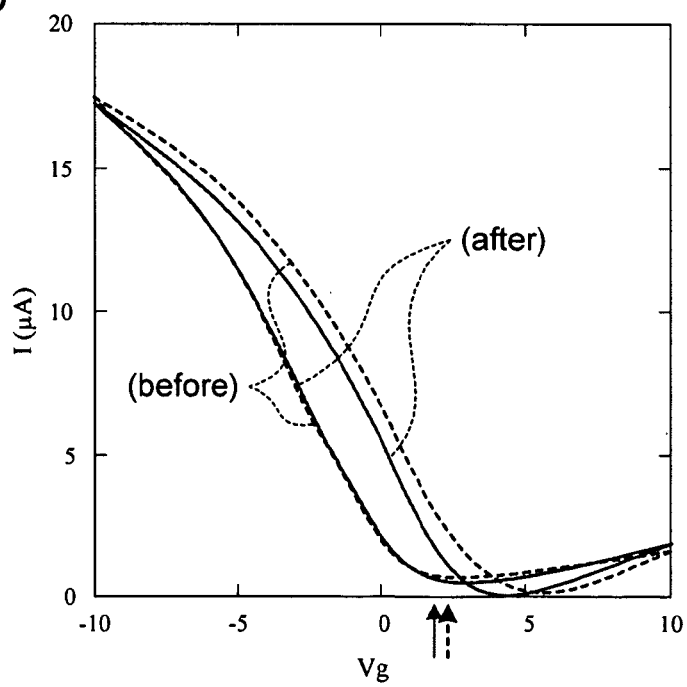
FIG. 23D shows a plot of the device characteristics before and after application of cell membrane, with the extracellular side attached.

FIGS. 23C and 23D show the characteristics and effects of oriented PM deposition. In both orientations the membrane deposition caused a narrowing of the hysteresis loops similar to that caused by the mixed-orientation deposition. At the same time, the threshold voltages shifted, in opposite directions according to the orientation of the membrane. Note that the transconductance did not change, although the maximum conductance changed in accordance with the shifts in the threshold voltage.

FIG. 23C shows the transfer characteristics (bias voltage=100 mV) before (black) and after (purple) the deposition of membrane oriented with the cytoplasmic side contacting the nanotubes (see View b of FIG. 21). For the cytoplasmic orientation, the hysteresis width decreased from 1.2 V to 0.8 V; and the threshold voltage shifted by +2.2±0.2 V.

FIG. 2C shows the transfer characteristics (bias voltage=100 mV) before (black) and after (purple) the deposition of membrane oriented with the extracellular side contacting the nanotubes (see View c of FIG. 21). For the extracellular orientation, the hysteresis width decreased from 1.3 V to 0.9 V; and the threshold voltage shifted by −0.4±0.2 V.

A number of features on the integrated devices are demonstrated in FIGS. 2A-2C: First, the transconductance of a nanobioelectronic transistor is shown. This quantity is associated with the capacitance between the nanotube network, which forms the channel of the NTN-FET, and the gate; and with the mobility of carriers within the nanotube network. The gate-network capacitance is shown to be constant as a result of membrane deposition; this is confirmed by the fact that the transconductance is not changed by oriented membrane deposition. In the case of mixed-oriented membrane deposition, the alternation of positive and negative electric dipoles on a length scale of about 500 nm (the diameter of a typical patch of PM) acts as a significant random scattering potential, which decreases the carrier mobility in the network. Thus, the decrease in transconductance in FIG. 23A is a direct result of the mixture of orientations.

Secondly, the hysteresis decreased dramatically in all cases as a result of the biological coating. The hysteresis results from adsorbed water on the substrate; in addition, coatings which displace water from the nanotubes reduce the hysteresis. Consequently, there is a decrease in hysteresis here as well, as the PM remains intact as a layer contacting the nanotubes. Moreover, the width of the remaining hysteresis is similar for all three conditions, which indicates that the amount of PM coverage is similar. This conclusion was confirmed in randomly selected spots that were imaged by AFM.

Lastly, The shift of the threshold voltage in the devices results from the electrostatic field associated with the bacteriorhodopsin electric dipole. This field induces charge in the nanotubes, thus shifting the Fermi level. The position of the Fermi level is measured by the threshold voltage, and there is an relationship between the threshold voltage in various device configurations and the quantity of charge induced in the nanotubes. In this example, with a typical nanotube diameter of 2 nm, every 1 μm of nanotube length has a capacitance to the gate, $C_{bg}$, of about 15 aF. The induced charge, $\Delta Q$, is given by $\Delta Q = C_{bg} \Delta V$, where $\Delta V$ is the threshold shift. Thus, the +1.1 V shift caused by mixed-orientation PM deposition corresponds to an induced charge of 16 aC/μm of nanotube length. Note that this dipole effect is important to the second embodiment type of this example, the nanoelectronic capacitance sensor.

Thus, by demonstrating these three device parameters, it is shown that the nanobioelectronics integration is successful. First, the NTN-FETs' transistor functionality is preserved. Second, the PM remains intact as a layer, and the bacteriorhodopsin membrane proteins retain their electric dipoles. Third, the deposited PM is demonstrated to contact the NTN-FETs directly and to interact with their electrical properties.

The examples of FIGS. 23A-C demonstrate a significant asymmetry between cytoplasmic and extracellular orientations. This asymmetry is reflected in the large amount of charge induced in mixed-orientation devices, since without an asymmetry, the charge induced by equal amounts of cytoplasmic- and extracellular-oriented PM would cancel. This assumption, that the mixed-orientation film contains equal amounts of cytoplasmic and extracellular orientations, is justified by these observations. First, it is shown that the exemplary deposition method produces similar coverages for both orientations. Therefore, neither orientation adsorbs preferentially compared to the other, and a random mixture should contain equal amounts of each. Second, the threshold shift observed with mixed orientation correlates with the expectation from a 50%-50% mixture. The two oriented depositions cause +2.2 V and −0.4 V of threshold shift. For a 50%-50% mixture, we expect a net threshold shift of ½(2.2−0.4)V, or +0.9 V. This value agrees well with the value observed with mixed orientation, 1.0±0.2 V. From these two observations, we conclude that the mixed-orientation film is in fact a 50%-50% mixture. Such an asymmetry results from the fact that the dipole is closer to one side of the PM than the other. Here we are able to observe this asymmetry directly because of the device configuration in which the PM contacts the nanotubes directly.

Figure 24A:
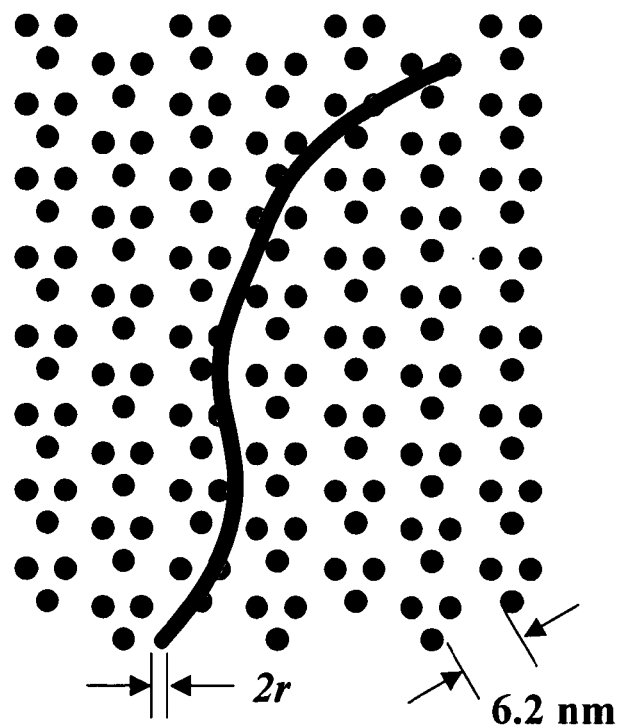
FIGS. 24A-24B show models illustrating cell membrane geometry.
Figure 24B:
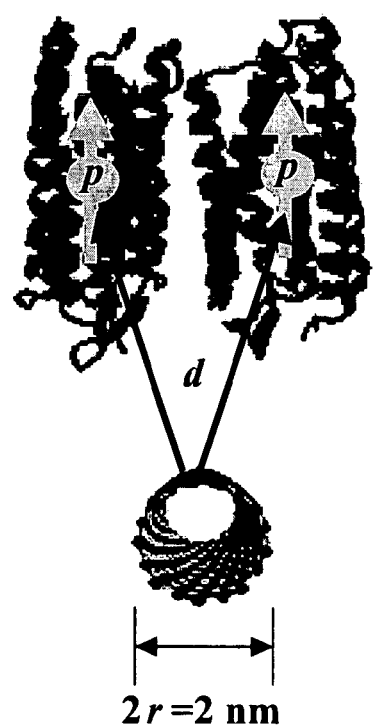

FIGS. 24A and 24B illustrate modeling of the electrostatic effect of the bacteriorhodopsin dipole on the nanotubes, permitting quantification of the asymmetry. Note in this regard that the background charge due to the phosphate heads of the lipids of the PM is 0.2 electrons per square nanometer, which is too weak to explain the charge induced in the example devices. The rhodopsin dipole is known to result from the competition between several charge distributions that result in a net dipole moment of $3.3 \times 10^{-28}$ C·m per rhodopsin monomer FIG. 24A illustrates an electrostatic model of the geometry of the PM and rhodopsin molecules with respect to the nanotubes, which may be used to calculate the effect of this dipole on the nanotubes. The rhodopsin molecules are shown above a nanotube and form a line of constant dipole density (see section "Model of an integrated nanobioelectronic device", below). Rhodopsin (purple dots) assembles into trimers, which are arranged on a hexagonal lattice. Each nanotube resembles a curved line which meanders across the lattice, contacting rhodopsins over its width of about 2 nm. Since the rhodopsin dipole density is about $6.0 \times 10^{-29}$ C·m/nm², the nanotube contacts a line density of $\pi = 1.2 \times 10^{-25}$ Cm/μm of nanotube length.

FIG. 24B illustrates a detail model of the association of rhodopsin molecules with a nanotube and illustrates the dimensions used in the calculations. A typical nanotube has a typical diameter of about 2 nm. A rhodopsin monomer situated near a nanotube has a dipole moment p. Although this dipole arises from a complex extended charge distribution, it is represented by a point dipole for simplicity. This point dipole is situated within the rhodopsin at a distance d from the nanotube surface. In the model, the line of dipoles with a density $\pi$ induces a charge density, $\lambda$, given by $\lambda = -r\pi/d^2$. Thus, by combining the known dipole moment of bacteriorhodopsin with the induced charge (measured from the threshold voltage shift and the known capacitance), we calculate how far the dipoles lie from the nanotubes.

The answer will be different for the two different orientations, reflecting the position of the dipoles closer to one side of the PM. For the cytoplasmic orientation, with $\Delta V_{cp} = +2.2$ V, we calculate $d_{cp} = 1.9$ nm. For the extracellular orientation, with $\Delta V_{cp} = -0.4$ V, we have $d_{ec} = 4.4$ nm. Since the sum of these distances, 6.3 nm, is comparable to the membrane bilayer thickness of 5 nm, we conclude that this simple model is reasonable. Note, in particular, that since the ratio between $\Delta V_{cp}$ and $\Delta V_{ec}$ is 5.5, the electrostatic model indicates that $d_{cp}$ is 2.3 times smaller than $d_{ec}$. Thus, our data contribute additional details about the asymmetry of the bacteriorhodopsin charge distribution.

Purple membrane (PM) was isolated from *Halobacterium salinarum*, and a suspension of PM in water was prepared at a rhodopsin concentration of 1 mM. Before coating the NTN-FETs, the suspension was freshly mixed with a shaker and warmed to 27° C. A drop of suspension was placed on a chip, and the chip was covered with a blank piece of silicon substrate. The assembly was kept in a chamber at 50% RH for 5 minutes, after which the NTN-FET was blown dry. This procedure was repeated three times to produce films of mixed-orientation PM coating the nanotube network. The film thicknesses were measured by AFM to be 5 nm, which corresponds to monolayers of PM. To produce oriented films, a voltage of ±3 V was applied between the two chips while they were exposed to the suspension. After the deposition of the membranes, the devices were air-dried for several hours at 40% RH. Electrical properties were measured before deposition and after air-drying, by applying a fixed source-rain bias voltage between contacts on the network and measuring the source-drain current as a function of gate voltage. The membrane suspension and the chips were kept in dark enclosures throughout the experiment to ensure that the bacteriorhodopsin was in its dark-adapted state.

Model of an Integrated Nanobioelectronic Device.

We use a simple electrostatic model in which the rhodopsin molecules above a nanotube form a line of constant dipole density. Those in the rest of the PM (FIG. 24A) are ignored, because for dipoles farther from the nanotube the induced charge decays rapidly with distance. In this model, the nanotube is considered to be a conducting cylinder of radius r (for our nanotubes, this is typically 1 nm). A length of 1 µm of such a nanotube contacts a membrane area of 2,000 nm². From the known area density of the dipole moment in PM, $6.0 \times 10^{-29}$ C·m/nm², we calculate that the nanotube contacts a dipole density of $\pi = 1.2 \times 10^{-25}$ Cm/µm. The line of dipoles induces a charge density A, in the conducting cylinder: $\lambda = -r\pi/d^2$, where d is the distance between the nanotube surface and the dipole.

Let us suppose that the rhodopsin dipole is a point dipole embedded within the PM at a distance $d_{cp}$ from the cytoplasmic side and $d_{ec}$ from the extracellular side, as illustrated in FIG. 24B. Then the dipole will induce different amounts of charge, $\lambda_{cp}$ and $\lambda_{ec}$, depending on which side contacts a nanotube. For the cytoplasmic case, with $\Delta V_{cp}=+2.2$ V, we have $\lambda_{cp}=33$ aC/µm. Using the equation above, we calculate $d_{cp}=1.9$ nm. Similarly, for the extracellular case, with $\Delta V_{ec}=-0.4$ V, we have $\lambda_{ec}=6$ aC/µu m, and $d_{ec}=4.4$ nm. Since the sum of these distances, 6.3 nm, is comparable to the membrane bilayer thickness of 5 nm[10], we conclude that this simple model is reasonable. Note, in particular, that since the ratio between $\Delta V_{cp}$ and $\Delta V_{ec}$ is 5.5, the electrostatic model predicts that $d_{cp}$ is 2.3 times smaller than $d_{ec}$. Thus, the charge density of the rhodopsin dipole is situated closer to the cytoplasmic side of the membrane.

The following publications are incorporated by reference: Bradley, et al., *Flexible Nanotube Electronics*, Nano Letters 2003 3, 1353-55; Bradley, K., et al., Phys. Rev. Lett. 2003, 91, 218301; Gabriel, J-C. P., *Large Scale Production Of Carbon Nanotube Transistors: A Generic Platform For Chemical Sensors*, Mat. Res. Soc. Symp. Proc. 2003, 762, Q.12.7.1-Q.12.7.7; and Star, A., et al., Nano Letters 2003, 3, 459.

Devices having aspects of the invention can be used to interrogate cell membranes or cellular events. In particular, it is well known that when bacteriophage disrupt the bacterial membrane, a large ionic gradient occurs. Again, this type of biochemical disruption in the proximity of the CNT capacitance plate can be measured and used as a bacterial species identifier. Note in this regard examples of FIGS. 20-23 with respect to PM membranes, in which the electrical properties of the nanotube network changed as a result of the electrostatic field associated with the bacteriorhodopsin electric dipole. This dipole effect is also effects the measured capacitance of exemplary devices including such membranes (and/or other dipole enhancers) as functionalization.

Figure 25:
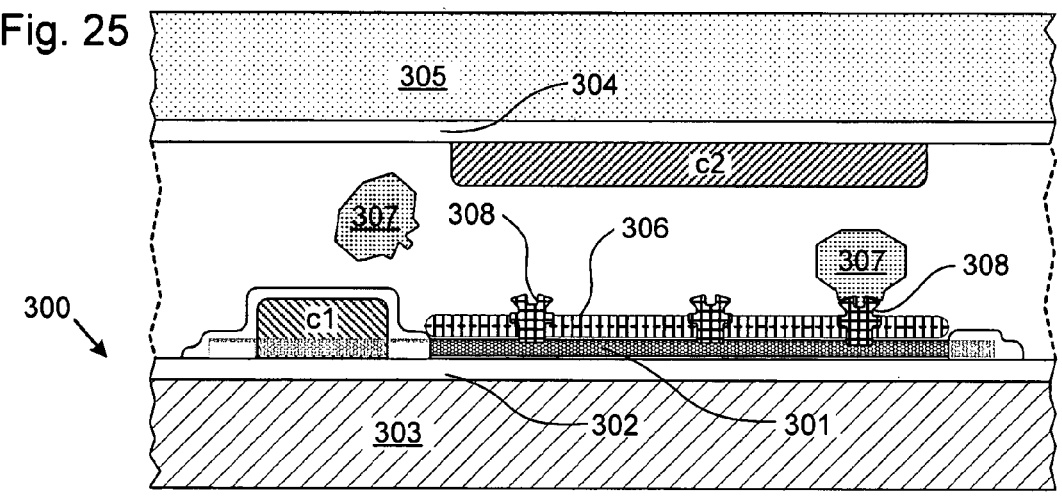
FIG. 25 shows a schematic cross section of an exemplary sensor having aspects of the invention and employing cell membrane functionalization.

FIG. 25 illustrates the structure of an exemplary device 300 having aspects of the invention. A nanotube conductive layer 301 (such as a nanotube network) is disposed on the dielectric surface 302 of a lower substrate 303. Contact c1 communicates with the nanotube layer (a single contact c1 is shown, but c1 may include a plurality of contacts, such as source-drain pairs, and the like). The contact is shown optionally passivated, see U.S. patent application Ser. No. 10/280,265 entitled "Sensitivity Control for Nanotube Sensors" which application is incorporated herein by reference. Spaced apart from the nanotube network by an analyte media space a second plate contact C2, disposed on the dielectric surface 304 of an upper substrate 305. As a voltage is applied between C1 and C2, this structure acts as a capacitor. Note that the lower substrate 303 (or a distinct lower gate) may also function as a counter electrode for capacitance measurements and/or for transistor measurements.

Functionalization includes at least one cell membrane bi-layer 306 applied to the nanotube layer in the manner described above. The cell membrane may be derived from prokaryotic and/or eukaryotic source organisms, or may be synthetically simulated using natural or artificial lipid layers. The cell membrane responds to at least one analyte of interest in the media 307 so as to produce a measurable change in the capacitance (measurement circuitry not shown). In certain embodiments, the analyte effects a change in the properties of nanostructure (e.g., nanotube(s)) 301 by direct interaction with the membrane bi-layer or nanotubes. In alternative embodiments a cell wall receptor or other functional biostructure 308 has specific activity to respond to analyte 308, for example by ligand binding (e.g., virus analyte attachment, and the like), so as to produce a detectable change in the properties of nanotubes 301. Note that the techniques described above permit convenient orientation of cell membranes having a dipole moment.

Figure 26:
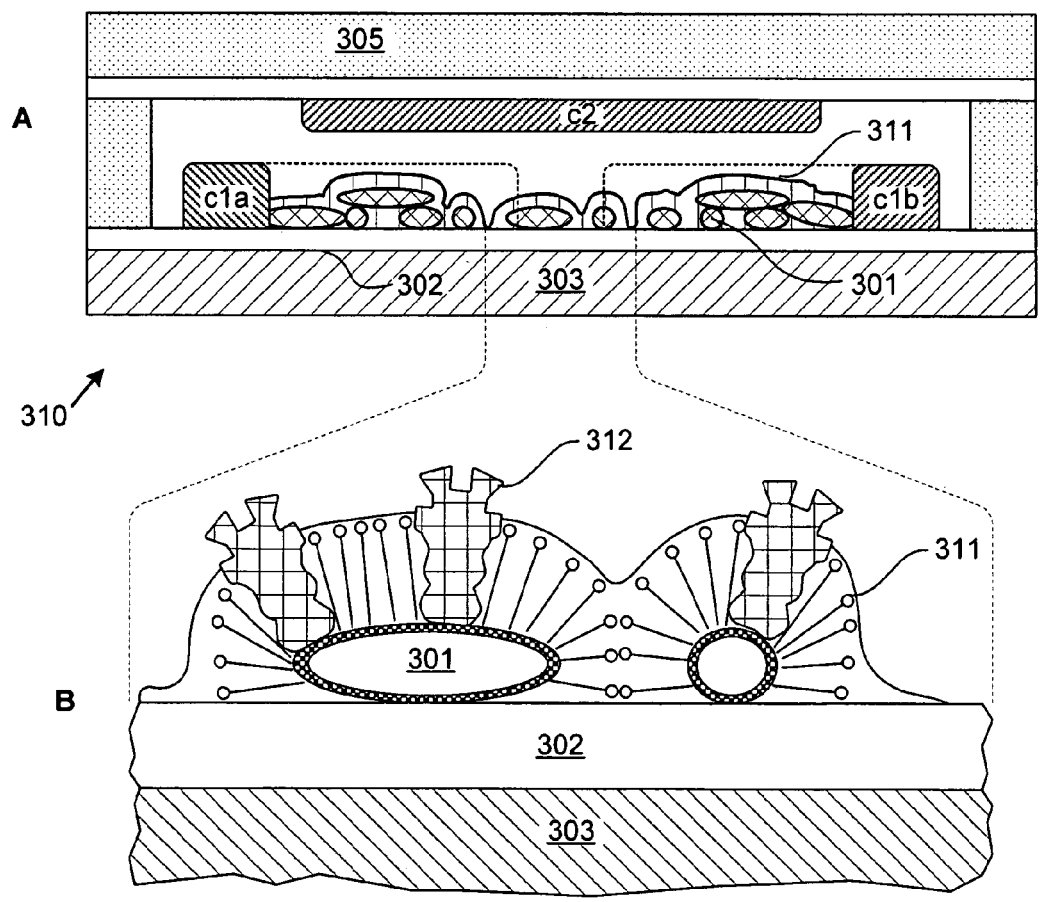
FIG. 26 shows a schematic cross section of an exemplary sensor having aspects of the invention and employing lipid monolayer functionalization.
Figure 27:
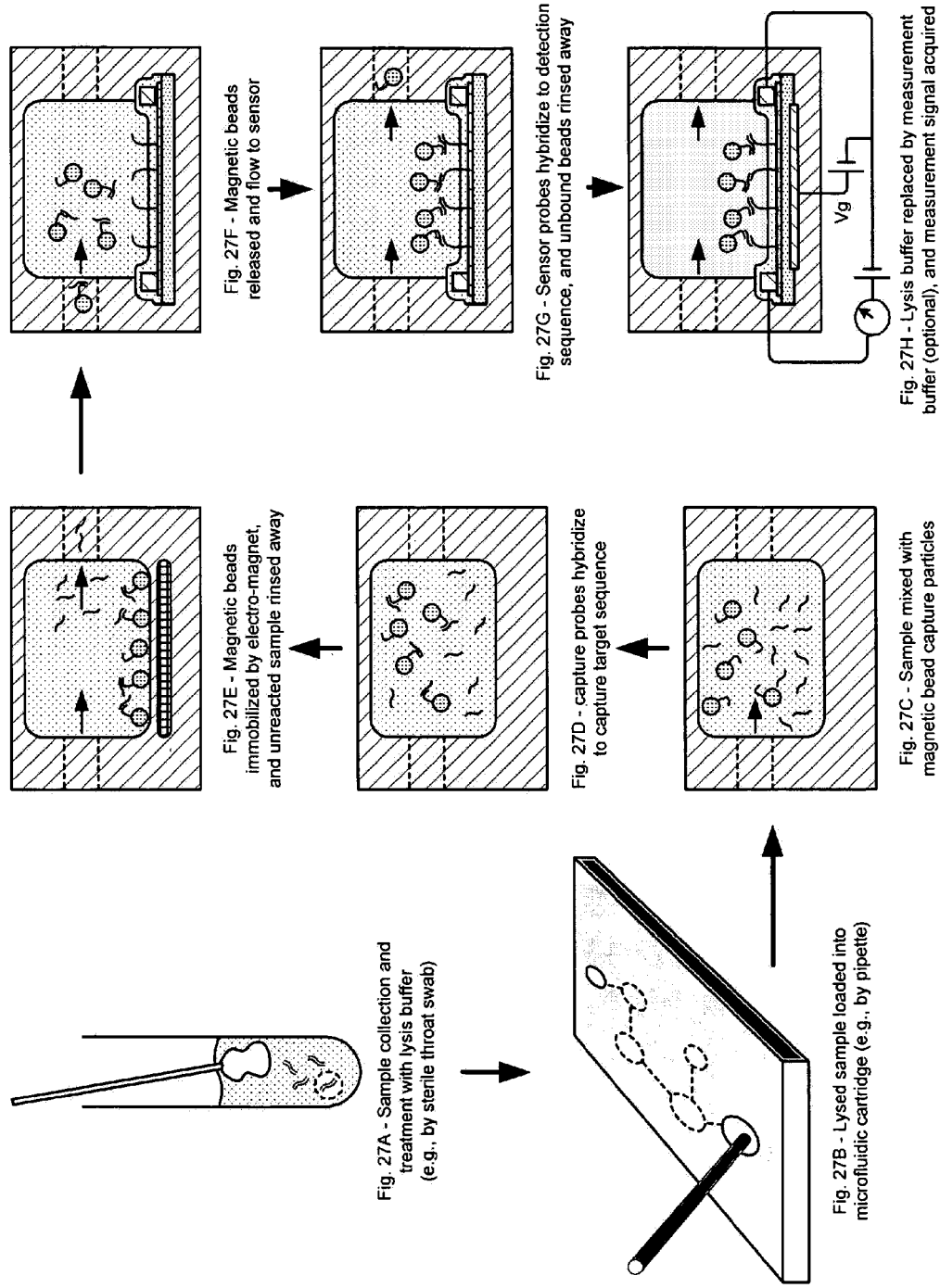
FIGS. 27A-27H illustrate exemplary diagnostic assay and detection cartridge embodiments.

FIG. 26 illustrates the structure of an exemplary device 310 having aspects of the invention, comprising a structure generally similar to the embodiment shown in FIG. 25, and having like reference numerals for most elements. The View A shows a cross-section of the device, schematically indicating an interconnecting nanotube network 301 seen in section. The View B shows a magnified detail of a portion of the nanotube network of View A. An interdigitated source-drain pair of contacts c1*a* and c1*b* are shown in contact with nanotube network 301.

Functionalization includes, in this example, a lipid monolayer 311 in association with the nanotubes 301. The lipid monolayer 311 may be composed of natural phospholipids, or alternative biomolecules or synthetic groups of comparable properties. Conveniently, native carbon nanotubes have hydrophobic properties which assist in orienting or self-assembling the polar surface groups of the lipids away from the nanotubes 301. Lipid monolayer 311 provides a microenvironment suitable for the functioning of a variety of alternative cell wall receptor or other functional bio-structure 312, which typically have a biomolecular structure suited embedding in a phospholipid monolayer. Receptor or other functional bio-structure 312 has specific activity to respond to an analyte, so as to produce a detectable change in the properties of nanotubes 301.

FIGS. 27A-27G correspond to FIGS. 11A-11G of priority U.S. Provisional Application No. 60/668,879, filed Apr. 5, 2005, entitled "Nanoelectronic System For Virus Detection and Identification", which is claimed as priority by parent U.S. patent application Ser. No. 11/318,354 filed Dec. 23, 2005, each of which applications are incorporated by reference. These figures illustrate exemplary diagnostic assay and detection cartridge embodiments having aspects of the invention, arranged sequentially in the manner of a process step flow chart (showing an viral genome sequence detection example):

FIG. 27A—A sample is collected and treated with lysis buffer (e.g., by sterile throat swab). Although shown as a test-tube procedure, the cartridge may include a port for direct introduction of the sample, and incorporate the lysis step. In alternative systems, various bio-sampling devices may be included, such as breath condensers or filters, micro-syringes and the like to obtain a patient sample. Note that the buffer may be selected to optimize the assay. In the event that whole pathogens are to be detected, e.g., by surface groups, and the like, the buffer may preserve this form. Typically, it is desired to lyse and fragment the pathogen, releasing such detectable species as genomic RNA, DNA, single or double stranded polynucleotides, and the like, and/or detectable envelope fragments and the like.

FIG. 27B—The lysed sample loaded into microfluidic cartridge (e.g., by pipette). Also the cartridge may incorporate this step. The cartridge be constructed generally as described above with respect to "hybridization stringency" and the device of FIG. 9, and may include a wide range of components and features know in the art of microfluidic analytic devices. The cartridge may be prepared as a disposable kit including reagents and materials, either contained in reservoirs of the cartridge or in separate dispensing containers, such as bubble packs.

FIG. 27C—The lysed sample is mixed with magnetic bead capture particles. In this example, the beads are preferably supplied conjugated to one or more capture probes optimized for the assay. Optionally additional reagents can be added at this (and/or other) stages to optimize the buffer for the process step, e.g. for hybridization efficiency.

FIG. 27D—The capture probes hybridizes to the capture target sequence on the sample. Note description above under "hybridization stringency", the cell or chamber temperature and other environmental conditions may be controlled to optimize the hybridization.

FIG. 27E—The magnetic beads with capture probes are immobilized by a magnet, preferably a switchable electromagnet, and unreacted lysed sample rinsed away. Note that beads both with and without hybridized sample are immobilized.

FIG. 27F—The magnetic beads are released (magnet turned off or removed) and flow to a sensor chamber. Note, the chamber transfer and flow pattern is exemplary, and the cartridge architecture may be arranged to perform the steps at different regions without departing from the spirit of the invention.

FIG. 27G—The sensor has detection probes conjugated in association with the nanostructures. A schematic NTFET is shown with the detection probes bound on or through a surface layer, e.g. a polymer layer to prevent non-specific binding, to repel buffer, and the like. The detection probes hybridizes to detection sequence on the sample, so as to immobilize the sample and associated magnetic bead. Note, as with steps 27C and 27D, the stringency conditions may be controlled and adjusted to optimize hybridization and specificity of the detection probe. Magnetic beads without captured sample remain unbound to the detection probes and are preferably rinsed away, so as not to influence the measurement signal. As described above, magnetic bead dipole attraction may be employed to concentrate sample near the sensor.

FIG. 27H—Following the completion of detection probe hybridization step, the environment of the sensor chamber can be optimized for signal acquisition, with parameters selected so as to stabilize the detection hybridization bonds (and preferably also stabilize the capture hybridization bonds) while promoting optimum signal discrimination and sensitivity. This may optionally include temperature adjustment, magnetic or electrical field adjustment, and the like. Optionally the hybridization buffer may be rinsed away and replace with a measurement buffer without disturbing the hybridization bonds or disengaging the bound sample/beads. The measurement signal may then be acquired. The schematic shows a NTFET with gate voltage modulation (enabling a variety of alternative measurement strategies as described herein). Alternatively the sensor may be purely resistive, or may be a capacitive sensor and the like. As described above, magnetic bead dipole effects may be employed to increase signal to noise ratio and sensitivity.

In other alternatives (not shown in FIG. 27), a combination of different sensors may be included within the cartridge (in the same or separate chambers), either in array, in parallel steps or in series steps. For example, a plurality of sensors may be included to increase discrimination or sensitivity by pattern recognition, to increase discrimination or sensitivity by detecting more than one kind of pathogen-specific fragment (e.g., a RNA fragment and a protein fragment specific to the same virus), to provide a multi-pathogen panel detector, and the like.

Figure 28:
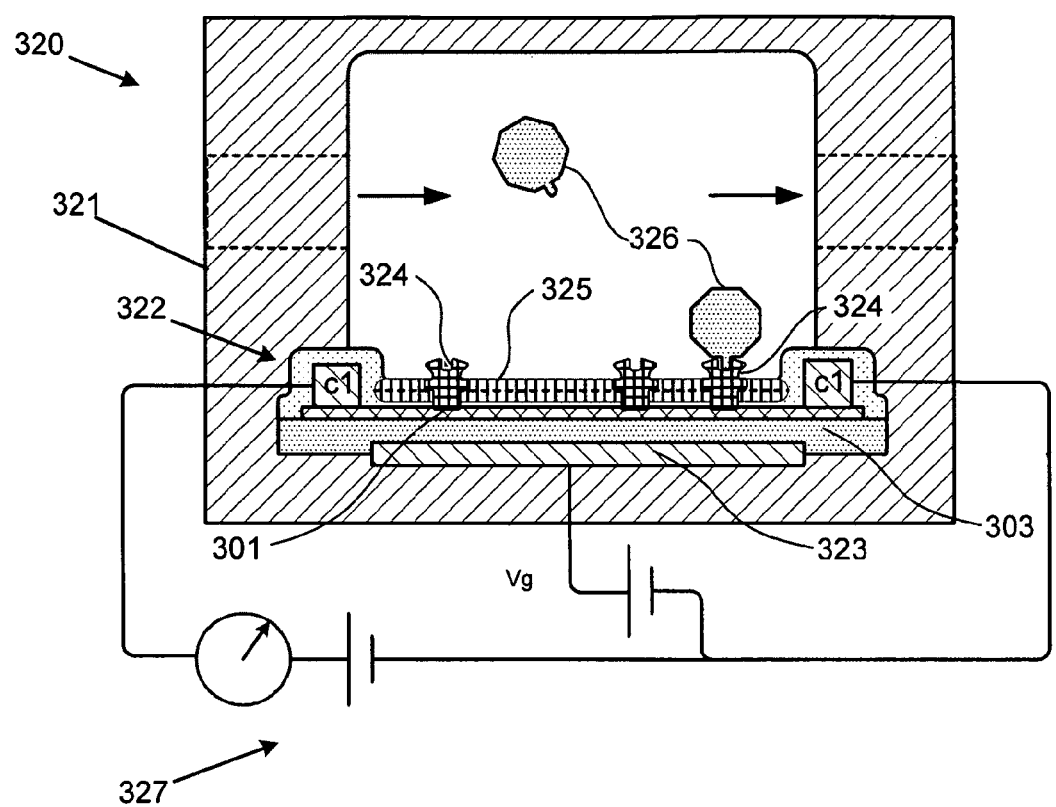
FIG. 28 illustrates an exemplary device 320 comprising a detector cell 321 and a sensor device 322 configured to detect virus particles or virions directly, without lysis or involved sample processing.

FIG. 28 illustrates the structure of an exemplary device 320 having aspects of the invention comprising a detector cell 321 generally similar to that of FIG. 27H, and having a sensor device 322 comprising a structure generally similar to the embodiment shown in FIG. 25, and having like reference numerals for most elements. In contrast to the detection system described in FIGS. 24A-H, the device 320 is configured to detect virus particles or virons directly, without lysis or involved sample processing. Sensor 322 comprises substrate 303 and adjacent nanostructure 301 (e.g., nanotube network). Cell membrane 325 (or alternative membrane structure, such as in FIG. 26) is disposed in communication with nanotube network 301, and includes embedded receptors 324. Receptors 324 have a specific affinity for surface groups of virons 326. The binding of so as to bind virons 326 to receptors 324 produces a detectable change in the properties of nanotubes 301 (or other nanostructure) so as to permit circuitry 327 to detect the presence of virons 326. A distinct counter or gate electrode 323 is shown but the device 322 may include alternative counter electrodes as in FIGS. 25 and 26, and circuitry may measure one or more properties, such as capacitance, resistance, impedance, hysteresis, transistor characteristics, and the like.

Having thus described preferred embodiments of the methods and devices having aspects of the invention, it should be apparent to those skilled in the art that certain advantages of the within system have been achieved. It should also be appreciated that various modifications, adaptations, and alternative embodiments thereof may be made within the scope and spirit of the present invention.

We claim:

1. A sensor, comprising:
   a substrate;
   a conductive base disposed adjacent the substrate;
   a dielectric material covering at least a region of the conductive base;
   one or more nanostructures disposed adjacent the dielectric material and capacitively coupled to the conductive base; and
   a top lead electrically communicating to the one or more nanostructures, wherein said top lead extends substantially across the one or more nanostructures.

2. The sensor of claim 1, wherein the one or more nanostructures comprises a network of carbon nanotubes.

3. The sensor of claim 2 further comprising a functionalization material disposed adjacent the carbon nanotubes.

4. A sensor comprising:
   a substrate having a first region;
   first and second conductive leads disposed adjacent the substrate and spaced apart from the first region;
   a dielectric material disposed adjacent at least the first region; and
   first and second nanostructure layers in electrical communication with the first and second conductive leads respectively, the nanostructure layers each including one or more nanostructures, the nanostructure layers arranged adjacent the first region and configured so as to be separated with respect to each other by the dielectric material, wherein the lengthwise dimensions of the one or more of the nanostructures are aligned generally parallel with the substrate.

5. The sensor of claim 4, wherein the one or more of the nanostructure layers comprises a network of carbon nanotubes.

6. The sensor of claim 4, further comprising a functionalization material disposed adjacent the carbon nanotubes.

7. The sensor of claim 4, wherein at least a portion of the substrate and at least a portion of the dielectric material is porous and configured to permit an analyte medium to pass through the substrate first region.

* * * * *